United States Patent
Lahm

(10) Patent No.: US 7,666,882 B2
(45) Date of Patent: Feb. 23, 2010

(54) ANTHRANILAMIDE INSECTICIDES

(75) Inventor: George Philip Lahm, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 507 days.

(21) Appl. No.: 10/529,612

(22) PCT Filed: Nov. 12, 2003

(86) PCT No.: PCT/US03/36167

§ 371 (c)(1),
(2), (4) Date: Mar. 30, 2005

(87) PCT Pub. No.: WO2004/046129

PCT Pub. Date: Jun. 3, 2004

(65) Prior Publication Data

US 2006/0014808 A1    Jan. 19, 2006

Related U.S. Application Data

(60) Provisional application No. 60/426,693, filed on Nov. 15, 2002.

(51) Int. Cl.
*A61K 31/4439* (2006.01)
*C07D 401/04* (2006.01)
(52) U.S. Cl. .................... 514/341; 546/276.1
(58) Field of Classification Search .............. 546/275.4, 546/376.1; 514/341
See application file for complete search history.

(56) References Cited

U.S. PATENT DOCUMENTS

| | | | |
|---|---|---|---|
| 5,998,424 A | 12/1999 | Galemmo, Jr. et al. | |
| 6,020,357 A | 2/2000 | Pinto et al. | |
| 6,403,620 B1 | 6/2002 | Galemmo, Jr. et al. | |
| 6,548,512 B1 | 4/2003 | Pinto et al. | |
| 6,602,895 B2 | 8/2003 | Galemmo, Jr. et al. | |
| 6,747,047 B2 * | 6/2004 | Lahm et al. | 514/341 |
| 6,965,032 B2 * | 11/2005 | Freudenberger | 546/275.4 |
| 6,995,178 B2 * | 2/2006 | Lahm et al. | 514/354 |
| 7,038,057 B2 | 5/2006 | Annis et al. | |
| 7,087,598 B2 | 8/2006 | Clark | |
| 7,148,217 B2 | 12/2006 | Selby | |
| 7,157,475 B2 | 1/2007 | Clark | |
| 7,179,824 B2 | 2/2007 | Zimmerman | |
| 7,199,138 B2 | 4/2007 | Finkelstein et al. | |
| 7,211,270 B2 | 5/2007 | Lahm et al | |
| 7,227,025 B2 | 6/2007 | Freudenberger et al. | |
| 7,232,836 B2 | 6/2007 | Lahm et al. | |
| 7,241,767 B2 | 7/2007 | Clark et al. | |
| 7,288,554 B2 | 10/2007 | Finkelstein et al. | |
| 7,335,780 B2 | 2/2008 | Annis | |
| 7,338,978 B2 * | 3/2008 | Lahm et al. | 514/616 |
| 7,339,057 B2 | 3/2008 | Taylor | |
| 2004/0102324 A1 | 5/2004 | Annis et al. | |
| 2004/0110777 A1 | 6/2004 | Annis et al. | |
| 2004/0209923 A1 | 10/2004 | Berger et al. | |
| 2005/0075372 A1 | 4/2005 | Lahm et al. | |
| 2005/0147633 A1 | 7/2005 | Stevenson | |
| 2006/0167060 A1 | 7/2006 | Lahm et al. | |
| 2007/0203342 A1 | 8/2007 | Freudenberger et al. | |

FOREIGN PATENT DOCUMENTS

| | | |
|---|---|---|
| EP | 0 287 851 A | 10/1988 |
| EP | 0 946 508 A1 | 10/1999 |
| EP | 0 991 625 B1 | 6/2005 |
| WO | WO98/28269 | 7/1998 |
| WO | WO98/57937 | 12/1998 |
| WO | WO 01/70671 A2 | 9/2001 |
| WO | WO 02/070483 A | 9/2002 |
| WO | WO 02/094791 A | 10/2002 |
| WO | WO 03/015518 A1 | 2/2003 |
| WO | WO 03/015519 A1 | 2/2003 |
| WO | WO 03/016282 A2 | 2/2003 |
| WO | WO 03/016283 A1 | 2/2003 |
| WO | WO 03/016284 A1 | 2/2003 |
| WO | WO 03/024222 A1 | 3/2003 |
| WO | WO 03/106427 A2 | 12/2003 |

\* cited by examiner

*Primary Examiner*—Kamal A Saeed
*Assistant Examiner*—Samantha L Shterengarts

(57) ABSTRACT

This invention provides compounds of Formula I, N-oxides and suitable salts thereof

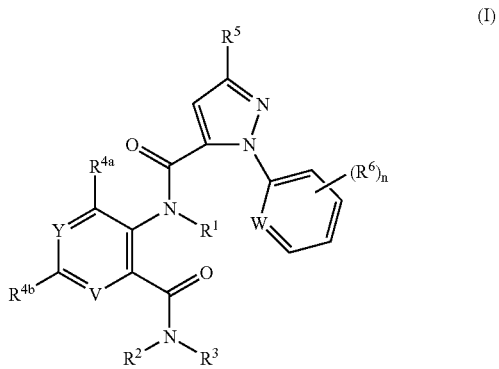

wherein Y and V are each independently N or $CR_{4a}$; W is N, CH or $CR_6$; and $R_1$ through $R_6$, and n are as defined in the disclosure. This invention also pertains to a composition for controlling an invertebrate pest comprising a biologically effective amount of a compound of Formula I, an N-oxide thereof or an agronomic or nonagronomic suitable salt of the compound and at least one additional component selected from the group consisting of a surfactant, a solid diluent and a liquid diluent, and optionally further comprising an effective amount of at least one additional biologically active compound or agent. Also disclosed are methods for controlling an invertebrate pest comprising contacting the invertebrate pest or its environment with a biologically effective amount of a compound of Formula I, an N-oxide thereof or an agronomic or nonagronomic suitable salt of the compound or with the composition described herein.

6 Claims, No Drawings

ANTHRANILAMIDE INSECTICIDES

FIELD OF THE INVENTION

This invention relates to certain heterocyclic amides, their N-oxides, salts and compositions suitable for agronomic and nonagronomic uses, including those uses listed below, and a method of their use for controlling invertebrate pests in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes, but the need continues for new compounds that are more effective, less costly, less toxic, environmentally safer or have different modes of action.

WO 01/070671 discloses N-acyl anthranilic acid derivatives of Formula i as arthropodicides

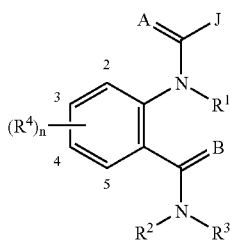

i wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$-$C_6$ alkyl; $R^2$ is H or $C_1$-$C_6$ alkyl; each $R^4$ is independently H, $C_1$-$C_6$ alkyl, $C_1$-$C_6$ haloalkyl, halogen or CN; and n is 1 to 4.

SUMMARY OF THE INVENTION

This invention provides compounds of Formula I, their N-oxides and agronomic or nonagronomic suitable salts thereof

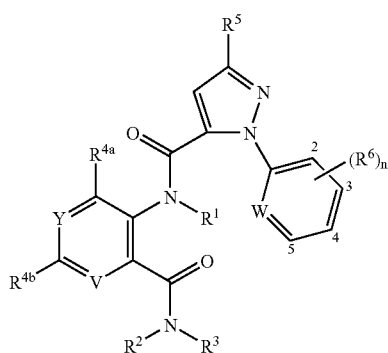

I wherein
Y and V are each independently N or $CR^{4a}$;
W is N, CH or $CR^6$;
$R^1$ is H; or $C_1$-$C_6$ alkyl, $C_2$-$C_6$ alkenyl, $C_2$-$C_6$ alkynyl or $C_3$-$C_6$ cycloalkyl, each optionally substituted with 1 to 5 substituents independently selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or
$R^1$ is $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl;
$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;
$R^3$ is H; G; $C_1$-$C_6$ alkyl, $C_2$-$C_6$ alkenyl, $C_2$-$C_6$ alkynyl or $C_3$-$C_6$ cycloalkyl, each optionally substituted with 1 to 5 substituents independently selected from the group consisting of halogen, G, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, phenyl, phenoxy and 5- or 6-membered heteroaromatic ring, each phenyl, phenoxy and 5- or 6-membered heteroaromatic ring optionally substituted with 1 to 3 substituents independently selected from $R^{14}$; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl; $C_2$-$C_6$ alkylcarbonyl; or phenyl optionally substituted with 1 to 3 substituents independently selected from $R^{14}$; or
$R^2$ and $R^3$ are taken together with the nitrogen to which they are attached to form a ring which includes 2 to 6 atoms of carbon and optionally one additional atom of nitrogen, sulfur or oxygen, said ring optionally substituted with 1 to 4 substituents independently selected from the group consisting of $C_1$-$C_2$ alkyl, halogen, CN, $NO_2$ and $C_1$-$C_2$ alkoxy;
G is a 5- or 6-membered nonaromatic carbocyclic or heterocyclic ring, optionally including one or two ring members independently selected from the group consisting of C(=O), S(O) and $S(O)_2$, and optionally substituted with 1 to 4 substituents independently selected from the group consisting of $C_1$-$C_2$ alkyl, halogen, CN, $NO_2$ and $C_1$-$C_2$ alkoxy;
$R^{4a}$ and $R^{4b}$ are each independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, SCN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylsulfonyloxy, $C_1$-$C_4$ haloalkylthio, $C_1$-$C_4$ haloalkylsulfinyl, $C_1$-$C_4$ haloalkylsulfonyl, $C_1$-$C_4$ haloalkylsulfonyloxy, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or
$R^{4a}$ and $R^{4b}$ are each independently phenyl, benzyl or phenoxy, each optionally substituted with 1 to 3 substituents independently selected from $R^{14}$;
$R^5$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_4$-$C_7$ haloalkylcycloalkyl, each substituted with 1 to 2 substituents independently selected from $R^{11}$; or $R^5$ is $OR^7$, $S(O)_pR^7$, $NR^8R^9$, $OS(O)_2R^{10}$, $NR^9S(O)_2R^{10}$, $C(S)NH_2$, $C(R^{13})=NOR^{13}$, $C_4$-$C_7$ halocycloalkylalkyl, $C_1$-$C_4$ alkylaminothiocarbonyl or $C_1$-$C_4$ dialkylaminothiocarbonyl;

each $R^6$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $C(O)NH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or each $R^6$ is independently a phenyl, benzyl, benzoyl, phenoxy, 5- or 6-membered heteroaromatic ring or an aromatic 8-, 9- or 10-membered fused heterobicyclic ring system, each ring optionally substituted with 1 to 3 $R^{14}$;

each $R^7$ is independently $C_1$-$C_6$ alkyl substituted with one $R^{12}$; or $C_2$-$C_6$ alkenyl, $C_2$-$C_6$ alkynyl, $C_3$-$C_6$ cycloalkyl, $C_4$-$C_7$ cycloalkylalkyl, $C_4$-$C_7$ alkylcycloalkyl, $C_2$-$C_6$ haloalkenyl, $C_2$-$C_6$ haloalkynyl, $C_3$-$C_6$ halocycloalkyl, $C_4$-$C_7$ haloalkylcycloalkyl, $C_4$-$C_7$ halocycloalkylalkyl or $C_2$-$C_6$ haloalkylcarbonyl, each optionally substituted with one $R^{12}$;

$R^8$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_4$-$C_7$ haloalkylcycloalkyl or $C_2$-$C_6$ haloalkylcarbonyl, each substituted with one $R^{12}$;

$R^9$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_4$-$C_7$ haloalkylcycloalkyl, each optionally substituted with one $R^{12}$;

$R^{10}$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_4$-$C_7$ haloalkylcycloalkyl, each optionally substituted with one $R^{12}$;

each $R^{11}$ is independently $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $C_2$-$C_4$ alkoxycarbonyl;

each $R^{12}$ is independently $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN, $NO_2$, $C_2$-$C_4$ alkoxycarbonyl, $C_1$-$C_6$ alkylamino or $C_2$-$C_6$ dialkylamino; or each $R^{12}$ is independently a phenyl or a 5- or 6-membered heteroaromatic ring, each ring optionally substituted with 1 to 3 substituents independently selected from $R^{14}$;

each $R^{13}$ is independently H, $C_1$-$C_4$ alkyl or $C_1$-$C_4$ haloalkyl;

each $R^{14}$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

n is 0, 1, 2, 3 or 4; and p is 0, 1 or 2.

This invention also provides a composition for controlling an invertebrate pest comprising a biologically effective amount of a compound of Formula I, an N-oxide or an agronomic or nonagronomic suitable salt thereof; and at least one additional component selected from the group consisting of a surfactant, a solid diluent and a liquid diluent, said composition optionally further comprising an effective amount of at least one additional biologically active compound or agent.

This invention also provides a method for controlling an invertebrate pest comprising contacting the invertebrate pest or its environment with a biologically effective amount of a compound of Formula I, its N-oxide or an agronomic or nonagronomic suitable salt thereof, or with a composition comprising a compound of Formula I, an N-oxide or an agronomic or nonagronomic suitable salt thereof, and at least one additional component selected from the group consisting of a surfactant, a solid diluent, and a liquid diluent, said composition optionally further comprising an effective amount of at least one additional biologically active compound or agent.

This invention further provides a spray composition comprising a compound of Formula I, an N-oxide, or an agronomic or nonagronomic suitable salt thereof or the composition described above; and a propellant. This invention also provides a bait composition comprising a compound of Formula I, an N-oxide or suitable salt thereof; one or more food materials; optionally an attractant; and optionally a humectant. This invention further provides a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl isomers. Examples of "alkylsulfonyloxy" include $CH_3S(O)_2O$, $CH_3CH_2S(O)_2O$, $CH_3CH_2CH_2S(O)_2O$, $(CH_3)_2CHS(O)_2O$ and the different butylsulfonyloxy, pentylsulfonyloxy and hexylsulfonyloxy isomers. "Alkylamino", "dialkylamino", and the like, are defined analogously to the above examples. "Cycloalkyl" includes, for example, cyclopropyl, cyclobutyl, cyclopentyl and cyclohexyl. "Alkylcycloalkyl" includes, for example, methylcyclopropyl, ethylcyclobutyl and methylcyclohexyl. The term "cycloalkylamino" includes the same groups linked through a nitrogen atom such as cyclopentylamino and cyclohexylamino. "Trialkylsilyl" includes 3 branched or straight-chain alkyl attached to and linked through a silicon atom such as trimethylsilyl, trimethylsilyl and t-butyl-dimethylsilyl.

"Aromatic" indicates that each of ring atoms is essentially in the same plane and has a p-orbital perpendicular to the ring plane, and in which (4n+2) π electrons, when n is 0 or a positive integer, are associated with the ring to comply with Hückel's rule. The term "nonaromatic carbocyclic ring or ring system" denotes fully saturated carbocycles as well as partially or fully unsaturated carbocycles where the Hückel rule is not satisfied by any of the rings in the ring system. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The term "heteroaromatic ring or ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", "halocycloalkyl" or "haloalkylcycloalkyl", said alkyl, cycloalkyl or alkylcycloalkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC≡CCHCl$, $CF_3C≡C$, $CCl_3C≡C$ and $FCH_2C≡CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "haloalkylsulfonyloxy" include $CF_3S(O)_2O$, $CCl_3S(O)_2O$, $CF_3CH_2S(O)_2O$ and $CF_3CF_2S(O)_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH3)C(=O)$. Examples of "alkylaminothiocarbonyl" include $CH_3NHC(=S)$, $CH_3CH_2NHC(=S)$, $CH_3CH_2CH_2NHC(=S)$, $(CH_3)_2CHNHC(=S)$ and the different butylamino- or pentylaminothiocarbonyl isomers. Examples of "dialkylaminothiocarbonyl" include $(CH_3)_2NC(=S)$, $(CH_3CH_2)_2NC(=S)$, $CH_3CH_2(CH_3)NC(=S)$, $CH_3CH_2CH_2(CH_3)NC(=S)$ and $(CH_3)_2CHN(CH3)C(=S)$.

The total number of carbon atoms in a substituent group is indicated by the "$C_i$-$C_j$" prefix where i and j are numbers from 1 to 8. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted with 1 to 5 substituents" and the like indicates that 1 to 5 of the available positions on the group may be substituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H.

Cheeseman and E. S. G. Werstiuk in *Advances in Heterocyclic Chemistry*, vol. 22, pp 390-392, A. R. Katritzky and A. J. Boulton, Eds., Academic Press.

Agronomic and nonagronomic suitable salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Agronomic and nonagronomic suitable salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

As noted above, $R^3$ can be (among others) $C_1$-$C_6$ alkyl, $C_2$-$C_6$ alkenyl, $C_2$-$C_6$ alkynyl, $C_3$-$C_6$ cycloalkyl, each optionally substituted with one to five substituents independently selected from the group consisting of a phenyl, phenoxy and 5- or 6-membered heteroaromatic ring, each ring optionally substituted with 1 to 3 substituents independently selected from $R^{14}$. Examples of such rings incorporated into said $R^3$ groups include the rings illustrated as U-1 through U-53 and U-85 in Exhibit 1. An example of phenyl optionally substituted with 1 to 3 substituents independently selected from $R^{14}$ is the ring illustrated as U-1 in Exhibit 1, wherein $R^v$ is $R^{14}$ and r is an integer from 0 to 3. An example of a phenoxy optionally substituted with 1 to 3 substituents independently selected from $R^{14}$ is illustrated as U-85 in Exhibit 1, wherein $R^v$ is $R^{14}$ and r is an integer from 0 to 3. Examples of 5- or 6-membered heteroaromatic rings optionally substituted with 1 to 3 substituents independently selected from $R^{14}$ include the rings U-2 through U-53 illustrated in Exhibit 1 wherein $R^v$ is $R^{14}$ and r is an integer from 0 to 3.

$R^v$ is attached to these rings through any available carbon or nitrogen by replacement of a hydrogen on said carbon or nitrogen. Note that some U groups can only be substituted with less than 3 $R^v$ groups (e.g. U-16 through U-21 and U-32 through U-34 can only be substituted with one $R^v$). Note that when the attachment point between $(R^v)_r$ and the U group is illustrated as floating, $(R^v)_r$ can be attached to any available carbon or nitrogen of the U group. Note that when the attachment point on the U group is illustrated as floating, the U group can be attached to the remainder of Formula I through any available carbon or nitrogen of the U group by replacement of a hydrogen atom.

Exhibit 1

-continued
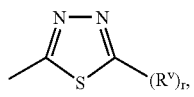 U-17
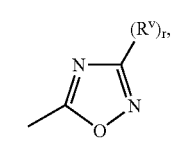 U-18
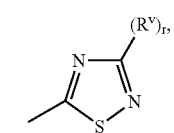 U-19
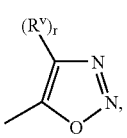 U-20
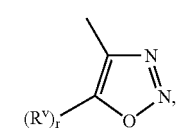 U-21
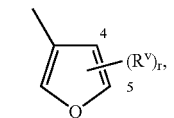 U-22
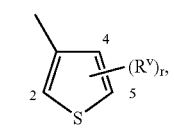 U-23
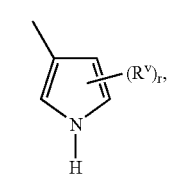 U-24
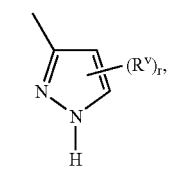 U-25
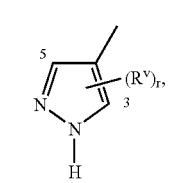 U-26
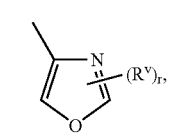 U-27
-continued
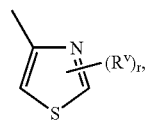 U-28
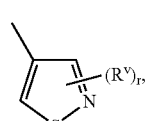 U-29
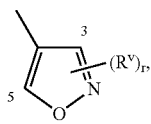 U-30
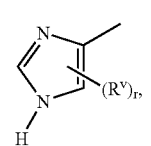 U-31
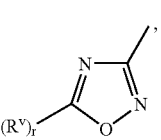 U-32
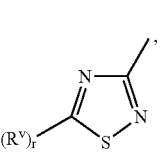 U-33
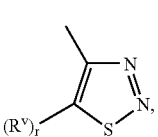 U-34
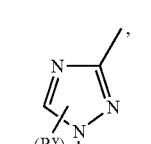 U-35
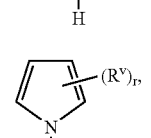 U-36
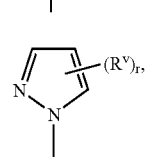 U-37
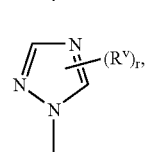 U-38

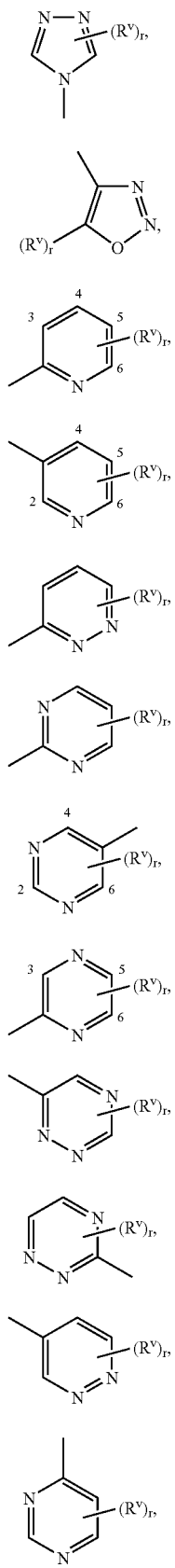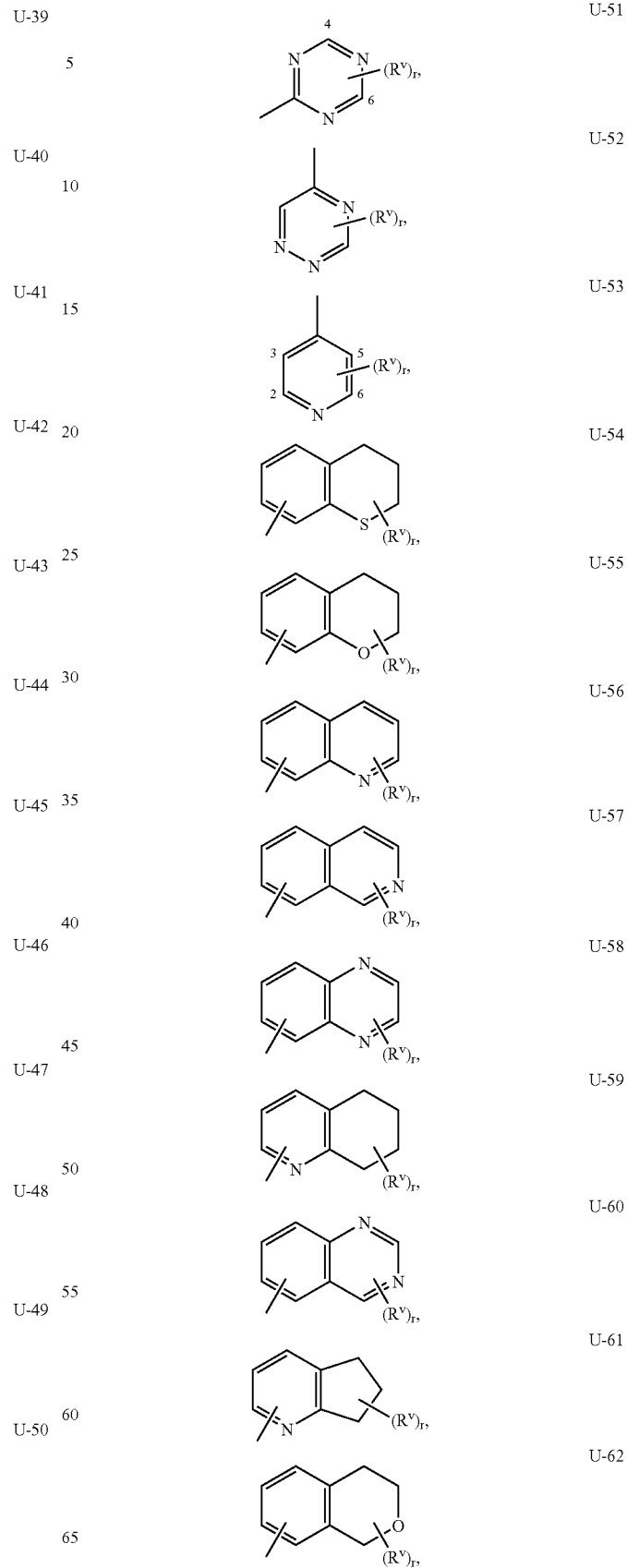

| | |
|---|---|
| 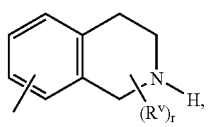 | U-63 |
| 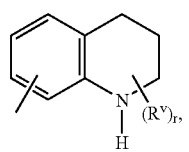 | U-64 |
| 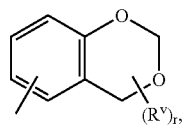 | U-65 |
| 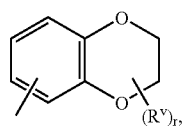 | U-66 |
| 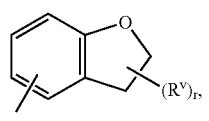 | U-67 |
| 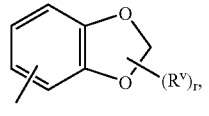 | U-68 |
| 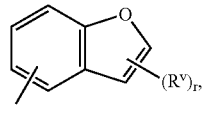 | U-69 |
| 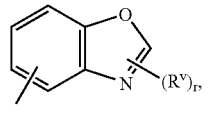 | U-70 |
| 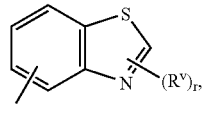 | U-71 |
| 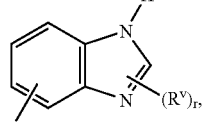 | U-72 |
| 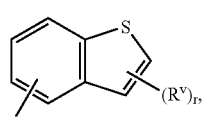 | U-73 |
| 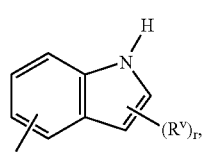 | U-74 |
| 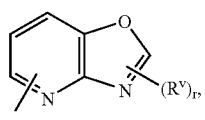 | U-75 |
| 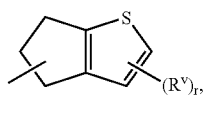 | U-76 |
| 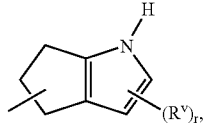 | U-77 |
| 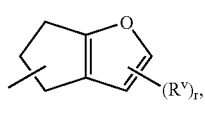 | U-78 |
| 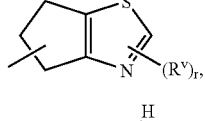 | U-79 |
| 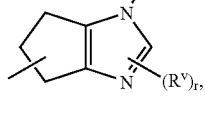 | U-80 |
| 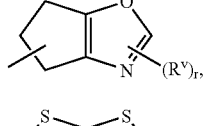 | U-81 |
| 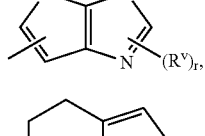 | U-82 |
| 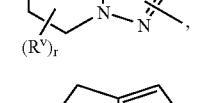 | U-83 |
| 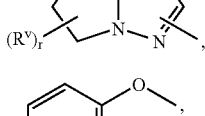 | U-84 |
| 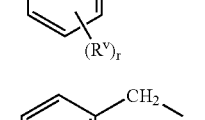 | U-85 |
| 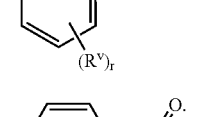 | U-86 |
| 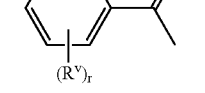 | U-87 |

As noted above, $R^3$ can be (among others) G; or $C_1$-$C_6$ alkyl, $C_2$-$C_6$ alkenyl, $C_2$-$C_6$ alkynyl, $C_3$-$C_6$ cycloalkyl, each optionally substituted with G; wherein G is a 5- or 6-membered nonaromatic carbocyclic or heterocyclic ring, optionally including one or two ring members independently selected from the group consisting of C(=O), S(O) or S(O)$_2$ and optionally substituted with 1 to 4 substituents independently selected from the group consisting of $C_1$-$C_2$ alkyl, halogen, CN, NO$_2$ and $C_1$-$C_2$ alkoxy. The term "optionally substituted" in connection with these G groups refers to groups which are unsubstituted or have at least one non-hydrogen substituent that does not extinguish the biological activity possessed by the unsubstituted analog. The optional substituents can be attached to any available carbon by replacing a hydrogen atom. Examples of 5- or 6-membered nonaromatic carbocyclic rings as G include the rings illustrated as G-1 through G-8 of Exhibit 2. Examples of 5- or 6-membered nonaromatic heterocyclic rings as G include the rings illustrated as G-9 through G-38 of Exhibit 2. Note that when G comprises a ring selected from G-31 through G-34, G-37 and G-38, $Q^1$ is selected from O, S or N. Note that when G is G-11, G13, G-14, G16, G-23, G-24, G-30 through G-34, G-37 and G-38 and $Q^1$ is N, the nitrogen atom can complete its valence by substitution with either H or $C_1$-$C_2$ alkyl. Note that when the attachment point on the G group is illustrated as floating, the G group can be attached to the remainder of Formula I through any available carbon of the G group by replacement of a hydrogen atom.

Exhibit 2

G-1
G-2
G-3
G-4
G-5
G-6
G-7

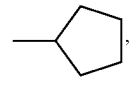

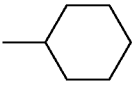

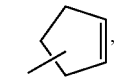

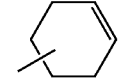

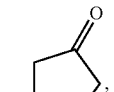

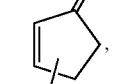

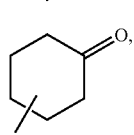

-continued

G-8
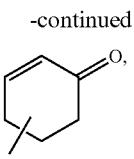

G-9
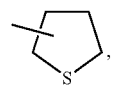

G-10
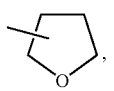

G-11
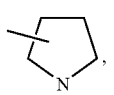

G-12
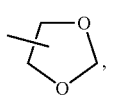

G-13
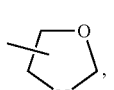

G-14
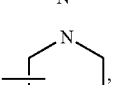

G-15
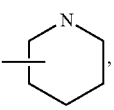

G-16
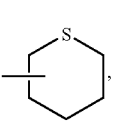

G-17
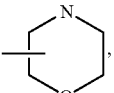

G-18
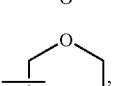

G-19
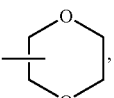

G-20
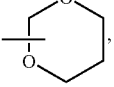

G-21
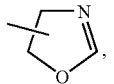

G-22
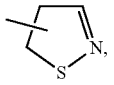

-continued

G-23 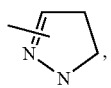

G-24 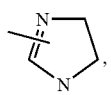

G-25 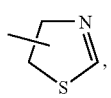

G-26 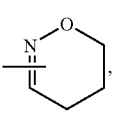

G-27 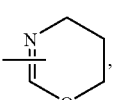

G-28 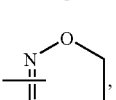

G-29 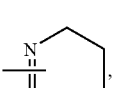

G-30 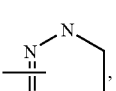

G-31 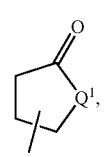

G-32 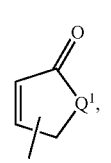

G-33 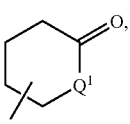

G-34 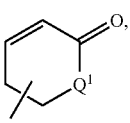

G-35 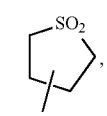

-continued

G-36 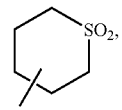

G-37 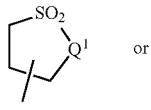 or

G-38 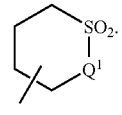

As noted above, each $R^6$ can be independently (among others) a phenyl, benzyl, phenoxy, 5- or 6-membered heteroaromatic ring or an aromatic 8-, 9- or 10-membered fused heterobicyclic ring system, each ring optionally substituted with 1 to 3 substituents independently selected from $R^{14}$. Examples of such $R^6$ groups include the rings or ring systems illustrated as U-1 through U-84, U-86 and U-87 illustrated in Exhibit 1, except that such rings are optionally substituted with 1 to 3 substituents independently selected from $R^{14}$ rather than $(R^v)_r$. Examples of aromatic 8-, 9- or 10-membered fused heterobicyclic ring systems optionally substituted with 1 to 3 substituents independently selected from $R^{14}$ include U-54 through U-84 illustrated in Exhibit 1 wherein $R^v$ is $R^{14}$ of Formula I and r is an integer from 0 to 3.

Of note is a compound of Formula I, its N-oxides and agronomic and nonagronomic suitable salts thereof, wherein $R^{4a}$ and $R^{4b}$ are each independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylsulfonyloxy, $C_1$-$C_4$ haloalkylthio, $C_1$-$C_4$ haloalkylsulfinyl, $C_1$-$C_4$ haloalkylsulfonyl, $C_1$-$C_4$ haloalkylsulfonyloxy, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $R^{4a}$ and $R^{4b}$ are each independently phenyl, benzyl or phenoxy, each optionally substituted with 1 to 3 substituents independently selected from $R^{14}$; and $R^5$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_4$-$C_7$ haloalkylcycloalkyl, each substituted with 1 to 2 substituents independently selected from $R^{11}$; or $R^5$ is $OR^7$, $S(O)_pR^7$, $NR^8R^9$, $OS(O)_2R^{10}$, $NR^9S(O)_2R^{10}$, $C(S)NH_2$, $C_4$-$C_7$ halocycloalkylalkyl, $C_1$-$C_4$ alkylaminothiocarbonyl or $C_1$-$C_4$ dialkylaminothiocarbonyl.

Preferred compounds for reasons of better activity and/or ease of synthesis are:

Preferred 1. Compounds of Formula I above, N-oxides or agronomic or nonagronomic suitable salts thereof, wherein $R^1$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl;

$R^2$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl;

$R^3$ is $C_1$-$C_6$ alkyl, $C_2$-$C_6$ alkenyl, $C_2$-$C_6$ alkynyl or $C_3$-$C_6$ cycloalkyl, each optionally substituted with 1 to 5 substituents independently selected from the group consisting of halogen, CN, $C_1$-$C_2$ alkoxy, $C_1$-$C_2$ alkylthio, $C_1$-$C_2$ alkylsulfinyl and $C_1$-$C_2$ alkylsulfonyl;

$R^{4a}$ and $R^{4b}$ are each independently H, $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl;

each $R^6$ is independently $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; and n is 0, 1 or 2.

Preferred 2. Compounds of Preferred 1 wherein
Y and V are each independently N or CH;
W is N, CH, CF, CCl, CBr or CI;
$R^1$ is H;
$R^2$ is H or $CH_3$;
$R^3$ is $C_1$-$C_4$ alkyl optionally substituted with 1 to 5 substituents independently selected from the group consisting of halogen, CN, $OCH_3$ and $S(O)_pCH_3$;
$R^{4a}$ and $R^{4b}$ are each independently H, $CH_3$, $CF_3$, $OCF_3$, $OCHF_2$, $S(O)_pCF_3$, $S(O)_pCHF_2$, CN or halogen;
each $R^6$ is independently halogen, CN, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$; and
n is 0 or 1.

Preferred 3. Compounds of Preferred 2 wherein
W is N;
$R^{4a}$ and $R^{4b}$ are each independently H, $CH_3$, $CF_3$, CN or halogen.

Preferred 4. Compounds of Preferred 3 wherein
$R^3$ is $C_1$-$C_4$ alkyl;
$R^{4a}$ is H, $CH_3$, Cl, Br or I;
$R^{4b}$ is H, F, Cl, Br, I, CN or $CF_3$;
$R^5$ is $OS(O)_2CH_3$, $OS(O)_2CF_3$, $CF_2O(C_1$-$C_4$ alkyl), $CF_2S(C_1$-$C_4$ alkyl) or $C_3$-$C_4$ haloalkenyloxy; and
$R^6$ is $CH_3$, $CF_3$, $OCH_2CF_3$, $OCHF_2$ or halogen at position 2.

Preferred 5. Compounds of Preferred 3 wherein
$R^3$ is $C_1$-$C_4$ alkyl;
$R^{4a}$ is H, $CH_3$, Cl, Br or I;
$R^{4b}$ is H, F, Cl, Br, I, CN or $CF_3$; and
$R^5$ is $C_2$-$C_6$ alkenyloxy, $C_2$-$C_6$ alkynyloxy, $C_1$-$C_6$ alkoxy substituted with CN or $C_1$-$C_2$ alkoxy.

Preferred 6. Compounds of Preferred 3 wherein
$R^3$ is $C_1$-$C_4$ alkyl;
$R^{4a}$ is H, $CH_3$, Cl, Br or I;
$R^{4b}$ is H, F, Cl, Br, I, CN or $CF_3$; and
$R^5$ is $C(R^{13})$=$NOR^{13}$.

This invention also provides a composition for controlling an invertebrate pest comprising a biologically effective amount of a compound of Formula I, an N-oxide thereof or an agronomic or nonagronomic suitable salt thereof and at least one additional component selected from the group consisting of a surfactant, a solid diluent and a liquid diluent, said composition optionally further comprising an effective amount of at least one additional biologically active compound or agent. The preferred compositions of the present invention are those which comprise the above preferred compounds.

This invention also provides a method for controlling an invertebrate pest comprising contacting the invertebrate pest or its environment with a biologically effective amount of a compound of Formula I, an N-oxide thereof or an agronomic or nonagronomic suitable salt thereof or with a biologically effective amount of the present composition described herein. The preferred methods of use are those involving the above preferred compounds.

The compounds of Formula I can be prepared by one or more of the following methods and variations as described in Schemes 1-12. The definitions of Y, V, W, n and $R^2$ through $R^{10}$ in the compounds of Formulae 1-35 below are as defined above in the Summary of the Invention unless indicated otherwise.

Compounds of Formula I can be prepared by the reaction of benzoxazinones of Formula 2 with amines of Formula 3 as outlined in Scheme 1.

Scheme 1

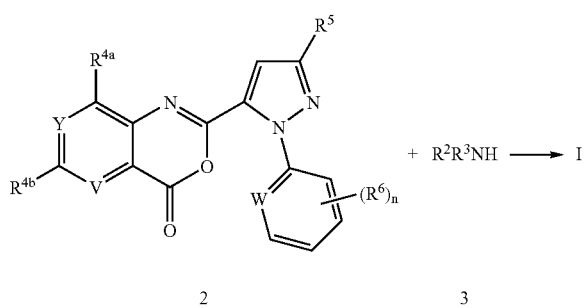

The reaction can be run neat or in a variety of suitable solvents including tetrahydrofuran, diethyl ether, dichloromethane and chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also G. M. Coppola, *J. Heterocyclic Chemistry* 1999, 36, 563-588.

Benzoxazinones of Formula 2 can be prepared by a variety of methods. Two methods that are especially useful are detailed in Schemes 2-3. In Scheme 2, a benzoxazinone of Formula 2 is prepared directly via coupling of a carboxylic acid of Formula 4 with an anthranilic acid of Formula 5.

Scheme 2

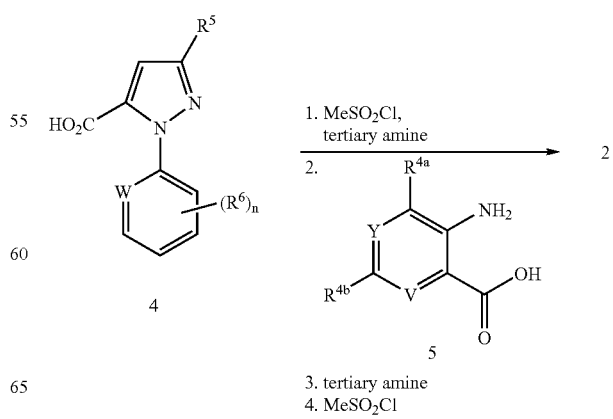

This involves sequential addition of methanesulfonyl chloride in the presence of a tertiary amine such as triethylamine or pyridine to a pyrazolecarboxylic acid of Formula 4, followed by the addition of an anthranilic acid of Formula 5, followed by a second addition of tertiary amine and methanesulfonyl chloride. This method generally affords good yields of the benzoxazinone and is illustrated with greater detail in Example 1.

Scheme 3 depicts an alternate preparation for benzoxazinones of Formula 2 involving coupling of an acid chloride of Formula 7 with an isatoic anhydride of Formula 6 to provide the benzoxazinone of Formula 2 directly.

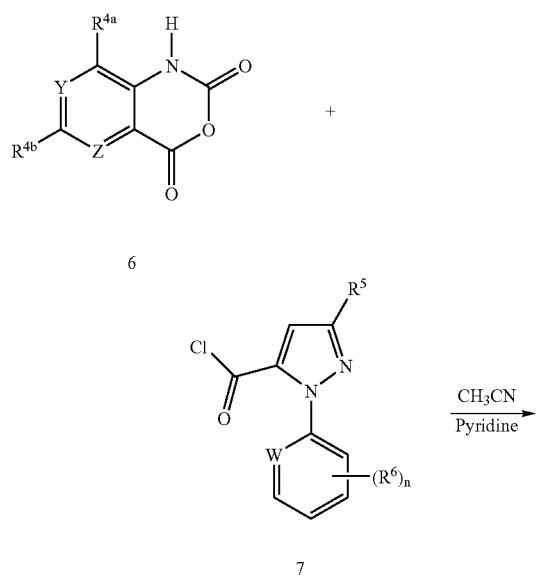

Solvents such as pyridine or pyridine/acetonitrile are suitable for this reaction. The acid chlorides of Formula 7 are available from the corresponding acids of Formula 4 by known methods such as chlorination with thionyl chloride or oxalyl chloride.

Anthranilic acids of Formula 5 are available by a variety of known methods. As shown in Scheme 4, anthranilic acids of Formula 5b containing an $R^{4b}$ substituent of chloro, bromo or iodo can be prepared by direct halogenation of an unsubstituted anthranilic acid of Formula 5a with N-chlorosuccinimide (NCS), N-bromosuccinimide (NBS) or N-iodosuccinimide (NIS) respectively in solvents such as N,N-dimethylformamide (DMF). The anthranilic acids of Formula 5b represent intermediates for a preferred set of compounds of Formula I.

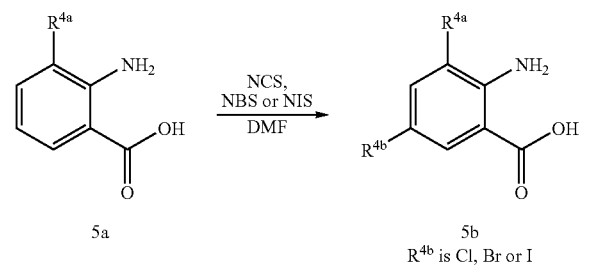

Preparation of the isatoic anhydrides of Formula 6 can be achieved from isatins of Formula 9 as outlined in Scheme 5.

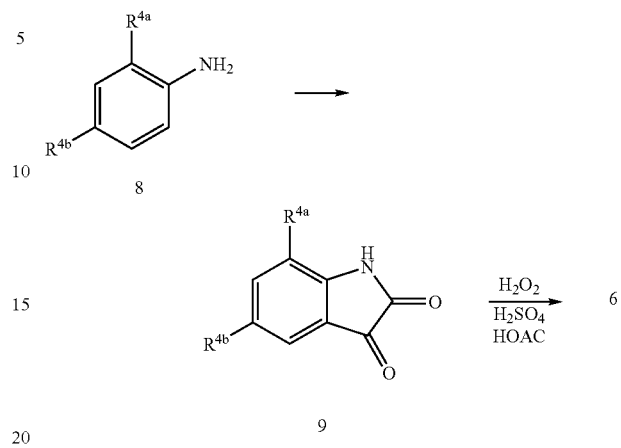

Isatins of Formula 9 are available from aniline derivatives of Formula 8 following literature procedures such as F. D. Popp, *Adv. Heterocycl. Chem.* 1975, 18, 1-58 and J. F. M. Da Silva et al., *Journal of the Brazilians Chemical Society* 2001, 12(3), 273-324. Oxidation of isatin 9 with hydrogen peroxide generally affords good yields of the corresponding isatoic anhydride 6 (G. Reissenweber and D. Mangold, *Angew. Chem. Int. Ed. Engl.* 1980, 19, 222-223). Isatoic anhydrides are also available from the anthranilic acids 5 via many known procedures involving reaction of 5 with phosgene or a phosgene equivalent.

Synthesis of a variety of heterocyclic acids of Formula 4 consisting of varied $R^5$ substituents is described in Schemes 6-12. Preferred compounds of the present invention are derived from pyrazole acids of Formula 4, substituted with a 3-chloropyridyl group. Therefore, for the purposes of illustration, the 3-chloropyridyl group is used as a representative example of substituted pyrazole acids in Schemes 6-12. Pyrazole acids 13, 17, 18, 24, 27, 30 and 35 thus represent a preferred set of pyrazole acids for the construction of Formula I compounds.

The synthesis of pyrazole acids of Formula 13, where $R^5$ is substituted alkyl, cycloalkyl or haloalkyl is depicted in Scheme 6. Pyrazoles of Formula 10 where $R^5$ is alkyl or cycloalkyl substituted with alkoxy or alkylthio are known compounds or can be prepared by known methods. Reaction of pyrazole 10 with 2,3-dichloropyridine 11 affords good yields of the 1-pyridylpyrazole of Formula 12 with good specificity for the desired regiochemistry. Metallation of a compound of Formula 12 with lithium diisopropylamide (LDA) followed by quenching of the lithium salt with carbon dioxide affords a pyrazole acid of Formula 13.

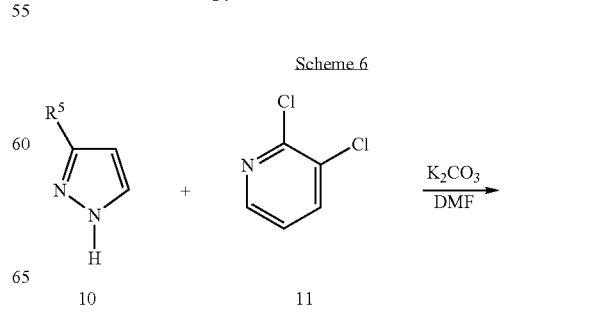

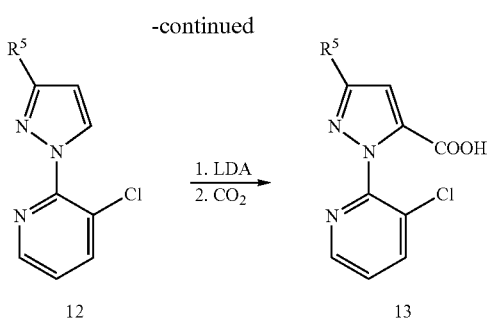

The synthesis of representative pyrazole acids of Formula 17, containing an OR[7] substituent, is depicted in Scheme 7. Reaction of pyridyl hydrazine 14 with diethyl maleate affords the 5-hydroxypyrazoline 15. Oxidation of compound 15 with a variety of oxidizing reagents including hydrogen peroxide, manganese dioxide and most preferably potassium persulfate affords the 5-hydroxypyrazole 16. Reaction of compound 16 with an alkylating reagent R[7]—X and hydrolysis of the ethyl ester function affords a pyrazole acid of Formula 17 containing many of the functionalized OR[7] groups of the present invention. In the alkylating reagent R[7]—X, X is a suitable leaving group such as halogen (e.g., Br, I), OS(O)$_2$CH$_3$ (methanesulfonate), OS(O)$_2$CF$_3$, OS(O)$_2$Ph-p-CH$_3$ (p-toluenesulfonate), and the like; methanesulfonate works well. The preparation of compound 16 and subsequent reaction with alkylating agents is provided in greater detail in Examples 1 and 2 respectively.

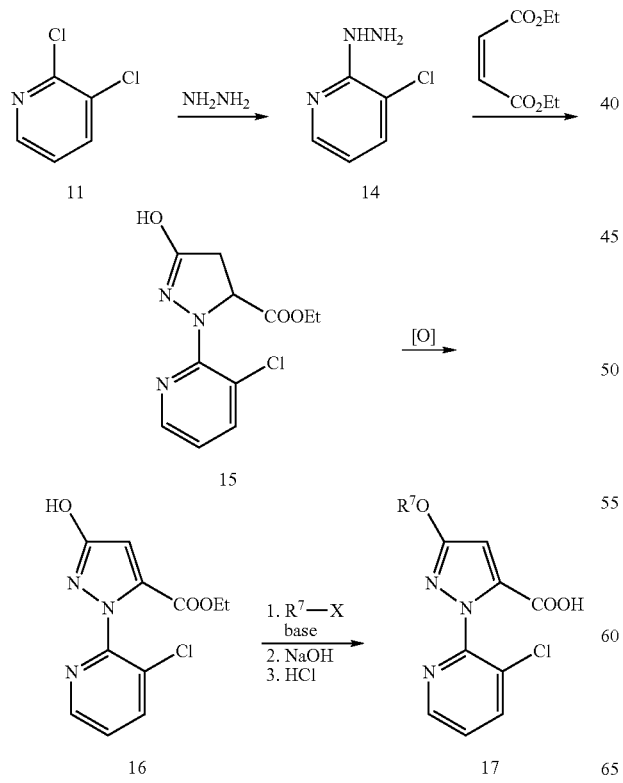

The synthesis of representative pyrazole acids of Formula 18, containing an OS(O)$_2$R[10] substituent, is depicted in Scheme 8. Reaction of pyridyl hydrazine 16 with a sulfonating reagent such as C$_1$-C$_6$ alkyl sulfonyl chlorides and C$_1$-C$_6$ alkyl sulfonic anhydrides followed by hydrolysis of the ester affords a pyrazole acid 18. The reaction of compound 16 with a sulfonating reagent is described in greater detail in Example 1.

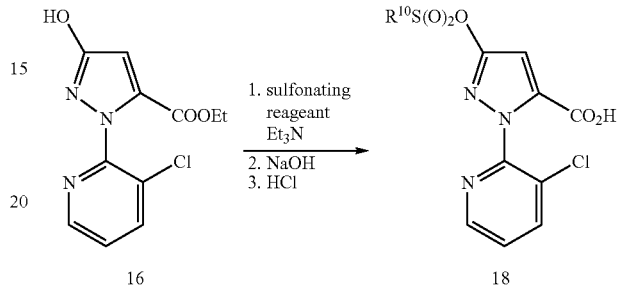

The synthesis of representative pyrazole acids of Formula 24 is depicted in Scheme 9. Compounds of Formula 21 can be prepared by a classical pyrazole synthesis involving the reaction of hydrazine with a substituted 1,3-diketone 20 (*J. Indian Chem. Soc.* 1985, 62(6), 465). Treatment of the pyrazole 21 with 2,3-dichloropyridine affords the pyridylpyrazole 22. Reaction of a compound of Formula 22 with nucleophiles such as sodium alkoxides or sodium thioalkoxides affords the pyridylpyrazole 23. Subsequent oxidation of 23 with a variety of oxidizing reagents such as potassium permanganate and sodium chlorite affords the pyrazole acid 24.

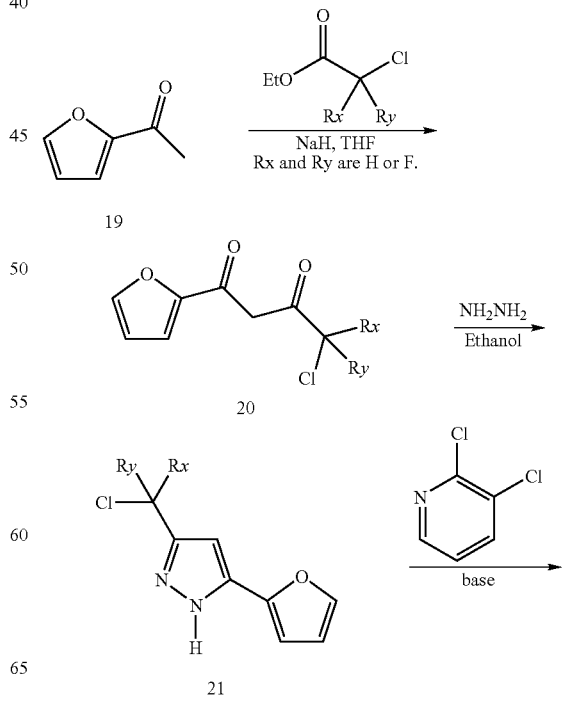

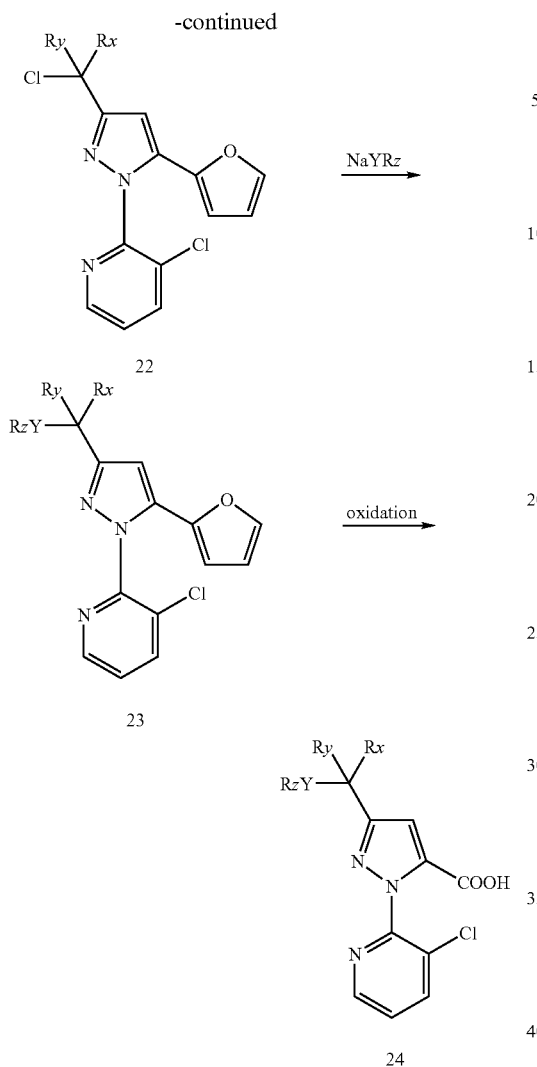

Y is O or S
Rz is alkyl or haloalkyl

The synthesis of representative pyrazole acids of Formula 27, containing a sulfonamide substituent at the 3-position of the pyrazole, is depicted in Scheme 10. Reaction of pyridyl hydrazine 14 with ethyl 2-cyanopyruvate affords the 5-aminopyrazoline 25. Reaction of compound 25 with sulfonating reagents such as $R^{10}S(O)_2Cl$ and $R^{10}S(O)_2OS(O)_2R^{10}$ affords pyrazoles 26. Compounds 26 can be hydrolyzed directly to the pyrazole acids 27 wherein $R^9$ is H. Compounds 26 can also be alkylated with alkylating reagents $R^9$—X (where X is defined above as in Scheme 7) followed by ester hydrolysis to afford compounds 27 wherein $R^9$ is other than hydrogen.

Scheme 10

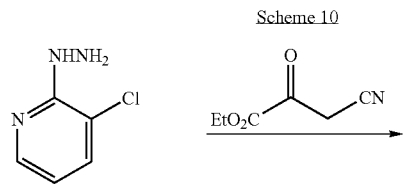

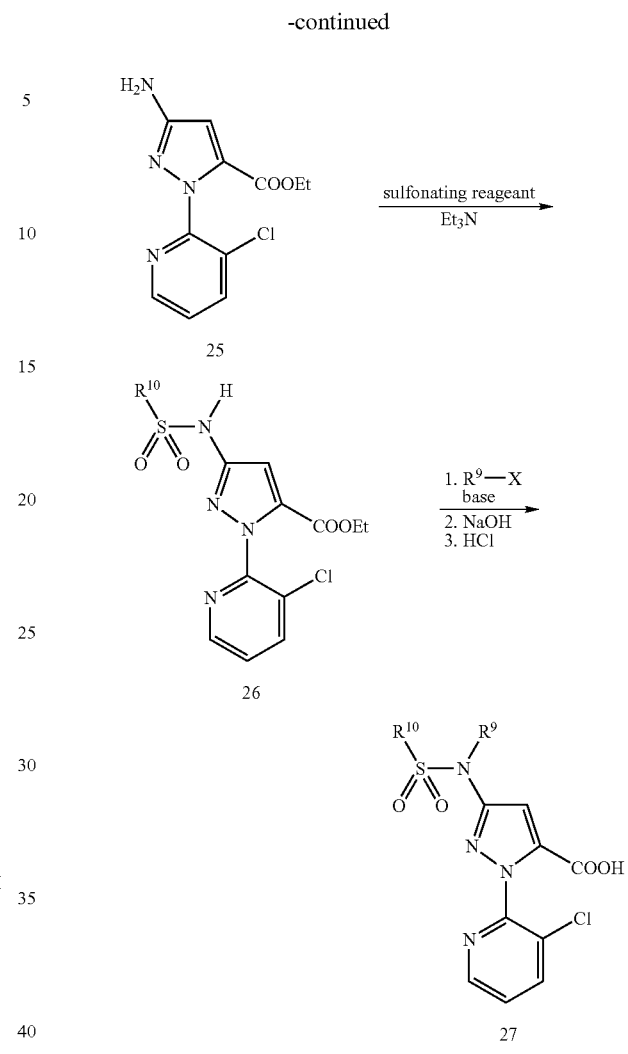

The synthesis of amino substituted pyrazole acids of Formula 30 is depicted in Scheme 11. Reaction of the 5-hydroxypyrazoline 15 with a chlorinating reagent such as phosphorus oxychloride affords the 5-chloropyrazoline 28. Reaction of 28 with amines of Formula $R^8R^9NH$ followed by oxidation affords the amino substituted pyrazole esters 29. Hydrolysis of compounds of Formula 29 affords the corresponding pyrazole acids of Formula 30.

Scheme 11

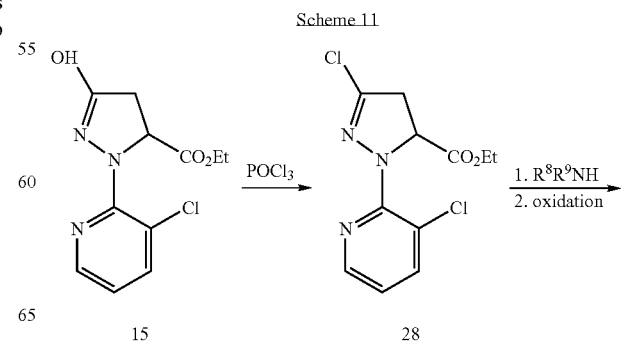

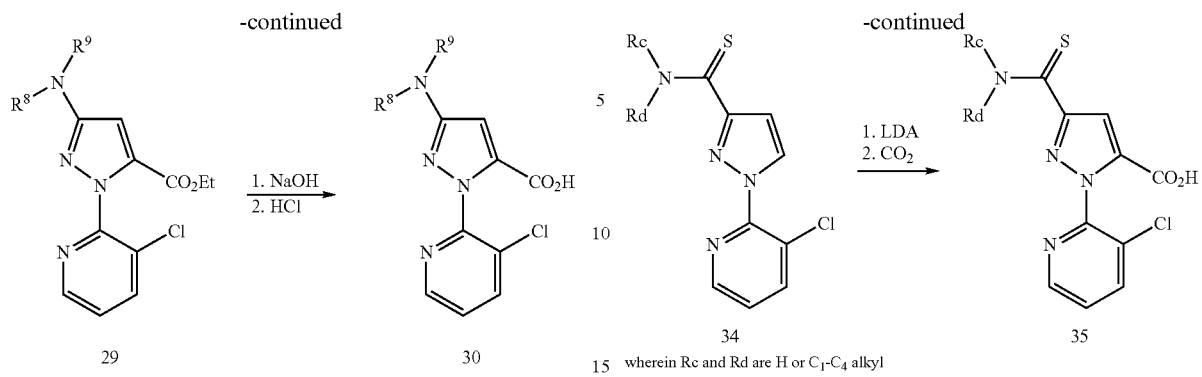

wherein Rc and Rd are H or $C_1$-$C_4$ alkyl

The synthesis of thioamide substituted pyrazole acids of Formula 35 is depicted in Scheme 12. Cyanopyrazole 31 is a known compound and can be prepared by methods described in WO 94/29300 and *J. Chem. Soc. C,* 1971, 11, 2147-2150. Reaction of 31 with 2,3-dichloropyridine 11 affords good yields of the 1-pyridylpyrazole 32 with good specificity for the desired regiochemistry. Hydrolysis of the nitrile followed by standard Schotten-Baumann procedures affords the corresponding amide 33. The amide may be converted to the thioamide utilizing a variety of thio transfer reagents including phosphorus pentasulfide and Lawesson's reagent to afford the thioamide 34. Metallation of compounds of Formula 34 with lithium diisopropylamide (LDA) and subsequent carbon dioxide quench affords the pyrazole acids of Formula 35.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, brs is broad singlet.

EXAMPLE 1

Preparation of 1-(3-Chloro-2-pyridinyl)-N-[2,4-dichloro-6-[(methylamino)carbonyl]phenyl]-3-[(methylsulfonyl)oxy]-1H-pyrazole-5-carboxamide Step A: Preparation of Ethyl 1-(3-chloro-2-pyridinyl)-3-pyrazolidinone-5-carboxylate A 2-L four-necked flask equipped with a mechanical stirrer, thermometer, addition funnel, reflux condenser, and nitrogen inlet was charged with absolute ethanol (250 mL) and an ethanolic solution of sodium ethoxide (21%, 190 mL, 0.504 mol). The mixture was heated to reflux at about 83° C. It was then treated with 3-chloro-2-hydrazinopyridine (68.0 g, 0.474 mol). The mixture was re-heated to reflux over a period of 5 minutes. The yellow slurry was then treated dropwise with diethyl maleate (88.0 mL, 0.544 mol) over a period of 5 minutes. The reflux rate increased markedly during the addition. By the end of the addition all of the starting material had dissolved. The resulting orange-red solution was held at reflux for 10 minutes. After being cooled to 65° C., the reaction mixture was treated with glacial acetic acid (50.0 mL, 0.873 mol). A precipitate formed. The mixture was diluted with water (650 mL), causing the precipitate to dissolve. The orange solution was cooled in an ice bath. Product began to precipitate at 28° C. The slurry was held at about 2° C. for 2 hours. The product was isolated via filtration, washed with aqueous ethanol (40%, 3×50 mL), then air-dried on the filter for about 1 hour. The title product compound was obtained as a highly crystalline, light orange powder (70.3 g, 55% yield). No significant impurities were observed by $^1$H NMR.

$^1$H NMR (DMSO-$d_6$) δ 1.22 (t, 3H), 2.35 (d, 1H), 2.91 (dd, 1H), 4.20 (q, 2H), 4.84 (d, 1H), 7.20 (dd, 1H), 7.92 (d, 1H), 8.27 (d, 1H), 10.18 (s, 1H).

Step B: Preparation of Ethyl 1-(3-chloro-2-pyridinyl)-2,3-dihydro-3-oxo-1H-pyrazole-5-carboxyate To a suspension of ethyl 1-(3-chloro-2-pyridinyl)-3-pyrazolidinone-5-carboxylate (i.e. the product of Step A) (27 g, 100 mmol) stirred in dry acetonitrile (200 mL) was added sulfuric acid (20 g, 200 mmol) in one portion. The reaction mixture thinned to form a pale green, nearly clear solution before thickening again to form a pale yellow suspension. Potassium persulfate (33 g, 120 mmol) was added in one portion, and then the reaction mixture was heated at gentle reflux for 3.5 hours. After cooling using an ice bath, a precipitate of white solid was removed by filtration and discarded. Concentration of the acetonitrile mother liquor and then dilution with water (400 mL) was followed by extraction three times with ethyl ether (700 mL total). The ethyl ether phase was concentrated to a reduced volume (75 mL) from which precipitated an-off white solid (3.75 g), which was collected by filtration. The ether mother liquor was further concentrated to yield a second crop of an off-white precipitate (4.2 g), which was collected by filtration. Further precipitation of an off-white solid (4.5 g) from the aqueous phase yielded a combined total of 12.45 g of the title compound.

$^1$HNMR DMSO-$d_6$) δ 1.06 (t, 3H), 4.11 (q, 2H), 6.34 (s, 1H), 7.6 (t, 1H), 8.19 (d, 1H), 8.5 (d, 1H), 10.6 (s, 1H).

Step C: Preparation of 1-(3-Chloro-2-pyridinyl)-2,3-dihydro-3-oxo-1H-pyrazole-5-carboxylic acid To a stirred solution of ethyl 1-(3-chloro-2-pyridinyl)-2,3-dihydro-3-oxo-1H-pyrazole-5-carboxylate (i.e. the product of Step B) (1.0 g, 3.7 mmol) in methanol (15 mL) was added water (3 mL). An aqueous solution of sodium hydroxide (50%, 1.0 g, 12.5 mmol) was added dropwise, and the reaction mixture was stirred at room temperature for 3 hours, during which time the reaction mixture turned a clear yellow. Water (20 mL) was added and the reaction mixture was extracted with ethyl ether, which was discarded. The aqueous phase was acidified to pH 2 using concentrated hydrochloric acid and then extracted with ethyl acetate (50 mL). The ethyl acetate extract was washed with water (20 mL) and brine (20 mL), dried over magnesium sulfate and concentrated to give the title compound, isolated as a white solid (0.76 g).

$^1$H NMR (DMSO-$d_6$) δ 6.27 (s, 1H), 7.57 (q, 1H), 8.16 (d, 1H), 8.48 (d, 1H) 10.55 (brs, 1H), 13.7 (brs, 1H).

Step D: Preparation of 6,8-Dichloro-2-[1-(3-chloro-2-pyridinyl)-3-[(methylsulfonyl)oxy]-1H-pyrazol-5-yl]-4H-3,1-benzoxazin-4-one To a solution of methanesulfonyl chloride (0.14 mL, 1.75 mmol) in acetonitrile (10 mL) was added dropwise a mixture of 1-(3-chloro-2-pyridinyl)-2,3-dihydro-3-oxo-1H-pyrazole-5-carboxylic acid (i.e. the product of Step C) (0.4 g, 1.67 mmol) and triethylamine (0.23 mL, 1.67 mmol) in acetonitrile (3 mL) at 0-5° C. The reaction temperature was then maintained at about 0° C. throughout the addition. After stirring for 10 minutes, 3,5-dichloroanthranilic acid (Aldrich, 0.34 g, 1.67 mmol) was added and stirring was continued for an additional 5 minutes. A solution of triethylamine (0.47 mL, 3.33 mmol) in acetonitrile (3 mL) was then added dropwise, and the reaction mixture stirred 40 minutes, followed by the addition of methanesulfonyl chloride (0.14 mL, 1.75 mmol). The reaction mixture was then warmed to room temperature and stirred overnight. Approximately 50 mL of water was then added followed by extraction with ethyl acetate (3×30 mL). The combined ethyl acetate phase was washed with water (1×20 mL) followed by brine (1×20 mL), dried (MgSO$_4$) and concentrated to yield 0.8 g of a crude yellow solid. Chromatography on silica gel using hexanes/ethyl acetate as eluent resulted in isolation of 0.11 g of the title compound as a yellow solid.

$^1$H NMR (CDCl$_3$) δ 3.35 (s, 3H), 7.14 (s, 1H), 7.50 (m, 1H), 7.72 (s, 1H), 7.99 (d, 1H), 8.05 (s, 1H), 8.55 (d, 1H).

Step E: Preparation of 1-(3-Chloro-2-pyridinyl)-N-[2,4-dichloro-6-[(methylamino)carbonyl]phenyl]-3-[(methylsulfonyl)oxy]-1H-pyrazole-5-carboxamide To a solution of 6,8-dichloro-2-[1-(3-chloro-2-pyridinyl)-3-[(methylsulfonyl)oxy]-1H-pyrazol-5-yl]-4H-3,1-benzoxazin-4-one (i.e. the product of step D) (0.05 g, 0.10 mmol) in acetonitrile (3 mL) was added methylamine (2.0 M solution in THF, 0.5 mL, 1 mmol). The resulting solution was stirred at room temperature overnight. Thin layer chromatography showed the reaction to be incomplete. Methylamine (2.0 M solution in THF, 0.5 mL, 1 mmol) was added dropwise and the reaction stirred 1 hour at room temperature. Thin layer chromatography showed the reaction was complete. The reaction mixture was concentrated to dryness to yield 0.057 g of the title compound, a compound of present invention, as a white solid.

$^1$H NMR (CDCl$_3$) δ 2.84 (d, 3H), 3.34 (s, 3H), 6.58 (d,NH), 7.10 (s, 1H), 7.20 (s, 1H), 7.25 (s, 1H), 7.37 (q, 1H), 7.85 (d, 1H), 8.45 (d, 1H), 10.08 (brs,NH).

EXAMPLE 2

Preparation of 1-(3-Chloro-2-pyridinyl)-N-[2,4-dichloro-6-[[(1-methylethyl)amino]carbonyl]phenyl]-3-[(methylsulfonyl)oxy]-1H-pyrazole-5-carboxamide To a solution of 6,8-dichloro-2-[1-(3-chloro-2-pyridinyl)-3-[(methylsulfonyl)oxy]-1H-pyrazol-5-yl]-4H-3,1-benzoxazin-4-one (i.e. the product of Example 1, step D) (0.05 g, 0.10 mmol) in acetonitrile (3 mL) was added isopropylamine (0.5 mL, 5.87 mmol) dropwise. The resulting solution was stirred at room temperature overnight. The reaction was concentrated to dryness to yield 0.038 g of the title compound, a compound of present invention, as a white solid.

$^1$H NMR (DMSO-d$_6$) δ 1.02 (d, 6H), 3.57 (s, 3H), 3.88 (m, 1H), 7.32 (s, 1H), 7.44 (d, 1H), 7.62 (q, 1H), 7.83 (d, 1H), 8.15 (d, 1H), 8.25 (brs,NH), 8.45 (d, 1H), 10.55 (brs,NH).

EXAMPLE 3

Preparation of 1-(3-Chloro-2-pyridinyl)-N-[2,4-dichloro-6-[[(1-methylethyl)amino]carbonyl]phenyl]-3-(2-propynyloxy)-1H-pyrazole-5-carboxamide Step A: Preparation of Ethyl 1-(3-chloro-2-pyridinyl)-3-(2-propynyloxy)-1H-pyrazole-5-carboxylate To a solution of ethyl 1-(3-chloro-2-pyridinyl)-2,3-dihydro-3-oxo-1H-pyrazole-5-carboxyate (i.e. the product of Example 1, Step B) (0.5 g, 1.9 mmol) in acetonitrile (20 mL) was added potassium carbonate (0.6 g, 3.8 mmol) and propargyl bromide (1.0 mL, 9.4 mmol). The reaction mixture was heated at reflux for 15 minutes. The mixture was then cooled and treated with water and extracted with a 1:1 mixture of diethyl ether and ethyl acetate. The organic extracts were then washed with a saturated solution of sodium chloride and dried over magnesium sulfate. The extract was concentrated to dryness on a rotary evaporator and chromatographed on silica gel using hexane/ethyl acetate (7:3) as eluent to isolate the title compound (0.45 g, 95% purity) as a red oil.

$^1$HNMR (CDCl$_3$) δ 1.20 (t, 3H), 2.54 (t, 1H), 4.21 (q, 2H), 4.91 (d, 2H), 6.50 (s, 1H), 7.4 (dd, 1H), 7.9 (d, 1H), 8.5 (d, 1H).

Step B: Preparation of 1-(3-Chloro-2-pyridinyl)-3-(2-propynyloxy)-1H-pyrazole-5-carboxylic acid To a 50 mL flask containing ethyl 1-(3-chloro-2-pyridinyl)-3-(2-propynyloxy)-1H-pyrazole-5-carboxylate (i.e. the product of Step A) (0.45 g, 1.5 mmol) and 10 mL of methanol was added dropwise a mixture of 50% sodium hydroxide (0.7 g, 8.75 mmol) in water (4.0 mL). The mixture was heated to near reflux and then cooled to ambient temperature with stirring continued for 15 minutes. To this mixture was added a solution of 1 N HCl (9.0 mL) and the reaction mixture was concentrated on rotary evaporator to approximately 5 mL to precipitate a solid. The product was isolated via filtration, washed with water, and then air-dried on the filter to afford 0.31 g of the title compound as a white solid.

$^1$H NMR (CDCl$_3$) δ 2.54 (t, 1H), 2.75 (brs, 1H), 4.90 (d, 2H), 6.5 (s, 1H), 7.40 (dd, 1H), 7.90 (d, 1H), 8.50 (d, 1H).

Step C: Preparation of 6,8-Dichloro-2-[1-(3-chloro-2-pyridinyl)-3-(2-propnyloxy)-1H-pyrazol-5-yl]-4H-3,1-benzoxazin-4-one To a solution of methanesulfonyl chloride (0.085 mL, 1.11 mmol) in acetonitrile (5 mL) was added dropwise 1-(3-chloro-2-pyridinyl)-3-(2-propynyloxy)-1H-pyrazole-5-carboxylic acid (i.e. the product of Step B) (0.31 g, 1.11 mmol) and triethylamine (0.157 mL, 1.11 mmol) in acetonitrile (5 mL) at room temperature. After stirring 10 minutes at room temperature, 3,5-dichloroanthranilic acid (227 mg, 1.11 mmol) in acetonitrile (15 mL) was added dropwise. A solution of triethylamine (0.312 mL, 2.22 mmol) in acetonitrile (5 mL) was then added dropwise and the mixture was stirred for 2 hours at room temperature, and then methanesulfonyl chloride (0.085 mL, 1.11 mmol) was added and stirred at room temperature overnight. The reaction mixture was concentrated to dryness on a rotary evaporator and chromatographed on silica gel using hexane/ethyl acetate as eluent to give the title compound (230 mg) as a white solid.

$^1$H NMR (CDCl$_3$) δ 2.57 (t, 1H), 4.95 (d, 2H), 6.76 (s, 1H), 7.45 (s, 1H), 7.70 (s, 1H), 7.95 (d, 1H), 8.05 (d, 1H), 8.55 (d, 1H).

Step D: Preparation of 1-(3-Chloro-2-pyridinyl)-N-[2,4-dichloro-6-[[(1-methylethyl)amino]carbonyl] phenyl]-3-(2-propynyloxy)-1H-pyrazole-5-carboxamide To a solution of 6,8-dichloro-2-[1-(3-chloro-2-pyridinyl)-3-(2-propynyloxy)-1H-pyrazol-5-yl]-4H-3,1-benzoxazin-4-one (i.e. the product of Step C) (70 mg, 0.15 mmol) in tetrahydrofuran was added isopropylamine (0.04 mL, 0.47 mmol), and the reaction mixture was stirred at room temperature overnight. The tetrahydrofuran was evaporated under reduced pressure, and the residual solid was chromotographed on silica gel using hexane/ethyl acetate (7:3) as eluent to give the title compound as a white solid (17 mg), m p. 188-189° C.

$^1$H NMR (CDCl$_3$) δ 1.25 (d, 6H), 2.55 (t, 1H), 4.1 (m, 1H), 4.93 (d, 2H), 6.1 (bd, 1H), 6.65 (s, 1H), 7.35 (m, 2H), 7.4 (d, 1H), 7.81 (d, 1H), 8.45 (d, 1H), 9.58 (brs, 1H).

By the procedures described herein together with methods known in the art, the following compounds of Tables 1 to 5 can be prepared. The following abbreviations are used in the Tables: t is tertiary, s is secondary, i is iso, c is cyclo, Me is methyl, Et is ethyl, Pr is propyl, i-Pr is isopropyl, t-Bu is tertiary butyl, Ph is phenyl, OMe is methoxy, OEt is ethoxy, SMe is methylthio, SEt is ethylthio, CN is cyano, NO$_2$ is nitro, S(O)Me is methylsulfinyl, and S(O)$_2$Me is methylsulfonyl.

TABLE 1

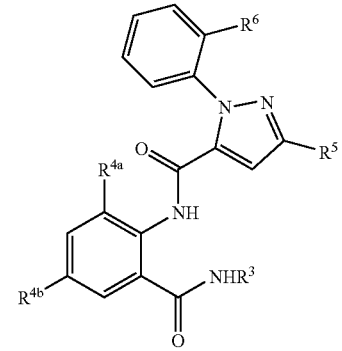

| R$^3$ | R$^{4a}$ | R$^{4b}$ | R$^5$ | R$^6$ |
|---|---|---|---|---|
| H | Me | H | CF$_2$OMe | Cl |
| Me | Me | H | CF$_2$OMe | Cl |
| Et | Me | H | CF$_2$OMe | Cl |
| i-Pr | Me | H | CF$_2$OMe | Cl |
| t-Bu | Me | H | CF$_2$OMe | Cl |
| c-Pr | Me | H | CF$_2$OMe | Cl |
| H | Me | H | CF$_2$OMe | F |
| Me | Me | H | CF$_2$OMe | F |
| Et | Me | H | CF$_2$OMe | F |
| i-Pr | Me | H | CF$_2$OMe | F |
| t-Bu | Me | H | CF$_2$OMe | F |
| c-Pr | Me | H | CF$_2$OMe | F |
| H | Cl | H | CF$_2$OMe | Cl |
| Me | Cl | H | CF$_2$OMe | Cl |
| Et | Cl | H | CF$_2$QMe | Cl |
| i-Pr | Cl | H | CF$_2$OMe | Cl |
| t-Bu | Cl | H | CF$_2$OMe | Cl |
| c-Pr | Cl | H | CF$_2$OMe | Cl |

TABLE 1-continued

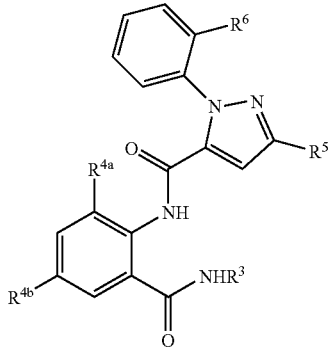

| R³ | R⁴ᵃ | R⁴ᵇ | R⁵ | R⁶ |
|---|---|---|---|---|
| H | Cl | H | CF₂OMe | F |
| Me | Cl | H | CF₂OMe | F |
| Et | Cl | H | CF₂OMe | F |
| i-Pr | Cl | H | CF₂OMe | F |
| t-Bu | Cl | H | CF₂OMe | F |
| c-Pr | Cl | H | CF₂OMe | F |
| H | Me | Cl | CF₂OMe | Cl |
| Me | Me | Cl | CF₂OMe | Cl |
| Et | Me | Cl | CF₂OMe | Cl |
| i-Pr | Me | Cl | CF₂OMe | Cl |
| t-Bu | Me | Cl | CF₂OMe | Cl |
| c-Pr | Me | Cl | CF₂OMe | Cl |
| H | Me | Cl | CF₂OMe | F |
| Me | Me | Cl | CF₂OMe | F |
| Et | Me | Cl | CF₂OMe | F |
| i-Pr | Me | Cl | CF₂OMe | F |
| t-Bu | Me | Cl | CF₂OMe | F |
| c-Pr | Me | Cl | CF₂OMe | F |
| Me | Me | Br | CF₂OMe | Cl |
| Et | Me | Br | CF₂OMe | Cl |
| i-Pr | Me | Br | CF₂OMe | Cl |
| t-Bu | Me | Br | CF₂OMe | Cl |
| c-Pr | Me | Br | CF₂OMe | Cl |
| H | Me | Br | CF₂OMe | F |
| Me | Me | Br | CF₂OMe | F |
| Et | Me | Br | CF₂OMe | F |
| i-Pr | Me | Br | CF₂OMe | F |
| t-Bu | Me | Br | CF₂OMe | F |
| c-Pr | Me | Br | CF₂OMe | F |
| H | Cl | Cl | CF₂OMe | Cl |
| Me | Cl | Cl | CF₂OMe | Cl |
| Et | Cl | Cl | CF₂OMe | Cl |
| i-Pr | Cl | Cl | CF₂OMe | Cl |
| t-Bu | Cl | Cl | CF₂OMe | Cl |
| c-Pr | Cl | Cl | CF₂OMe | Cl |
| H | Cl | Cl | CF₂OMe | F |
| Me | Cl | Cl | CF₂OMe | F |
| Et | Cl | Cl | CF₂OMe | F |
| i-Pr | Cl | Cl | CF₂OMe | F |
| t-Bu | Cl | Cl | CF₂OMe | F |
| c-Pr | Cl | Cl | CF₂OMe | F |
| H | Me | CN | CF₂OMe | Cl |
| Me | Me | CN | CF₂OMe | Cl |
| Et | Me | CN | CF₂OMe | Cl |
| i-Pr | Me | CN | CF₂OMe | Cl |
| t-Bu | Me | CN | CF₂OMe | Cl |
| c-Pr | Me | CN | CF₂OMe | Cl |
| H | Me | CN | CF₂OMe | F |
| Me | Me | CN | CF₂OMe | F |
| Et | Me | CN | CF₂OMe | F |
| i-Pr | Me | CN | CF₂OMe | F |
| t-Bu | Me | CN | CF₂OMe | F |
| c-Pr | Me | CN | CF₂OMe | F |
| H | Me | Cl | CF₂OMe | CF₃ |
| Me | Me | Cl | CF₂OMe | CF₃ |
| Et | Me | Cl | CF₂OMe | CF₃ |
| i-Pr | Me | Cl | CF₂OMe | CF₃ |
| t-Bu | Me | Cl | CF₂OMe | CF₃ |
| c-Pr | Me | Cl | CF₂OMe | CF₃ |

TABLE 1-continued

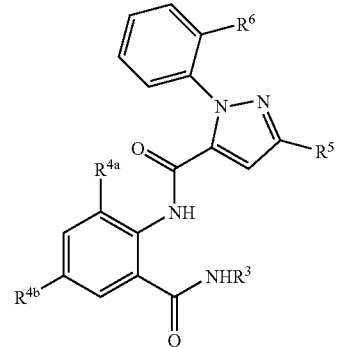

| R³ | R⁴ᵃ | R⁴ᵇ | R⁵ | R⁶ |
|---|---|---|---|---|
| H | Me | Cl | CF₂OMe | CN |
| Me | Me | Cl | CF₂OMe | CN |
| Et | Me | Cl | CF₂OMe | CN |
| i-Pr | Me | Cl | CF₂OMe | CN |
| t-Bu | Me | Cl | CF₂OMe | CN |
| c-Pr | Me | Cl | CF₂OMe | CN |
| H | Me | I | CF₂OMe | Cl |
| Me | Me | I | CF₂OMe | Cl |
| Et | Me | I | CF₂OMe | Cl |
| i-Pr | Me | I | CF₂OMe | Cl |
| t-Bu | Me | I | CF₂OMe | Cl |
| c-Pr | Me | I | CF₂OMe | Cl |
| H | Me | F | CF₂OMe | Cl |
| Me | Me | F | CF₂OMe | Cl |
| Et | Me | F | CF₂OMe | Cl |
| i-Pr | Me | F | CF₂OMe | Cl |
| t-Bu | Me | F | CF₂OMe | Cl |
| c-Pr | Me | F | CF₂OMe | Cl |
| H | Br | Cl | CF₂OMe | Cl |
| Me | Br | Cl | CF₂OMe | Cl |
| Et | Br | Cl | CF₂OMe | Cl |
| i-Pr | Br | Cl | CF₂OMe | Cl |
| t-Bu | Br | Cl | CF₂OMe | Cl |
| c-Pr | Br | Cl | CF₂OMe | Cl |
| H | Cl | Br | CF₂OMe | Cl |
| Me | Cl | Br | CF₂OMe | Cl |
| Et | Cl | Br | CF₂OMe | Cl |
| i-Pr | Cl | Br | CF₂OMe | Cl |
| t-Bu | Cl | Br | CF₂OMe | Cl |
| c-Pr | Cl | Br | CF₂OMe | Cl |
| H | Me | Cl | CF₂SMe | Cl |
| Me | Me | Cl | CF₂SMe | Cl |
| Et | Me | Cl | CF₂SMe | Cl |
| i-Pr | Me | Cl | CF₂SMe | Cl |
| t-Bu | Me | Cl | CF₂SMe | Cl |
| c-Pr | Me | Cl | CF₂SMe | Cl |
| H | Me | Cl | CF₂S(O)Me | Cl |
| Me | Me | Cl | CF₂S(O)Me | Cl |
| Et | Me | Cl | CF₂S(O)Me | Cl |
| i-Pr | Me | Cl | CF₂S(O)Me | Cl |
| t-Bu | Me | Cl | CF₂S(O)Me | Cl |
| c-Pr | Me | Cl | CF₂S(O)Me | Cl |
| H | Me | Cl | CF₂S(O)₂Me | Cl |
| Me | Me | Cl | CF₂S(O)₂Me | Cl |
| Et | Me | Cl | CF₂S(O)₂Me | Cl |
| i-Pr | Me | Cl | CF₂S(O)₂Me | Cl |
| t-Bu | Me | Cl | CF₂S(O)₂Me | Cl |
| c-Pr | Me | Cl | CF₂S(O)₂Me | Cl |
| H | Me | H | CH₂OMe | Cl |
| Me | Me | H | CH₂OMe | Cl |
| Et | Me | H | CH₂OMe | Cl |
| i-Pr | Me | H | CH₂OMe | Cl |
| t-Bu | Me | H | CH₂OMe | Cl |
| c-Pr | Me | H | CH₂OMe | Cl |
| H | Cl | H | CH₂OMe | Cl |
| Me | Cl | H | CH₂OMe | Cl |
| Et | Cl | H | CH₂OMe | Cl |
| i-Pr | Cl | H | CH₂OMe | Cl |
| t-Bu | Cl | H | CH₂OMe | Cl |

TABLE 1-continued

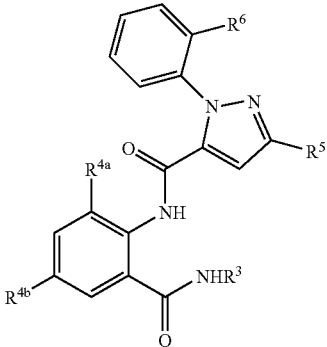

| R³ | R⁴ᵃ | R⁴ᵇ | R⁵ | R⁶ |
|---|---|---|---|---|
| c-Pr | Cl | H | CH₂OMe | Cl |
| H | Me | Cl | CH₂OMe | Cl |
| Me | Me | Cl | CH₂OMe | Cl |
| Et | Me | Cl | CH₂OMe | Cl |
| i-Pr | Me | Cl | CH₂OMe | Cl |
| t-Bu | Me | Cl | CH₂OMe | Cl |
| c-Pr | Me | Cl | CH₂OMe | Cl |
| H | Me | H | CH₂SMe | Cl |
| Me | Me | H | CH₂SMe | Cl |
| Et | Me | H | CH₂SMe | Cl |
| i-Pr | Me | H | CH₂SMe | Cl |
| t-Bu | Me | H | CH₂SMe | Cl |
| c-Pr | Me | H | CH₂SMe | Cl |
| H | Cl | H | CH₂SMe | Cl |
| Me | Cl | H | CH₂SMe | Cl |
| Et | Cl | H | CH₂SMe | Cl |
| i-Pr | Cl | H | CH₂SMe | Cl |
| t-Bu | Cl | H | CH₂SMe | Cl |
| c-Pr | Cl | H | CH₂SMe | Cl |
| H | Me | Cl | CH₂SMe | Cl |
| Me | Me | Cl | CH₂SMe | Cl |
| Et | Me | Cl | CH₂SMe | Cl |
| i-Pr | Me | Cl | CH₂SMe | Cl |
| t-Bu | Me | Cl | CH₂SMe | Cl |
| c-Pr | Me | Cl | CH₂SMe | Cl |
| H | Me | Cl | CH₂S(O)Me | Cl |
| Me | Me | Cl | CH₂S(O)Me | Cl |
| Et | Me | Cl | CH₂S(O)Me | Cl |
| i-Pr | Me | Cl | CH₂S(O)Me | Cl |
| t-Bu | Me | Cl | CH₂S(O)Me | Cl |
| c-Pr | Me | Cl | CH₂S(O)Me | Cl |
| H | Me | Cl | CH₂S(O)₂Me | Cl |
| Me | Me | Cl | CH₂S(O)₂Me | Cl |
| Et | Me | Cl | CH₂S(O)₂Me | Cl |
| i-Pr | Me | Cl | CH₂S(O)₂Me | Cl |
| t-Bu | Me | Cl | CH₂S(O)₂Me | Cl |
| c-Pr | Me | Cl | CH₂S(O)₂Me | Cl |
| H | Me | H | OS(O)₂Me | Cl |
| Me | Me | H | OS(O)₂Me | Cl |
| Et | Me | H | OS(O)₂Me | Cl |
| i-Pr | Me | H | OS(O)₂Me | Cl |
| t-Bu | Me | H | OS(O)₂Me | Cl |
| c-Pr | Me | H | OS(O)₂Me | Cl |
| H | Cl | H | OS(O)₂Me | Cl |
| Me | Cl | H | OS(O)₂Me | Cl |
| Et | Cl | H | OS(O)₂Me | Cl |
| i-Pr | Cl | H | OS(O)₂Me | Cl |
| t-Bu | Cl | H | OS(O)₂Me | Cl |
| c-Pr | Cl | H | OS(O)₂Me | Cl |
| H | Me | Cl | OS(O)₂Me | Cl |
| Me | Me | Cl | OS(O)₂Me | Cl |
| Et | Me | Cl | OS(O)₂Me | Cl |
| i-Pr | Me | Cl | OS(O)₂Me | Cl |
| t-Bu | Me | Cl | OS(O)₂Me | Cl |
| c-Pr | Me | Cl | OS(O)₂Me | Cl |
| H | Me | H | OS(O)₂CF₃ | Cl |
| Me | Me | H | OS(O)₂CF₃ | Cl |
| Et | Me | H | OS(O)₂CF₃ | Cl |
| i-Pr | Me | H | OS(O)₂CF₃ | Cl |

TABLE 1-continued

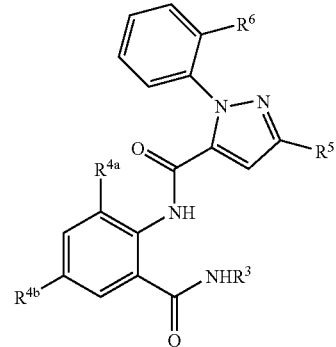

| R³ | R⁴ᵃ | R⁴ᵇ | R⁵ | R⁶ |
|---|---|---|---|---|
| t-Bu | Me | H | OS(O)₂CF₃ | Cl |
| c-Pr | Me | H | OS(O)₂CF₃ | Cl |
| H | Cl | H | OS(O)₂CF₃ | Cl |
| Me | Cl | H | OS(O)₂CP3 | Cl |
| Et | Cl | H | OS(O)₂CF₃ | Cl |
| i-Pr | Cl | H | OS(O)₂CF₃ | Cl |
| t-Bu | Cl | H | OS(O)₂CF₃ | Cl |
| c-Pr | Cl | H | OS(O)₂CF₃ | Cl |
| H | Me | Cl | OS(O)₂CClF₂ | Cl |
| Me | Me | Cl | OS(O)₂CClF₂ | Cl |
| Et | Me | Cl | OS(O)₂CClF₂ | Cl |
| i-Pr | Me | Cl | OS(O)₂CClF₂ | Cl |
| t-Bu | Me | Cl | OS(O)₂CClF₂ | Cl |
| c-Pr | Me | Cl | OS(O)₂CClF₂ | Cl |
| H | Me | Cl | OCH₂C≡CH | Cl |
| Me | Me | Cl | OCH₂C≡CH | Cl |
| Et | Me | Cl | OCH₂C≡CH | Cl |
| i-Pr | Me | Cl | OCH₂C≡CH | Cl |
| t-Bu | Me | Cl | OCH₂C≡CH | Cl |
| c-Pr | Me | Cl | OCH₂C≡CH | Cl |
| H | Me | Cl | OCH₂C≡CCF₃ | Cl |
| Me | Me | Cl | OCH₂C≡CCF₃ | Cl |
| Et | Me | Cl | OCH₂C≡CCF₃ | Cl |
| i-Pr | Me | Cl | OCH₂C≡CCF₃ | Cl |
| t-Bu | Me | Cl | OCH₂C≡CCF₃ | Cl |
| c-Pr | Me | Cl | OCH₂C≡CCF₃ | Cl |
| H | Me | Cl | OCH₂C≡CMe | Cl |
| Me | Me | Cl | OCH₂C≡CMe | Cl |
| Et | Me | Cl | OCH₂C≡CMe | Cl |
| i-Pr | Me | Cl | OCH₂C≡CMe | Cl |
| t-Bu | Me | Cl | OCH₂C≡CMe | Cl |
| c-Pr | Me | Cl | OCH₂C≡CMe | Cl |
| H | Me | Cl | OCH₂CH═CH₂ | Cl |
| Me | Me | Cl | OCH₂CH═CH₂ | Cl |
| Et | Me | Cl | OCH₂CH═CH₂ | Cl |
| i-Pr | Me | Cl | OCH₂CH═CH₂ | Cl |
| t-IBu | Me | Cl | OCH₂CH═CH₂ | Cl |
| c-Pr | Me | Cl | OCH₂CH═CH₂ | Cl |
| H | Me | Cl | NHMe | Cl |
| Me | Me | Cl | NHMe | Cl |
| Et | Me | Cl | NHMe | Cl |
| i-Pr | Me | Cl | NHMe | Cl |
| t-Bu | Me | Cl | NHMe | Cl |
| c-Pr | Me | Cl | NHMe | Cl |
| H | Me | Cl | NHCH₂CF₃ | Cl |
| Me | Me | Cl | NHCH₂CF₃ | Cl |
| Et | Me | Cl | NHCH₂CF₃ | Cl |
| i-Pr | Me | Cl | NHCH₂CF₃ | Cl |
| t-Bu | Me | Cl | NHCH₂CF₃ | Cl |
| c-Pr | Me | Cl | NHCH₂CF₃ | Cl |
| H | Me | Cl | OCH₂CCl═CH₂ | Cl |
| Me | Me | Cl | OCH₂CCl═CH₂ | Cl |
| Et | Me | Cl | OCH₂CCl═CH₂ | Cl |
| i-Pr | Me | Cl | OCH₂CCl═CH₂ | Cl |
| t-Bu | Me | Cl | OCH₂CCl═CH₂ | Cl |
| c-Pr | Me | Cl | OCH₂CCl═CH₂ | Cl |
| H | Me | Cl | OCH₂CH═CF₂ | Cl |
| Me | Me | Cl | OCH₂CH═CF₂ | Cl |
| Et | Me | Cl | OCH₂CH═CF₂ | Cl |

TABLE 1-continued

| R³ | R⁴ᵃ | R⁴ᵇ | R⁵ | R⁶ |
|---|---|---|---|---|
| i-Pr | Me | Cl | OCH₂CH=CF₂ | Cl |
| t-Bu | Me | Cl | OCH₂CH=CF₂ | Cl |
| c-Pr | Me | Cl | OCH₂CH=CF₂ | Cl |
| H | Me | Cl | OCH₂CCl=CHCl | Cl |
| Me | Me | Cl | OCH₂CCl=CHCl | Cl |
| Et | Me | Cl | OCH₂CCl=CHCl | Cl |
| i-Pr | Me | Cl | OCH₂CCl=CHCl | Cl |
| t-Bu | Me | Cl | OCH₂CCl=CHCl | Cl |
| c-Pr | Me | Cl | OCH₂CCl=CHCl | Cl |
| H | Me | Cl | NHS(O)₂CF₃ | Cl |
| Me | Me | Cl | NHS(O)₂CF₃ | Cl |
| Et | Me | Cl | NHS(O)₂CF₃ | Cl |
| i-Pr | Me | Cl | NHS(O)₂CF₃ | Cl |
| t-Bu | Me | Cl | NHS(O)₂CF₃ | Cl |
| c-Pr | Me | Cl | NHS(O)₂CF₃ | Cl |
| H | Me | Cl | NHCOCF₃ | Cl |
| Me | Me | Cl | NHCOCF₃ | Cl |
| Et | Me | Cl | NHCOCF₃ | Cl |
| i-Pr | Me | Cl | NHCOCF₃ | Cl |
| t-Bu | Me | Cl | NHCOCF₃ | Cl |
| c-Pr | Me | Cl | NHCOCF₃ | Cl |
| H | Me | Cl | SCH₂CCl=CH₂ | Cl |
| Me | Me | Cl | SCH₂CCl=CH₂ | Cl |
| Et | Me | Cl | SCH₂CCl=CH₂ | Cl |
| i-Pr | Me | Cl | SCH₂CCl=CH₂ | Cl |
| t-Bu | Me | Cl | SCH₂CCl=CH₂ | Cl |
| c-Pr | Me | Cl | SCH₂CCl=CH₂ | Cl |
| H | Me | Cl | OCH₂CN | Cl |
| Me | Me | Cl | OCH₂CN | Cl |
| Et | Me | Cl | OCH₂CN | Cl |
| i-Pr | Me | Cl | OCH₂CN | Cl |
| 1-Bu | Me | Cl | OCH₂CN | Cl |
| c-Pr | Me | Cl | OCH₂CN | Cl |
| H | Me | Cl | OCH₂NO₂ | Cl |
| Me | Me | Cl | OCH₂NO₂ | Cl |
| Et | Me | Cl | OCH₂NO₂ | Cl |
| i-Pr | Me | Cl | OCH₂NO₂ | Cl |
| t-Bu | Me | Cl | OCH₂NO₂ | Cl |
| c-Pr | Me | Cl | OCH₂NO₂ | Cl |
| H | Me | Cl | OCH₂NMe₂ | Cl |
| Me | Me | Cl | OCH₂NMe₂ | Cl |
| Et | Me | Cl | OCH₂NMe₂ | Cl |
| i-Pr | Me | Cl | OCH₂NMe₂ | Cl |
| t-Bu | Me | Cl | OCH₂NMe₂ | Cl |
| c-Pr | Me | Cl | OCH₂NMe₂ | Cl |
| H | Me | Cl | OCH₂NHMe | Cl |
| Me | Me | Cl | OCH₂NHMe | Cl |
| Et | Me | Cl | OCH₂NHMe | Cl |
| i-Pr | Me | Cl | OCH₂NHMe | Cl |
| t-Bu | Me | Cl | OCH₂NHMe | Cl |
| c-Pr | Me | Cl | OCH₂NHMe | Cl |
| H | Me | Cl | CSNH₂ | Cl |
| Me | Me | Cl | CSNH₂ | Cl |
| Et | Me | Cl | CSNH₂ | Cl |
| i-Pr | Me | Cl | CSNH₂ | Cl |
| t-Bu | Me | Cl | CSNH₂ | Cl |
| c-Pr | Me | Cl | CSNH₂ | Cl |
| H | Me | Cl | O-c-Pr | Cl |
| Me | Me | Cl | O-c-Pr | Cl |
| Et | Me | Cl | O-c-Pr | Cl |
| i-Pr | Me | Cl | O-c-Pr | Cl |
| t-Bu | Me | Cl | O-c-Pr | Cl |
| c-Pr | Me | Cl | O-c-Pr | Cl |
| H | Me | Cl | CH₂OCHF₂ | Cl |
| Me | Me | Cl | CH₂OCHF₂ | Cl |
| Et | Me | Cl | CH₂OCHF₂ | Cl |
| i-Pr | Me | Cl | CH₂OCHF₂ | Cl |
| t-Bu | Me | Cl | CH₂OCHF₂ | Cl |
| c-Pr | Me | Cl | CH₂OCHF₂ | Cl |
| H | Me | Cl | CH₂SCHF₂ | Cl |
| Me | Me | Cl | CH₂SCHF₂ | Cl |
| Et | Me | Cl | CH₂SCHF₂ | Cl |
| i-Pr | Me | Cl | CH₂SCHF₂ | Cl |
| t-Bu | Me | Cl | CH₂SCHF₂ | Cl |
| c-Pr | Me | Cl | CH₂SCHF₂ | Cl |
| H | Me | Cl | CH₂S(O)₂CHF₂ | Cl |
| Me | Me | Cl | CH₂S(O)₂CHF₂ | Cl |
| Et | Me | Cl | CH₂S(O)₂CHF₂ | Cl |
| i-Pr | Me | Cl | CH₂S(O)₂CHF₂ | Cl |
| t-Bu | Me | Cl | CH₂S(O)₂CHF₂ | Cl |
| c-Pr | Me | Cl | CH₂S(O)₂CHF₂ | Cl |
| H | Me | Cl | 2,2-di-F-c-Pr | Cl |
| Me | Me | Cl | 2,2-di-F-c-Pr | Cl |
| Et | Me | Cl | 2,2-di-F-c-Pr | Cl |
| i-Pr | Me | Cl | 2,2-di-F-c-Pr | Cl |
| t-Bu | Me | Cl | 2,2-di-F-c-Pr | Cl |
| c-Pr | Me | Cl | 2,2-di-F-c-Pr | Cl |
| H | Me | Cl | 2,2,3,3-tetra-F-c-Pr | Cl |
| Me | Me | Cl | 2,2,3,3-tetra-F-c-Pr | Cl |
| Et | Me | Cl | 2,2,3,3-tetra-F-c-Pr | Cl |
| i-Pr | Me | Cl | 2,2,3,3-tetra-F-c-Pr | Cl |
| t-Bu | Me | Cl | 2,2,3,3-tetra-F-c-Pr | Cl |
| c-Pr | Me | Cl | 2,2,3,3-tetra-F-c-Pr | Cl |
| H | Me | Cl | 2,2-di-F-c-PrCH₂ | Cl |
| Me | Me | Cl | 2,2-di-F-c-PrCH₂ | Cl |
| Et | Me | Cl | 2,2-di-F-c-PrCH₂ | Cl |
| i-Pr | Me | Cl | 2,2-di-F-c-PrCH₂ | Cl |
| t-Bu | Me | Cl | 2,2-di-F-c-PrCH₂ | Cl |
| c-Pr | Me | Cl | 2,2-di-F-c-PrCH₂ | Cl |
| H | Me | H | CF₂OEt | Cl |
| Me | Me | H | CF₂OEt | Cl |
| Et | Me | H | CF₂OEt | Cl |
| i-Pr | Me | H | CF₂OEt | Cl |
| t-Bu | Me | H | CF₂OEt | Cl |
| c-Pr | Me | H | CF₂OEt | Cl |
| H | Me | H | CF₂OEt | F |
| Me | Me | H | CF₂OEt | F |
| Et | Me | H | CF₂OEt | F |
| i-Pr | Me | H | CF₂OEt | F |
| t-Bu | Me | H | CF₂OEt | F |
| c-Pr | Me | H | CF₂OEt | F |
| H | Cl | H | CF₂OEt | Cl |
| Me | Cl | H | CF₂OEt | Cl |
| Et | Cl | H | CF₂OEt | Cl |
| i-Pr | Cl | H | CF₂OEt | Cl |
| t-Bu | Cl | H | CF₂OEt | Cl |
| c-Pr | Cl | H | CF₂OEt | Cl |
| H | Cl | H | CF₂OEt | F |

TABLE 1-continued

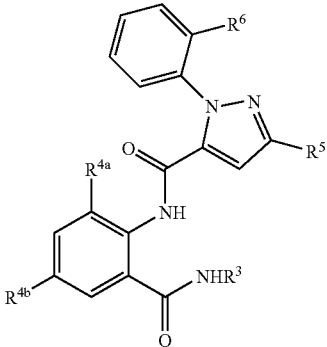

| R³ | R⁴ᵃ | R⁴ᵇ | R⁵ | R⁶ |
|---|---|---|---|---|
| Me | Cl | H | CF₂OEt | F |
| Et | Cl | H | CF₂OEt | F |
| i-Pr | Cl | H | CF₂OEt | F |
| t-Bu | Cl | H | CF₂OEt | F |
| c-Pr | Cl | H | CF₂OEt | F |
| H | Me | Cl | CF₂OEt | Cl |
| Me | Me | Cl | CF₂OEt | Cl |
| Et | Me | Cl | CF₂OEt | Cl |
| i-Pr | Me | Cl | CF₂OEt | Cl |
| t-Bu | Me | Cl | CF₂OEt | Cl |
| c-Pr | Me | Cl | CF₂OEt | Cl |
| H | Me | Cl | CF₂OEt | F |
| Me | Me | Cl | CF₂OEt | F |
| Et | Me | Cl | CF₂OEt | F |
| i-Pr | Me | Cl | CF₂OEt | F |
| t-Bu | Me | Cl | CF₂OEt | F |
| c-Pr | Me | Cl | CF₂OEt | F |
| Me | Me | Br | CF₂OEt | Cl |
| Et | Me | Br | CF₂OEt | Cl |
| i-Pr | Me | Br | CF₂OEt | Cl |
| t-Bu | Me | Br | CF₂OEt | Cl |
| c-Pr | Me | Br | CF₂OEt | Cl |
| H | Me | Br | CF₂OEt | F |
| Me | Me | Br | CF₂OEt | F |
| Et | Me | Br | CF₂OEt | F |
| i-Pr | Me | Br | CF₂OEt | F |
| t-Bu | Me | Br | CF₂OEt | F |
| c-Pr | Me | Br | CF₂OEt | F |
| H | Cl | Cl | CF₂OEt | Cl |
| Me | Cl | Cl | CF₂OEt | Cl |
| Et | Cl | Cl | CF₂OEt | Cl |
| i-Pr | Cl | Cl | CF₂OEt | Cl |
| t-Bu | Cl | Cl | CF₂OEt | Cl |
| c-Pr | Cl | Cl | CF₂OEt | Cl |
| H | Cl | Cl | CF₂OEt | F |
| Me | Cl | Cl | CF₂OEt | F |
| Et | Cl | Cl | CF₂OEt | F |
| i-Pr | Cl | Cl | CF₂OEt | F |
| t-Bu | Cl | Cl | CF₂OEt | F |
| c-Pr | Cl | Cl | CF₂OEt | F |
| H | Me | CN | CF₂OEt | Cl |
| Me | Me | CN | CF₂OEt | Cl |
| Et | Me | CN | CF₂OEt | Cl |
| i-Pr | Me | CN | CF₂OEt | Cl |
| t-Bu | Me | CN | CF₂OEt | Cl |
| c-Pr | Me | CN | CF₂OEt | Cl |
| H | Me | CN | CF₂OEt | F |
| Me | Me | CN | CF₂OEt | F |
| Et | Me | CN | CF₂OEt | F |
| i-Pr | Me | CN | CF₂OEt | F |
| t-Bu | Me | CN | CF₂OEt | F |
| c-Pr | Me | CN | CF₂OEt | F |
| H | Me | Cl | CF₂OEt | CF₃ |
| Me | Me | Cl | CF₂OEt | CF₃ |
| Et | Me | Cl | CF₂OEt | CF₃ |
| i-Pr | Me | Cl | CF₂OEt | CF₃ |
| t-Bu | Me | Cl | CF₂OEt | CF₃ |
| cPr | Me | Cl | CF₂OEt | CF₃ |
| H | Me | Cl | CF₂OEt | CN |

TABLE 1-continued

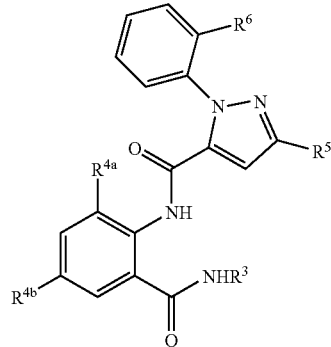

| R³ | R⁴ᵃ | R⁴ᵇ | R⁵ | R⁶ |
|---|---|---|---|---|
| Me | Me | Cl | CF₂OEt | CN |
| Et | Me | Cl | CF₂OEt | CN |
| i-Pr | Me | Cl | CF₂OEt | CN |
| t-Bu | Me | Cl | CF₂OEt | CN |
| c-Pr | Me | Cl | CF₂OEt | CN |
| H | Me | I | CF₂OEt | Cl |
| Me | Me | I | CF₂OEt | Cl |
| Et | Me | I | CF₂OEt | Cl |
| i-Pr | Me | I | CF₂OEt | Cl |
| t-Bu | Me | I | CF₂OEt | Cl |
| c-Pr | Me | I | CF₂OEt | Cl |
| H | Me | F | CF₂OEt | Cl |
| Me | Me | F | CF₂OEt | Cl |
| Et | Me | F | CF₂OEt | Cl |
| i-Pr | Me | F | CF₂OEt | Cl |
| t-Bu | Me | F | CF₂OEt | Cl |
| c-Pr | Me | F | CF₂OEt | Cl |
| H | Br | Cl | CF₂OEt | Cl |
| Me | Br | Cl | CF₂OEt | Cl |
| Et | Br | Cl | CF₂OEt | Cl |
| i-Pr | Br | Cl | CF₂OEt | Cl |
| t-Bu | Br | Cl | CF₂OEt | CL |
| c-Pr | Br | Cl | CF₂OEt | Cl |
| H | Cl | Br | CF₂OEt | Cl |
| Me | Cl | Br | CF₂OEt | Cl |
| Et | Cl | Br | CF₂OEt | Cl |
| i-Pr | Cl | Br | CF₂OEt | Cl |
| t-Bu | Cl | Br | CF₂OEt | Cl |
| c-Pr | Cl | Br | CF₂OEt | Cl |
| H | Me | Cl | CF₂SEt | Cl |
| Me | Me | Cl | CF₂SEt | Cl |
| Et | Me | Cl | CF₂SEt | Cl |
| i-Pr | Me | Cl | CF₂SEt | Cl |
| t-Bu | Me | Cl | CF₂SEt | Cl |
| c-Pr | Me | Cl | CF₂SEt | Cl |
| H | Me | Cl | CF₂S(O)Et | Cl |
| Me | Me | Cl | CF₂S(O)Et | Cl |
| Et | Me | Cl | CF₂S(O)Et | Cl |
| i-Pr | Me | Cl | CF₂S(O)Et | Cl |
| t-Bu | Me | Cl | CF₂S(O)Et | Cl |
| c-Pr | Me | Cl | CF₂S(O)Et | Cl |
| H | Me | Cl | CF₂S(O)₂Et | Cl |
| Me | Me | Cl | CF₂S(O)₂Et | Cl |
| Et | Me | Cl | CF₂S(O)₂Et | Cl |
| i-Pr | Me | Cl | CF₂S(O)₂Et | Cl |
| t-Bu | Me | Cl | CF₂S(O)₂Et | Cl |
| c-Pr | Me | Cl | CF₂S(O)₂Et | Cl |
| H | Me | H | CH₂OEt | Cl |
| Me | Me | H | CH₂OEt | Cl |
| Et | Me | H | CH₂OEt | Cl |
| i-Pr | Me | H | CH₂OEt | Cl |
| t-Bu | Me | H | CH₂OEt | Cl |
| c-Pr | Me | H | CH₂OEt | Cl |
| H | Cl | H | CH₂OEt | Cl |
| Me | Cl | H | CH₂OEt | Cl |
| Et | Cl | H | CH₂OEt | Cl |
| i-Pr | Cl | H | CH₂OEt | Cl |
| t-Bu | Cl | H | CH₂OEt | Cl |
| c-Pr | Cl | H | CH₂OEt | Cl |

TABLE 1-continued

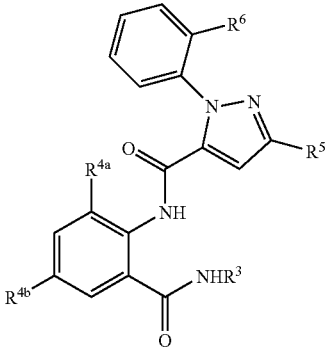

| R³ | R⁴ᵃ | R⁴ᵇ | R⁵ | R⁶ |
|---|---|---|---|---|
| H | Me | Cl | CH₂OEt | Cl |
| Me | Me | Cl | CH₂OEt | Cl |
| Et | Me | Cl | CH₂OEt | Cl |
| i-Pr | Me | Cl | CH₂OEt | Cl |
| t-Bu | Me | Cl | CH₂OEt | Cl |
| c-Pr | Me | Cl | CH₂OEt | Cl |
| H | Me | H | CH₂SEt | Cl |
| Me | Me | H | CH₂SEt | Cl |
| Et | Me | H | CH₂SEt | Cl |
| i-Pr | Me | H | CH₂SEt | Cl |
| t-Bu | Me | H | CH₂SEt | Cl |
| c-Pr | Me | H | CH₂SEt | Cl |
| H | Cl | H | CH₂SEt | Cl |
| Me | Cl | H | CH₂SEt | Cl |
| Et | Cl | H | CH₂SEt | Cl |
| i-Pr | Cl | H | CH₂SEt | Cl |
| t-Bu | Cl | H | CH₂SEt | Cl |
| c-Pr | Cl | H | CH₂SEt | Cl |
| H | Me | Cl | CH₂SEt | Cl |
| Me | Me | Cl | CH₂SEt | Cl |
| Et | Me | Cl | CH₂SEt | Cl |
| i-Pr | Me | Cl | CH₂SEt | Cl |
| t-Bu | Me | Cl | CH₂SEt | Cl |
| c-Pr | Me | Cl | CH₂SEt | Cl |
| H | Me | Cl | CH₂S(O)Et | Cl |
| Me | Me | Cl | CH₂S(O)Et | Cl |
| Et | Me | Cl | CH₂S(O)Et | Cl |
| i-Pr | Me | Cl | CH₂S(O)Et | Cl |
| t-Bu | Me | Cl | CH₂S(O)Et | Cl |
| c-Pr | Me | Cl | CH₂S(O)Et | Cl |
| H | Me | Cl | CH₂S(O)₂Et | Cl |
| Me | Me | Cl | CH₂S(O)₂Et | Cl |
| Et | Me | Cl | CH₂S(O)₂Et | Cl |
| i-Pr | Me | Cl | CH₂S(O)₂Et | Cl |
| t-Bu | Me | Cl | CH₂S(O)₂Et | Cl |
| c-Pr | Me | Cl | CH₂S(O)₂Et | Cl |
| H | Me | H | OS(O)₂Et | Cl |
| Me | Me | H | OS(O)₂Et | Cl |
| Et | Me | H | OS(O)₂Et | Cl |
| i-Pr | Me | H | OS(O)₂Et | Cl |
| t-Bu | Me | H | OS(O)₂Et | Cl |
| c-Pr | Me | H | OS(O)₂Et | Cl |
| H | Cl | H | OS(O)₂Et | Cl |
| Me | Cl | H | OS(O)₂Et | Cl |
| Et | Cl | H | OS(O)₂Et | Cl |
| i-Pr | Cl | H | OS(O)₂Et | Cl |
| t-Bu | Cl | H | OS(O)₂Et | Cl |
| c-Pr | Cl | H | OS(O)₂Et | Cl |
| H | Me | Cl | OS(O)₂Et | Cl |
| Me | Me | Cl | OS(O)₂Et | Cl |
| Er | Me | Cl | OS(O)₂Et | Cl |
| i-Pr | Me | Cl | OS(O)₂Et | Cl |
| t-Bu | Me | Cl | OS(O)₂Et | Cl |
| c-Pr | Me | Cl | OS(O)₂Et | Cl |
| H | Me | Cl | OS(O)₂CF₃ | Cl |
| Me | Me | Cl | OS(O)₂CF₃ | Cl |
| Et | Me | Cl | OS(O)₂CF₃ | Cl |
| i-Pr | Me | Cl | OS(O)₂CF₃ | Cl |
| t-Bu | Me | Cl | OS(O)₂CF₃ | Cl |

TABLE 1-continued

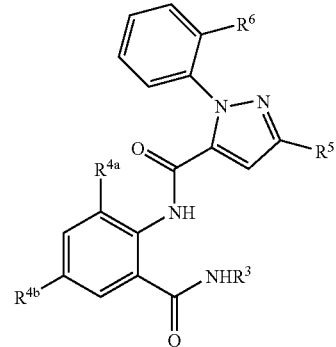

| R³ | R⁴ᵃ | R⁴ᵇ | R⁵ | R⁶ |
|---|---|---|---|---|
| c-Pr | Me | Cl | OS(O)₂CF₃ | Cl |
| H | Cl | Cl | OS(O)₂CF₃ | Cl |
| Me | Cl | Cl | OS(O)₂CF₃ | Cl |
| Et | Cl | Cl | OS(O)₂CF₃ | Cl |
| i-Pr | Cl | Cl | OS(O)₂CF₃ | Cl |
| t-Bu | Cl | Cl | OS(O)₂CF₃ | Cl |
| c-Pr | Cl | Cl | OS(O)₂CF₃ | Cl |
| H | Me | Cl | OCOCF₃ | Cl |
| Me | Me | Cl | OCOCF₃ | Cl |
| Et | Me | Cl | OCOCF₃ | Cl |
| i-Pr | Me | Cl | OCOCF₃ | Cl |
| t-Bu | Me | Cl | OCOCF₃ | Cl |
| c-Pr | Me | Cl | OCOCF₃ | Cl |
| H | Cl | Cl | OCH₂C≡CH | Cl |
| Me | Cl | Cl | OCH₂C≡CH | Cl |
| Et | Cl | Cl | OCH₂C≡CH | Cl |
| i-Pr | Cl | Cl | OCH₂C≡CH | Cl |
| t-Bu | Cl | Cl | OCH₂C≡CH | Cl |
| c-Pr | Cl | Cl | OCH₂C≡CH | Cl |
| H | Cl | Cl | OCH₂C≡CCF₃ | Cl |
| Me | Cl | Cl | OCH₂C≡CCF₃ | Cl |
| Et | Cl | Cl | OCH₂C≡CCF₃ | Cl |
| i-Pr | Cl | Cl | OCH₂C≡CCF₃ | Cl |
| t-Bu | Cl | Cl | OCH₂C≡CCF₃ | Cl |
| c-Pr | Cl | Cl | OCH₂C≡CCF₃ | Cl |
| H | Cl | Cl | OCH₂C≡CMe | Cl |
| Me | Cl | Cl | OCH₂C≡CMe | Cl |
| Et | Cl | Cl | OCH₂C≡CMe | Cl |
| i-Pr | Cl | Cl | OCH₂C≡CMe | Cl |
| t-Bu | Cl | Cl | OCH₂C≡CMe | Cl |
| c-Pr | Cl | Cl | OCH₂C≡CMe | Cl |
| H | Cl | Cl | OCH₂CH=CH₂ | Cl |
| Me | Cl | Cl | OCH₂CH=CH₂ | Cl |
| Et | Cl | Cl | OCH₂CH=CH₂ | Cl |
| i-Pr | Cl | Cl | OCH₂CH=CH₂ | Cl |
| t-Bu | Cl | Cl | OCH₂CH=CH₂ | Cl |
| c-Pr | Cl | Cl | OCH₂CH=CH₂ | Cl |
| H | Me | Cl | NMe₂ | Cl |
| Me | Me | Cl | NMe₂ | Cl |
| Et | Me | Cl | NMe₂ | Cl |
| i-Pr | Me | Cl | NMe₂ | Cl |
| t-Bu | Me | Cl | NMe₂ | Cl |
| c-Pr | Me | Cl | NMe₂ | Cl |
| H | Cl | Cl | NHCH₂CF₃ | Cl |
| Me | Cl | Cl | NHCH₂CF₃ | Cl |
| Et | Cl | Cl | NHCH₂CF₃ | Cl |
| i-Pr | Cl | Cl | NHCH₂CF₃ | Cl |
| t-Bu | Cl | Cl | NHCH₂CF₃ | Cl |
| c-Pr | Cl | Cl | NHCH₂CF₃ | Cl |
| H | Cl | Cl | OCH₂CCl=CH₂ | Cl |
| Me | Cl | Cl | OCH₂CCl=CH₂ | Cl |
| Et | Cl | Cl | OCH₂CCl=CH₂ | Cl |
| i-Pr | Cl | Cl | OCH₂CCl=CH₂ | Cl |
| t-Bu | Cl | Cl | OCH₂CCl=CH₂ | Cl |
| c-Pr | Cl | Cl | OCH₂CCl=CH₂ | Cl |
| H | Cl | Cl | OCH₂CH=CF₂ | Cl |
| Me | Cl | Cl | OCH₂CH=CF₂ | Cl |
| Et | Cl | Cl | OCH₂CH=CF₂ | Cl |
| i-Pr | Cl | Cl | OCH₂CH=CF₂ | Cl |

TABLE 1-continued

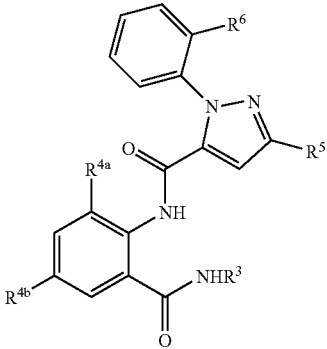

| R³ | R⁴ᵃ | R⁴ᵇ | R⁵ | R⁶ |
|---|---|---|---|---|
| t-Bu | Cl | Cl | OCH₂CH=CF₂ | Cl |
| c-Pr | Cl | Cl | OCH₂CH=CF₂ | Cl |
| H | Cl | Cl | OCH₂CCl=CHCl | Cl |
| Me | Cl | Cl | OCH₂CCl=CHCl | Cl |
| Et | Cl | Cl | OCH₂CCl=CHCl | Cl |
| i-Pr | Cl | Cl | OCH₂CCl=CHCl | Cl |
| t-Bu | Cl | Cl | OCH₂CCl=CHCl | Cl |
| c-Pr | Cl | Cl | OCH₂CCl=CHCl | Cl |
| H | Cl | Cl | NHS(O)₂CF₃ | Cl |
| Me | Cl | Cl | NHS(O)₂CF₃ | Cl |
| Et | Cl | Cl | NHS(O)₂CF₃ | Cl |
| i-Pr | Cl | Cl | NHS(O)₂CF₃ | Cl |
| t-Bu | Cl | Cl | NHS(O)₂CF₃ | Cl |
| c-Pr | Cl | Cl | NHS(O)₂CF₃ | Cl |
| H | Cl | Cl | NHCOCF₃ | Cl |
| Me | Cl | Cl | NHCOCF₃ | Cl |
| Et | Cl | Cl | NHCOCF₃ | Cl |
| i-Pr | Cl | Cl | NHCOCF₃ | Cl |
| t-Bu | Cl | Cl | NHCOCF₃ | Cl |
| c-Pr | Cl | Cl | NHCOCF₃ | Cl |
| H | Cl | Cl | SCH₂CCl=CH₂ | Cl |
| Me | Cl | Cl | SCH₂CCl=CH₂ | Cl |
| Et | Cl | Cl | SCH₂CCl=CH₂ | Cl |
| i-Pr | Cl | Cl | SCH₂CCl=CH₂ | Cl |
| t-Bu | Cl | Cl | SCH₂CCl=CH₂ | Cl |
| c-Pr | Cl | Cl | SCH₂CCl=CH₂ | Cl |
| H | Cl | Cl | OCH₂CN | Cl |
| Me | Cl | Cl | OCH₂CN | Cl |
| Et | Cl | Cl | OCH₂CN | Cl |
| i-Pr | Cl | Cl | OCH₂CN | Cl |
| t-Bu | Cl | Cl | OCH₂CN | Cl |
| c-Pr | Cl | Cl | OCH₂CN | Cl |
| H | Cl | Cl | OCH₂NO₂ | Cl |
| Me | Cl | Cl | OCH₂NO₂ | Cl |
| Et | Cl | Cl | OCH₂NO₂ | Cl |
| i-Pr | Cl | Cl | OCH₂NO₂ | Cl |
| t-Bu | Cl | Cl | OCH₂NO₂ | Cl |
| c-Pr | Cl | Cl | OCH₂NO₂ | Cl |
| H | Cl | Cl | OCH₂NMe₂ | Cl |
| Me | Cl | Cl | OCH₂NMe₂ | Cl |
| Et | Cl | Cl | OCH₂NMe₂ | Cl |
| i-Pr | Cl | Cl | OCH₂NMe₂ | Cl |
| t-Bu | Cl | Cl | OCH₂NMe₂ | Cl |
| c-Pr | Cl | Cl | OCH₂NMe₂ | Cl |
| H | Cl | Cl | OCH₂NHMe | Cl |
| Me | Cl | Cl | OCH₂NHMe | Cl |
| Et | Cl | Cl | OCH₂NHMe | Cl |
| i-Pr | Cl | Cl | OCH₂NHMe | Cl |
| t-Bu | Cl | Cl | OCH₂NHMe | Cl |
| c-Pr | Cl | Cl | OCH₂NHMe | Cl |
| H | Me | Cl | OCH₂-c-Pr | Cl |
| Me | Me | Cl | OCH₂-c-Pr | Cl |
| Et | Me | Cl | OCH₂-c-Pr | Cl |
| i-Pr | Me | Cl | OCH₂-c-Pr | Cl |
| t-Bu | Me | Cl | OCH₂-c-Pr | Cl |
| c-Pr | Me | Cl | OCH₂-c-Pr | Cl |

TABLE 1-continued

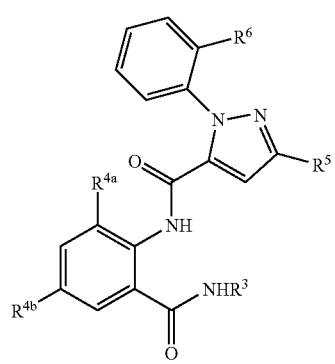

| R³ | R⁴ᵃ | R⁴ᵇ | R⁵ | R⁶ |
|---|---|---|---|---|
| H | Cl | Cl | O-c-Pr | Cl |
| Me | Cl | Cl | O-c-Pr | Cl |
| Et | Cl | Cl | O-c-Pr | Cl |
| i-Pr | Cl | Cl | O-c-Pr | Cl |
| t-Bu | Cl | Cl | O-c-Pr | Cl |
| c-Pr | Cl | Cl | O-c-Pr | Cl |
| H | Cl | Cl | CH₂OCHF₂ | Cl |
| Me | Cl | Cl | CH₂OCHF₂ | Cl |
| Et | Cl | Cl | CH₂OCHF₂ | Cl |
| i-Pr | Cl | Cl | CH₂OCHF₂ | Cl |
| t-Bu | Cl | Cl | CH₂OCHF₂ | Cl |
| c-Pr | Cl | Cl | CH₂OCHF₂ | Cl |
| H | Cl | Cl | CH₂SCHF₂ | Cl |
| Me | Cl | Cl | CH₂SCHF₂ | Cl |
| Et | Cl | Cl | CH₂SCHF₂ | Cl |
| i-Pr | Cl | Cl | CH₂SCHF₂ | Cl |
| t-Bu | Cl | Cl | CH₂SCHF₂ | Cl |
| c-Pr | Cl | Cl | CH₂SCHF₂ | Cl |
| H | Cl | Cl | CH₂S(O)₂CHF₂ | Cl |
| Me | Cl | Cl | CH₂S(O)₂CHF₂ | Cl |
| Et | Cl | Cl | CH₂S(O)₂CHF₂ | Cl |
| i-Pr | Cl | Cl | CH₂S(O)₂CHF₂ | Cl |
| t-Bu | Cl | Cl | CH₂S(O)₂CHF₂ | Cl |
| c-Pr | Cl | Cl | CH₂S(O)₂CHF₂ | Cl |
| H | Me | Cl | 2,2-di-F-c-PrO | Cl |
| Me | Me | Cl | 2,2-di-F-c-PrO | Cl |
| Et | Me | Cl | 2,2-di-F-c-PrO | Cl |
| i-Pr | Me | Cl | 2,2-di-F-c-PrO | Cl |
| t-Bu | Me | Cl | 2,2-di-F-c-PrO | Cl |
| c-Pr | Me | Cl | 2,2-di-P-c-PrO | Cl |
| H | Me | Cl | 2,2,3,3-tetra-F-c-PrO | Cl |
| Me | Me | Cl | 2,2,3,3-tetra-F-c-PrO | Cl |
| Et | Me | Cl | 2,2,3,3-tetra-F-c-PrO | Cl |
| i-Pr | Me | Cl | 2,2,3,3-tetra-F-c-PrO | Cl |
| t-Bu | Me | Cl | 2,2,3,3-tetra-F-c-PrO | Cl |
| c-Pr | Me | Cl | 2,2,3,3-tetra-F-c-PrO | Cl |
| H | Me | Cl | 2,2-di-F-c-PrCH₂O | Cl |
| Me | Me | Cl | 2,2-di-F-c-PrCH₂O | Cl |
| Et | Me | Cl | 2,2-di-F-c-PrCH₂O | Cl |
| i-Pr | Me | Cl | 2,2-di-F-c-PrCH₂O | Cl |
| t-Bu | Me | Cl | 2,2-di-F-c-PrCH₂O | Cl |
| c-Pr | Me | Cl | 2,2-di-F-c-PrCH₂O | Cl |

TABLE 2

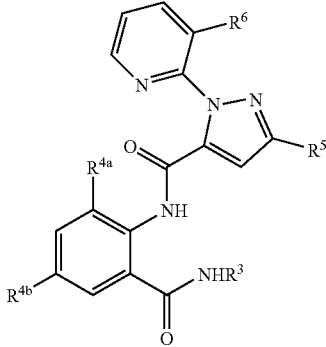

| R³ | R⁴ᵃ | R⁴ᵇ | R⁵ | R⁶ |
|---|---|---|---|---|
| H | Me | H | CF₂OMe | Cl |
| Me | Me | H | CF₂OMe | Cl |
| Et | Me | H | CF₂OMe | Cl |
| i-Pr | Me | H | CF₂OMe | Cl |
| t-Bu | Me | H | CF₂OMe | Cl |
| c-Pr | Me | H | CF₂OMe | Cl |
| H | Me | H | CF₂OMe | F |
| Me | Me | H | CF₂OMe | F |
| Et | Me | H | CF₂OMe | F |
| i-Pr | Me | H | CF₂OMe | F |
| t-Bu | Me | H | CF₂OMe | F |
| c-Pr | Me | H | CF₂OMe | F |
| H | Cl | H | CF₂OMe | Cl |
| Me | Cl | H | CF₂OMe | Cl |
| Et | Cl | H | CF₂OMe | Cl |
| i-Pr | Cl | H | CF₂OMe | Cl |
| t-Bu | Cl | H | CF₂OMe | Cl |
| c-Pr | Cl | H | CF₂OMe | Cl |
| H | Cl | H | CF₂OMe | F |
| Me | Cl | H | CF₂OMe | F |
| Et | Cl | H | CF₂OMe | F |
| i-Pr | Cl | H | CF₂OMe | F |
| t-Bu | Cl | H | CF₂OMe | F |
| c-Pr | Cl | H | CF₂OMe | F |
| H | Me | Cl | CF₂OMe | Cl |
| Me | Me | Cl | CF₂OMe | Cl |
| Et | Me | Cl | CF₂OMe | Cl |
| i-Pr | Me | Cl | CF₂OMe | Cl |
| t-Bu | Me | Cl | CF₂OMe | Cl |
| c-Pr | Me | Cl | CF₂OMe | Cl |
| H | Me | Cl | CF₂OMe | F |
| Me | Me | Cl | CF₂OMe | F |
| Et | Me | Cl | CF₂OMe | F |
| i-Pr | Me | Cl | CF₂OMe | F |
| t-Bu | Me | Cl | CF₂OMe | F |
| c-Pr | Me | Cl | CF₂OMe | F |
| Me | Me | Br | CF₂OMe | Cl |
| Et | Me | Br | CF₂OMe | Cl |
| i-Pr | Me | Br | CF₂OMe | Cl |
| t-Bu | Me | Br | CF₂OMe | Cl |
| c-Pr | Me | Br | CF₂OMe | Cl |
| H | Me | Br | CF₂OMe | F |
| Me | Me | Br | CF₂OMe | F |
| Et | Me | Br | CF₂OMe | F |
| i-Pr | Me | Br | CF₂OMe | F |
| t-Bu | Me | Br | CF₂OMe | F |
| c-Pr | Me | Br | CF₂OMe | F |
| H | Cl | Cl | CF₂OMe | Cl |
| Me | Cl | Cl | CF₂OMe | Cl |
| Et | Cl | Cl | CF₂OMe | Cl |
| i-Pr | Cl | Cl | CF₂OMe | Cl |
| t-Bu | Cl | Cl | CF₂OMe | Cl |
| c-Pr | Cl | Cl | CF₂OMe | Cl |
| H | Cl | Cl | CF₂OMe | F |
| Me | Cl | Cl | CF₂OMe | F |
| Et | Cl | Cl | CF₂OMe | F |
| i-Pr | Cl | Cl | CF₂OMe | F |
| t-Bu | Cl | Cl | CF₂OMe | F |
| c-Pr | Cl | Cl | CF₂OMe | F |

TABLE 2-continued

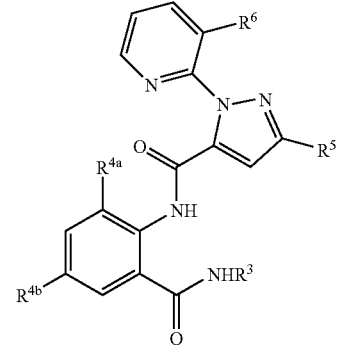

| R³ | R⁴ᵃ | R⁴ᵇ | R⁵ | R⁶ |
|---|---|---|---|---|
| H | Me | CN | CF₂OMe | Cl |
| Me | Me | CN | CF₂OMe | Cl |
| Et | Me | CN | CF₂OMe | Cl |
| i-Pr | Me | CN | CF₂OMe | Cl |
| t-Bu | Me | CN | CF₂OMe | Cl |
| c-Pr | Me | CN | CF₂OMe | Cl |
| H | Me | CN | CF₂OMe | F |
| Me | Me | CN | CF₂OMe | F |
| Et | Me | CN | CF₂OMe | F |
| i-Pr | Me | CN | CF₂OMe | F |
| t-Bu | Me | CN | CF₂OMe | F |
| c-Pr | Me | CN | CF₂OMe | F |
| H | Me | Cl | CF₂OMe | CF₃ |
| Me | Me | Cl | CF₂OMe | CF₃ |
| Et | Me | Cl | CF₂OMe | CF₃ |
| i-Pr | Me | Cl | CF₂OMe | CF₃ |
| t-Bu | Me | Cl | CF₂OMe | CF₃ |
| c-Pr | Me | Cl | CF₂OMe | CF₃ |
| H | Me | Cl | CF₂OMe | CN |
| Me | Me | Cl | CF₂OMe | CN |
| Et | Me | Cl | CF₂OMe | CN |
| i-Pr | Me | Cl | CF₂OMe | CN |
| t-Bu | Me | Cl | CF₂OMe | CN |
| c-Pr | Me | Cl | CF₂OMe | CN |
| H | Me | I | CF₂OMe | Cl |
| Me | Me | I | CF₂OMe | Cl |
| Et | Me | I | CF₂OMe | Cl |
| i-Pr | Me | I | CF₂OMe | Cl |
| t-Bu | Me | I | CF₂OMe | Cl |
| c-Pr | Me | I | CF₂OMe | Cl |
| H | Me | F | CF₂OMe | Cl |
| Me | Me | F | CF₂OMe | Cl |
| Et | Me | F | CF₂OMe | Cl |
| i-Pr | Me | F | CF₂OMe | Cl |
| t-Bu | Me | F | CF₂OMe | Cl |
| c-Pr | Me | F | CF₂OMe | Cl |
| H | Br | Cl | CF₂OMe | Cl |
| Me | Br | Cl | CF₂OMe | Cl |
| Et | Br | Cl | CF₂OMe | Cl |
| i-Pr | Br | Cl | CF₂OMe | Cl |
| t-Bu | Br | Cl | CF₂OMe | Cl |
| c-Pr | Br | Cl | CF₂OMe | Cl |
| H | Cl | Br | CF₂OMe | Cl |
| Me | Cl | Br | CF₂OMe | Cl |
| Et | Cl | Br | CF₂OMe | Cl |
| i-Pr | Cl | Br | CF₂OMe | Cl |
| t-Bu | Cl | Br | CF₂OMe | Cl |
| c-Pr | Cl | Br | CF₂OMe | Cl |
| H | Me | Cl | CF₂SMe | Cl |
| Me | Me | Cl | CF₂SMe | Cl |
| Et | Me | Cl | CF₂SMe | Cl |
| i-Pr | Me | Cl | CF₂SMe | Cl |
| t-Bu | Me | Cl | CF₂SMe | Cl |
| c-Pr | Me | Cl | CF₂SMe | Cl |
| H | Me | Cl | CF₂S(O)Me | Cl |
| Me | Me | Cl | CF₂S(O)Me | Cl |
| Et | Me | Cl | CF₂S(O)Me | Cl |
| i-Pr | Me | Cl | CF₂S(O)Me | Cl |
| t-Bu | Me | Cl | CF₂S(O)Me | Cl |

TABLE 2-continued

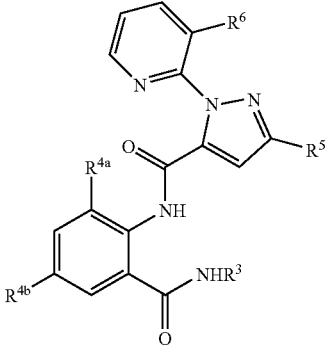

| R³ | R⁴ᵃ | R⁴ᵇ | R⁵ | R⁶ |
|---|---|---|---|---|
| c-Pr | Me | Cl | CF₂S(O)Me | Cl |
| H | Me | Cl | CF₂S(O)₂Me | Cl |
| Me | Me | Cl | CF₂S(O)₂Me | Cl |
| Et | Me | Cl | CF₂S(O)₂Me | Cl |
| i-Pr | Me | Cl | CF₂S(O)₂Me | Cl |
| t-Bu | Me | Cl | CF₂S(O)₂Me | Cl |
| c-Pr | Me | Cl | CF₂S(O)₂Me | Cl |
| H | Me | H | CH₂OMe | Cl |
| Me | Me | H | CH₂OMe | Cl |
| Et | Me | H | CH₂OMe | Cl |
| i-Pr | Me | H | CH₂OMe | Cl |
| t-Bu | Me | H | CH₂OMe | Cl |
| c-Pr | Me | H | CH₂OMe | Cl |
| H | Cl | H | CH₂OMe | Cl |
| Me | Cl | H | CH₂OMe | Cl |
| Et | Cl | H | CH₂OMe | Cl |
| i-Pr | Cl | H | CH₂OMe | Cl |
| t-Bu | Cl | H | CH₂OMe | Cl |
| c-Pr | Cl | H | CH₂OMe | Cl |
| H | Me | Cl | CH₂OMe | Cl |
| Me | Me | Cl | CH₂OMe | Cl |
| Et | Me | Cl | CH₂OMe | Cl |
| i-Pr | Me | Cl | CH₂OMe | Cl |
| t-Bu | Me | Cl | CH₂OMe | Cl |
| c-Pr | Me | Cl | CH₂OMe | Cl |
| H | Me | H | CH₂SMe | Cl |
| Me | Me | H | CH₂SMe | Cl |
| Et | Me | H | CH₂SMe | Cl |
| i-Pr | Me | H | CH₂SMe | Cl |
| t-Bu | Me | H | CH₂SMe | Cl |
| c-Pr | Me | H | CH₂SMe | Cl |
| H | Cl | H | CH₂SMe | Cl |
| Me | Cl | H | CH₂SMe | Cl |
| Et | Cl | H | CH₂SMe | Cl |
| i-Pr | Cl | H | CH₂SMe | Cl |
| t-Bu | Cl | H | CH₂SMe | Cl |
| c-Pr | Cl | H | CH₂SMe | Cl |
| H | Me | Cl | CH₂SMe | Cl |
| Me | Me | Cl | CH₂SMe | Cl |
| Et | Me | Cl | CH₂SMe | Cl |
| i-Pr | Me | Cl | CH₂SMe | Cl |
| t-Bu | Me | Cl | CH₂SMe | Cl |
| c-Pr | Me | Cl | CH₂SMe | Cl |
| H | Me | Cl | CH₂S(O)Me | Cl |
| Me | Me | Cl | CH₂S(O)Me | Cl |
| Et | Me | Cl | CH₂S(O)Me | Cl |
| i-Pr | Me | Cl | CH₂S(O)Me | Cl |
| t-Bu | Me | Cl | CH₂S(O)Me | Cl |
| c-Pr | Me | Cl | CH₂S(O)Me | Cl |
| H | Me | Cl | CH₂S(O)₂Me | Cl |
| Me | Me | Cl | CH₂S(O)₂Me | Cl |
| Et | Me | Cl | CH₂S(O)₂Me | Cl |
| i-Pr | Me | Cl | CH₂S(O)₂Me | Cl |
| t-Bu | Me | Cl | CH₂S(O)₂Me | Cl |
| c-Pr | Me | Cl | CH₂S(O)₂Me | Cl |
| H | Me | H | OS(O)₂Me | Cl |
| Me | Me | H | OS(O)₂Me | Cl |
| Et | Me | H | OS(O)₂Me | Cl |
| i-Pr | Me | H | OS(O)₂Me | Cl |

TABLE 2-continued

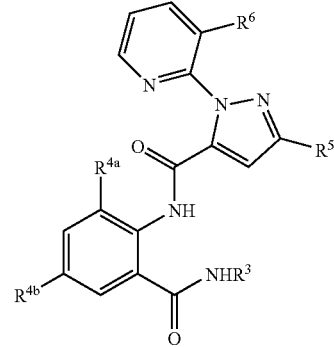

| R³ | R⁴ᵃ | R⁴ᵇ | R⁵ | R⁶ |
|---|---|---|---|---|
| t-Bu | Me | H | OS(O)₂Me | Cl |
| c-Pr | Me | H | OS(O)₂Me | Cl |
| H | Cl | H | OS(O)₂Me | Cl |
| Me | Cl | H | OS(O)₂Me | Cl |
| Et | Cl | H | OS(O)₂Me | Cl |
| i-Pr | Cl | H | OS(O)₂Me | Cl |
| t-Bu | Cl | H | OS(O)₂Me | Cl |
| c-Pr | Cl | H | OS(O)₂Me | Cl |
| H | Me | Cl | OS(O)₂Me | Cl |
| Me | Me | Cl | OS(O)₂Me | Cl |
| Et | Me | Cl | OS(O)₂Me | Cl |
| i-Pr | Me | Cl | OS(O)₂Me | Cl |
| t-Bu | Me | Cl | OS(O)₂Me | Cl |
| c-Pr | Me | Cl | OS(O)₂Me | Cl |
| H | Me | H | OS(O)₂CF₃ | Cl |
| Me | Me | H | OS(O)₂CF₃ | Cl |
| Et | Me | H | OS(O)₂CF₃ | Cl |
| i-Pr | Me | H | OS(O)₂CF₃ | Cl |
| t-Bu | Me | H | OS(O)₂CF₃ | Cl |
| c-Pr | Me | H | OS(O)₂CF₃ | Cl |
| H | Cl | H | OS(O)₂CF₃ | Cl |
| Me | Cl | H | OS(O)₂CF₃ | Cl |
| Et | Cl | H | OS(O)₂CF₃ | Cl |
| i-Pr | Cl | H | OS(O)₂CF₃ | Cl |
| t-Bu | Cl | H | OS(O)₂CF₃ | Cl |
| c-Pr | Cl | H | OS(O)₂CF₃ | Cl |
| H | Me | Cl | OS(O)₂CClF₂ | Cl |
| Me | Me | Cl | OS(O)₂CClF₂ | Cl |
| Et | Me | Cl | OS(O)₂CClF₂ | Cl |
| i-Pr | Me | Cl | OS(O)₂CClF₂ | Cl |
| t-Bu | Me | Cl | OS(O)₂CClF₂ | Cl |
| c-Pr | Me | Cl | OS(O)₂CClF₂ | Cl |
| H | Me | Cl | OCH₂C≡CH | Cl |
| Me | Me | Cl | OCH₂C≡CH | Cl |
| Et | Me | Cl | OCH₂C≡CH | Cl |
| i-Pr | Me | Cl | OCH₂C≡CH | Cl |
| t-Bu | Me | Cl | OCH₂C≡CH | Cl |
| c-Pr | Me | Cl | OCH₂C≡CH | Cl |
| H | Me | Cl | OCH₂C≡CCF₃ | Cl |
| Me | Me | Cl | OCH₂C≡CCF₃ | Cl |
| Et | Me | Cl | OCH₂C≡CCF₃ | Cl |
| i-Pr | Me | Cl | OCH₂C≡CCF₃ | Cl |
| t-Bu | Me | Cl | OCH₂C≡CCF₃ | Cl |
| c-Pr | Me | Cl | OCH₂C≡CCF₃ | Cl |
| H | Me | Cl | OCH₂C≡CMe | Cl |
| Me | Me | Cl | OCH₂C≡CMe | Cl |
| Et | Me | Cl | OCH₂C≡CMe | Cl |
| i-Pr | Me | Cl | OCH₂C≡CMe | Cl |
| t-Bu | Me | Cl | OCH₂C≡CMe | Cl |
| c-Pr | Me | Cl | OCH₂C≡CMe | Cl |
| H | Me | Cl | OCH₂CH=CH₂ | Cl |
| Me | Me | Cl | OCH₂CH=CH₂ | Cl |
| Et | Me | Cl | OCH₂CH=CH₂ | Cl |
| i-Pr | Me | Cl | OCH₂CH=CH₂ | Cl |
| t-Bu | Me | Cl | OCH₂CH=CH₂ | Cl |
| c-Pr | Me | Cl | OCH₂CH=CH₂ | Cl |
| H | Me | Cl | NHMe | Cl |
| Me | Me | Cl | NHMe | Cl |
| Et | Me | Cl | NHMe | Cl |

TABLE 2-continued

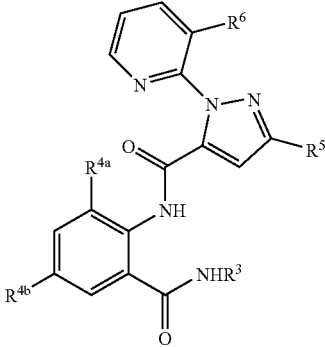

| R³ | R⁴ᵃ | R⁴ᵇ | R⁵ | R⁶ |
|---|---|---|---|---|
| i-Pr | Me | Cl | NHMe | Cl |
| t-Bu | Me | Cl | NHMe | Cl |
| c-Pr | Me | Cl | NHMe | Cl |
| H | Me | Cl | NHCH₂CF₃ | Cl |
| Me | Me | Cl | NHCH₂CF₃ | Cl |
| Et | Me | Cl | NHCH₂CF₃ | Cl |
| i-Pr | Me | Cl | NHCH₂CF₃ | Cl |
| t-Bu | Me | Cl | NHCH₂CF₃ | Cl |
| c-Pr | Me | Cl | NHCH₂CF₃ | Cl |
| H | Me | Cl | OCH₂CCl=CH₂ | Cl |
| Me | Me | Cl | OCH₂CCl=CH₂ | Cl |
| Et | Me | Cl | OCH₂CCl=CH₂ | Cl |
| i-Pr | Me | Cl | OCH₂CCl=CH₂ | Cl |
| t-Bu | Me | Cl | OCH₂CCl=CH₂ | Cl |
| c-Pr | Me | Cl | OCH₂CCl=CH₂ | Cl |
| H | Me | Cl | OCH₂CH=CF₂ | Cl |
| Me | Me | Cl | OCH₂CH=CF₂ | Cl |
| Et | Me | Cl | OCH₂CH=CF₂ | Cl |
| i-Pr | Me | Cl | OCH₂CH=CF₂ | Cl |
| t-Bu | Me | Cl | OCH₂CH=CF₂ | Cl |
| c-Pr | Me | Cl | OCH₂CH=CF₂ | Cl |
| H | Me | Cl | OCH₂CCl=CHCl | Cl |
| Me | Me | Cl | OCH₂CCl=CHCl | Cl |
| Et | Me | Cl | OCH₂CCl=CHCl | Cl |
| i-Pr | Me | Cl | OCH₂CCl=CHCl | Cl |
| t-Bu | Me | Cl | OCH₂CCl=CHCl | Cl |
| c-Pr | Me | Cl | OCH₂CCl=CHCl | Cl |
| H | Me | Cl | NHS(O)₂CF₃ | Cl |
| Me | Me | Cl | NHS(O)₂CF₃ | Cl |
| Et | Me | Cl | NHS(O)₂CF₃ | Cl |
| i-Pr | Me | Cl | NHS(O)₂CF₃ | Cl |
| t-Bu | Me | Cl | NHS(O)₂CF₃ | Cl |
| c-Pr | Me | Cl | NHS(O)₂CF₃ | Cl |
| H | Me | Cl | NHCOCF₃ | Cl |
| Me | Me | Cl | NHCOCF₃ | Cl |
| Et | Me | Cl | NHCOCF₃ | Cl |
| i-Pr | Me | Cl | NHCOCF₃ | Cl |
| t-Bu | Me | Cl | NHCOCF₃ | Cl |
| c-Pr | Me | Cl | NHCOCF₃ | Cl |
| H | Me | Cl | SCH₂CCl=CH₂ | Cl |
| Me | Me | Cl | SCH₂CCl=CH₂ | Cl |
| Et | Me | Cl | SCH₂CCl=CH₂ | Cl |
| i-Pr | Me | Cl | SCH₂CCl=CH₂ | Cl |
| t-Bu | Me | Cl | SCH₂CCl=CH₂ | Cl |
| c-Pr | Me | Cl | SCH₂CCl=CH₂ | Cl |
| H | Me | Cl | OCH₂CN | Cl |
| Me | Me | Cl | OCH₂CN | Cl |
| Et | Me | Cl | OCH₂CN | Cl |
| i-Pr | Me | Cl | OCH₂CN | Cl |
| t-Bu | Me | Cl | OCH₂CN | Cl |
| c-Pr | Me | Cl | OCH₂CN | Cl |
| H | Me | Cl | OCH₂NO₂ | Cl |
| Me | Me | Cl | OCH₂NO₂ | Cl |
| Et | Me | Cl | OCH₂NO₂ | Cl |
| i-Pr | Me | Cl | OCH₂NO₂ | Cl |
| t-Bu | Me | Cl | OCH₂NO₂ | Cl |
| c-Pr | Me | Cl | OCH₂NO₂ | Cl |
| H | Me | Cl | OCH₂NMe₂ | Cl |
| Me | Me | Cl | OCH₂NMe₂ | Cl |

TABLE 2-continued

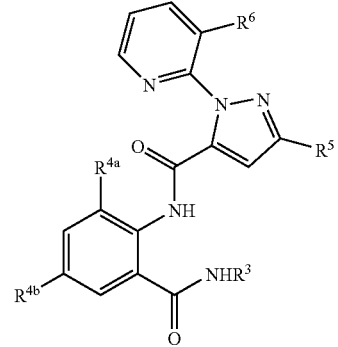

| R³ | R⁴ᵃ | R⁴ᵇ | R⁵ | R⁶ |
|---|---|---|---|---|
| Et | Me | Cl | OCH₂NMe₂ | Cl |
| i-Pr | Me | Cl | OCH₂NMe₂ | Cl |
| t-Bu | Me | Cl | OCH₂NMe₂ | Cl |
| c-Pr | Me | Cl | OCH₂NHMe | Cl |
| H | Me | Cl | OCH₂NHMe | Cl |
| Me | Me | Cl | OCH₂NHMe | Cl |
| Et | Me | Cl | OCH₂NHMe | Cl |
| i-Pr | Me | Cl | OCH₂NHMe | Cl |
| t-Bu | Me | Cl | OCH₂NHMe | Cl |
| c-Pr | Me | Cl | OCH₂NHMe | Cl |
| H | Me | Cl | CSNH₂ | Cl |
| Me | Me | Cl | CSNH₂ | Cl |
| Et | Me | Cl | CSNH₂ | Cl |
| i-Pr | Me | Cl | CSNH₂ | Cl |
| t-Bu | Me | Cl | CSNH₂ | Cl |
| c-Pr | Me | Cl | CSNH₂ | Cl |
| H | Me | Cl | O-c-Pr | Cl |
| Me | Me | Cl | O-c-Pr | Cl |
| Et | Me | Cl | O-c-Pr | Cl |
| i-Pr | Me | Cl | O-c-Pr | Cl |
| t-Bu | Me | Cl | O-c-Pr | Cl |
| c-Pr | Me | Cl | O-c-Pr | Cl |
| H | Me | Cl | CH₂OCHF₂ | Cl |
| Me | Me | Cl | CH₂OCHF₂ | Cl |
| Et | Me | Cl | CH₂OCHF₂ | Cl |
| i-Pr | Me | Cl | CH₂OCHF₂ | Cl |
| t-Bu | Me | Cl | CH₂OCHF₂ | Cl |
| c-Pr | Me | Cl | CH₂OCHF₂ | Cl |
| H | Me | Cl | CH₂SCHF₂ | Cl |
| Me | Me | Cl | CH₂SCHF₂ | Cl |
| Et | Me | Cl | CH₂SCHF₂ | Cl |
| i-Pr | Me | Cl | CH₂SCHF₂ | Cl |
| t-Bu | Me | Cl | CH₂SCHF₂ | Cl |
| c-Pr | Me | Cl | CH₂SCHF₂ | Cl |
| H | Me | Cl | CH₂S(O)₂CHF₂ | Cl |
| Me | Me | Cl | CH₂S(O)₂CHF₂ | Cl |
| Et | Me | Cl | CH₂S(O)₂CHF₂ | Cl |
| i-Pr | Me | Cl | CH₂S(O)₂CHF₂ | Cl |
| t-Bu | Me | Cl | CH₂S(O)₂CHF₂ | Cl |
| c-Pr | Me | Cl | CH₂S(O)₂CHF₂ | Cl |
| H | Me | Cl | 2,2-di-F-c-Pr | Cl |
| Me | Me | Cl | 2,2-di-F-c-Pr | Cl |
| Et | Me | Cl | 2,2-di-F-c-Pr | Cl |
| i-Pr | Me | Cl | 2,2-di-F-c-Pr | Cl |
| t-Bu | Me | Cl | 2,2-di-F-c-Pr | Cl |
| c-Pr | Me | Cl | 2,2-di-F-c-Pr | Cl |
| H | Me | Cl | 2,2,3,3-tetra-F-c-Pr | Cl |
| Me | Me | Cl | 2,2,3,3-tetra-F-c-Pr | Cl |
| Et | Me | Cl | 2,2,3,3-tetra-F-c-Pr | Cl |
| i-Pr | Me | Cl | 2,2,3,3-tetra-F-c-Pr | Cl |
| t-Bu | Me | Cl | 2,2,3,3-tetra-F-c-Pr | Cl |
| c-Pr | Me | Cl | 2,2,3,3-tetra-F-c-Pr | Cl |
| H | Me | Cl | 2,2-di-F-c-PrCH₂ | Cl |
| Me | Me | Cl | 2,2-di-F-c-PrCH₂ | Cl |
| Et | Me | Cl | 2,2-di-F-c-PrCH₂ | Cl |
| i-Pr | Me | Cl | 2,2-di-P-c-PrCH₂ | Cl |
| t-Bu | Me | Cl | 2,2-di-F-c-PrCH₂ | Cl |
| c-Pr | Me | Cl | 2,2-di-F-c-PrCH₂ | Cl |
| H | Me | H | CF₂OEt | Cl |

TABLE 2-continued

| R³ | R⁴ᵃ | R⁴ᵇ | R⁵ | R⁶ |
|---|---|---|---|---|
| Me | Me | H | CF₂OEt | Cl |
| Et | Me | H | CF₂OEt | Cl |
| i-Pr | Me | H | CF₂OEt | Cl |
| t-Bu | Me | H | CF₂OEt | Cl |
| c-Pr | Me | H | CF₂OEt | Cl |
| H | Me | H | CF₂OEt | F |
| Me | Me | H | CF₂OEt | F |
| Et | Me | H | CF₂OEt | F |
| i-Pr | Me | H | CF₂OEt | F |
| t-Bu | Me | H | CF₂OEt | F |
| c-Pr | Me | H | CF₂OEt | F |
| H | Cl | H | CF₂OEt | Cl |
| Me | Cl | H | CF₂OEt | Cl |
| Et | Cl | H | CF₂OEt | Cl |
| i-Pr | Cl | H | CF₂OEt | Cl |
| t-Bu | Cl | H | CF₂OEt | Cl |
| c-Pr | Cl | H | CF₂OEt | Cl |
| H | Cl | H | CF₂OEt | F |
| Me | Cl | H | CF₂OEt | F |
| Et | Cl | H | CF₂OEt | F |
| i-Pr | Cl | H | CF₂OEt | F |
| t-Bu | Cl | H | CF₂OEt | F |
| c-Pr | Cl | H | CF₂OEt | F |
| H | Me | Cl | CF₂OEt | Cl |
| Me | Me | Cl | CF₂OEt | Cl |
| Et | Me | Cl | CF₂OEI | Cl |
| i-Pr | Me | Cl | CF₂OEt | Cl |
| t-Bu | Me | Cl | CF₂OEt | Cl |
| c-Pr | Me | Cl | CF₂OEt | Cl |
| H | Me | Cl | CF₂OEt | F |
| Me | Me | Cl | CF₂OEt | F |
| Et | Me | Cl | CF₂OEt | F |
| i-Pr | Me | Cl | CF₂OEt | F |
| t-Bu | Me | Cl | CF₂OEt | F |
| c-Pr | Me | Cl | CF₂OEt | F |
| Me | Me | Br | CF₂OEt | Cl |
| Et | Me | Br | CF₂OEt | Cl |
| i-Pr | Me | Br | CF₂OEt | Cl |
| t-Bu | Me | Br | CF₂OEt | Cl |
| c-Pr | Me | Br | CF₂OEt | Cl |
| H | Me | Br | CF₂OEt | F |
| Me | Me | Br | CF₂OEt | F |
| Et | Me | Br | CF₂OEt | F |
| i-Pr | Me | Br | CF₂OEt | F |
| t-Bu | Me | Br | CF₂OEt | F |
| c-Pr | Me | Br | CF₂OEt | F |
| H | Cl | Cl | CF₂OEt | Cl |
| Me | Cl | Cl | CF₂OEt | Cl |
| Et | Cl | Cl | CF₂OEt | Cl |
| i-Pr | Cl | Cl | CF₂OEt | Cl |
| t-Bu | Cl | Cl | CF₂OEt | Cl |
| c-Pr | Cl | Cl | CF₂OEt | Cl |
| H | Cl | Cl | CF₂OEt | F |
| Me | Cl | Cl | CF₂OEt | F |
| Et | Cl | Cl | CF₂OEt | F |
| i-Pr | Cl | Cl | CF₂OEt | F |
| t-Bu | Cl | Cl | CF₂OEt | F |
| c-Pr | Cl | Cl | CF₂OEt | F |
| H | Me | CN | CF₂OEt | Cl |
| Me | Me | CN | CF₂OEt | Cl |
| Et | Me | CN | CF₂OEt | Cl |
| i-Pr | Me | CN | CF₂OEt | Cl |
| t-Bu | Me | CN | CF₂OEt | Cl |
| c-Pr | Me | CN | CF₂OEt | Cl |
| H | Me | CN | CF₂OEt | F |
| Me | Me | CN | CF₂OEt | F |
| Et | Me | CN | CF₂OEt | F |
| i-Pr | Me | CN | CF₂OEt | F |
| t-Bu | Me | CN | CF₂OEt | F |
| c-Pr | Me | CN | CF₂OEt | F |
| H | Me | Cl | CF₂OEt | CF₃ |
| Me | Me | Cl | CF₂OEt | CF₃ |
| Et | Me | Cl | CF₂OEt | CF₃ |
| i-Pr | Me | Cl | CF₂OEt | CF₃ |
| t-Bu | Me | Cl | CF₂OEt | CF₃ |
| c-Pr | Me | Cl | CF₂OEt | CF₃ |
| H | Me | Cl | CF₂OEt | CN |
| Me | Me | Cl | CF₂OEt | CN |
| Et | Me | Cl | CF₂OEt | CN |
| i-Pr | Me | Cl | CF₂OEt | CN |
| t-Bu | Me | Cl | CF₂OEt | CN |
| c-Pr | Me | Cl | CF₂OEt | CN |
| H | Me | I | CF₂OEt | Cl |
| Me | Me | I | CF₂OEt | Cl |
| Et | Me | I | CF₂OEt | Cl |
| i-Pr | Me | I | CF₂OEt | Cl |
| t-Bu | Me | I | CF₂OEt | Cl |
| c-Pr | Me | I | CF₂OEt | Cl |
| H | Me | F | CF₂OEt | Cl |
| Me | Me | F | CF₂OEt | Cl |
| Et | Me | F | CF₂OEt | Cl |
| i-Pr | Me | F | CF₂OEt | Cl |
| t-Bu | Me | F | CF₂OEt | Cl |
| c-Pr | Me | F | CF₂OEt | Cl |
| H | Br | Cl | CF₂OEt | Cl |
| Me | Br | Cl | CF₂OEt | Cl |
| Et | Br | Cl | CF₂OEt | Cl |
| i-Pr | Br | Cl | CF₂OEt | Cl |
| t-Bu | Br | Cl | CF₂OEt | Cl |
| c-Pr | Br | Cl | CF₂OEt | Cl |
| H | Cl | Br | CF₂OEt | Cl |
| Me | Cl | Br | CF₂OEt | Cl |
| Et | Cl | Br | CF₂DEt | Cl |
| i-Pr | Cl | Br | CF₂OEt | Cl |
| t-Bu | Cl | Br | CF₂OEt | Cl |
| c-Pr | Cl | Br | CF₂OEt | Cl |
| H | Me | Cl | CF₂SEt | Cl |
| Me | Me | Cl | CF₂SEt | Cl |
| Et | Me | Cl | CF₂SEt | Cl |
| i-Pr | Me | Cl | CF₂SEt | Cl |
| t-Bu | Me | Cl | CF₂SEt | Cl |
| c-Pr | Me | Cl | CF₂SEt | Cl |
| H | Me | Cl | CF₂S(O)Et | Cl |
| Me | Me | Cl | CF₂S(O)Et | Cl |
| Et | Me | Cl | CF₂S(O)Et | Cl |
| i-Pr | Me | Cl | CF₂S(O)Et | Cl |
| t-Bu | Me | Cl | CF₂S(O)Et | Cl |
| c-Pr | Me | Cl | CF₂S(O)Et | Cl |

TABLE 2-continued

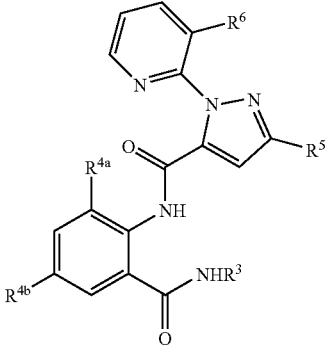

| R³ | R⁴ᵃ | R⁴ᵇ | R⁵ | R⁶ |
|---|---|---|---|---|
| H | Me | Cl | CF₂S(O)₂Et | Cl |
| Me | Me | Cl | CF₂S(O)₂Et | Cl |
| Et | Me | Cl | CF₂S(O)₂Et | Cl |
| i-Pr | Me | Cl | CF₂S(O)₂Et | Cl |
| t-Bu | Me | Cl | CF₂S(O)₂Et | Cl |
| c-Pr | Me | Cl | CF₂S(O)₂Et | Cl |
| H | Me | H | CH₂OEt | Cl |
| Me | Me | H | CH₂OEt | Cl |
| Et | Me | H | CH₂OEt | Cl |
| i-Pr | Me | H | CH₂OEt | Cl |
| t-Bu | Me | H | CH₂OEt | Cl |
| c-Pr | Me | H | CH₂OEt | Cl |
| H | Cl | H | CH₂OEt | Cl |
| Me | Cl | H | CH₂OEt | Cl |
| Et | Cl | H | CH₂OEt | Cl |
| i-Pr | Cl | H | CH₂OEt | Cl |
| t-Bu | Cl | H | CH₂OEt | Cl |
| c-Pr | Cl | H | CH₂OEt | Cl |
| H | Me | Cl | CH₂OEt | Cl |
| Me | Me | Cl | CH₂OEt | Cl |
| Et | Me | Cl | CH₂OEt | Cl |
| i-Pr | Me | Cl | CH₂OEt | Cl |
| t-Bu | Me | Cl | CH₂OEt | Cl |
| c-Pr | Me | Cl | CH₂OEt | Cl |
| H | Me | H | CH₂SEt | Cl |
| Me | Me | H | CH₂SEt | Cl |
| Et | Me | H | CH₂SEt | Cl |
| i-Pr | Me | H | CH₂SEt | Cl |
| t-Bu | Me | H | CH₂SEt | Cl |
| c-Pr | Me | H | CH₂SEt | Cl |
| H | Cl | H | CH₂SEt | Cl |
| Me | Cl | H | CH₂SEt | Cl |
| Et | Cl | H | CH₂SEt | Cl |
| i-Pr | Cl | H | CH₂SEt | Cl |
| t-Bu | Cl | H | CH₂SEt | Cl |
| c-Pr | Cl | H | CH₂SEt | Cl |
| H | Me | Cl | CH₂SEt | Cl |
| Me | Me | Cl | CH₂SEt | Cl |
| Et | Me | Cl | CH₂SEt | Cl |
| i-Pr | Me | Cl | CH₂SEt | Cl |
| t-Bu | Me | Cl | CH₂SEt | Cl |
| c-Pr | Me | Cl | CH₂SEt | Cl |
| H | Me | Cl | CH₂S(O)Et | Cl |
| Me | Me | Cl | CH₂S(O)Et | Cl |
| Et | Me | Cl | CH₂S(O)Et | Cl |
| i-Pr | Me | Cl | CH₂S(O)Et | Cl |
| t-Bu | Me | Cl | CH₂S(O)Et | Cl |
| c-Pr | Me | Cl | CH₂S(O)Et | Cl |
| H | Me | Cl | CH₂S(O)₂Et | Cl |
| Me | Me | Cl | CH₂S(O)₂Et | Cl |
| Et | Me | Cl | CH₂S(O)₂Et | Cl |
| i-Pr | Me | Cl | CH₂S(O)₂Et | Cl |
| t-Bu | Me | Cl | CH₂S(O)₂Et | Cl |
| c-Pr | Me | Cl | CH₂S(O)₂Et | Cl |
| H | Me | H | OS(O)₂Et | Cl |
| Me | Me | H | OS(O)₂Et | Cl |
| Et | Me | H | OS(O)₂Et | Cl |
| i-Pr | Me | H | OS(O)₂Et | Cl |
| t-Bu | Me | H | OS(O)₂Et | Cl |

TABLE 2-continued

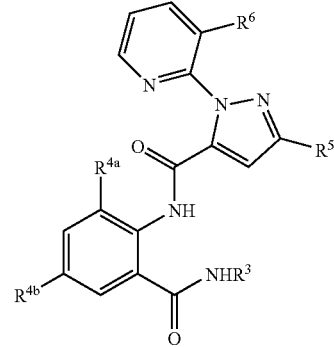

| R³ | R⁴ᵃ | R⁴ᵇ | R⁵ | R⁶ |
|---|---|---|---|---|
| c-Pr | Me | H | OS(O)₂Et | Cl |
| H | Cl | H | OS(O)₂Et | Cl |
| Me | Cl | H | OS(O)₂Et | Cl |
| Et | Cl | H | O5(O)₂Et | Cl |
| i-Pr | Cl | H | OS(O)₂Et | Cl |
| t-Bu | Cl | H | OS(O)₂Et | Cl |
| c-Pr | Cl | H | OS(O)₂Et | Cl |
| H | Me | Cl | OS(O)₂Et | Cl |
| Me | Me | Cl | OS(O)₂Et | Cl |
| Et | Me | Cl | OS(O)₂Et | Cl |
| i-Pr | Me | Cl | OS(O)₂Et | Cl |
| r-Bu | Me | Cl | OS(O)₂Et | Cl |
| c-Pr | Me | Cl | OS(O)₂Et | Cl |
| H | Me | Cl | OS(O)₂CF₃ | Cl |
| Me | Me | Cl | OS(O)₂CF₃ | Cl |
| Et | Me | Cl | OS(O)₂CF₃ | Cl |
| i-Pr | Me | Cl | OS(O)₂CF₃ | Cl |
| t-Bu | Me | Cl | OS(O)₂CF₃ | Cl |
| c-Pr | Me | Cl | OS(O)₂CF₃ | Cl |
| H | Cl | Cl | OS(O)₂CF₃ | Cl |
| Me | Cl | Cl | OS(O)₂CF₃ | Cl |
| Et | Cl | Cl | OS(O)₂CF₃ | Cl |
| i-Pr | Cl | Cl | OS(O)₂CF₃ | Cl |
| t-Bu | Cl | Cl | OS(O)₂CF₃ | Cl |
| c-Pr | Cl | Cl | OS(O)₂CF₃ | Cl |
| H | Me | Cl | OCOCF₃ | Cl |
| Me | Me | Cl | OCOCF₃ | Cl |
| Et | Me | Cl | OCOCF₃ | Cl |
| i-Pr | Me | Cl | OCOCF₃ | Cl |
| t-Bu | Me | Cl | OCOCF₃ | Cl |
| c-Pr | Me | Cl | OCOCF₃ | Cl |
| H | Cl | Cl | OCH₂C≡CH | Cl |
| Me | Cl | Cl | OCH₂C≡CH | Cl |
| Et | Cl | Cl | OCH₂C≡CH | Cl |
| i-Pr | Cl | Cl | OCH₂C≡CH | Cl |
| t-Bu | Cl | Cl | OCH₂C≡CH | Cl |
| c-Pr | Cl | Cl | OCH₂C≡CH | Cl |
| H | Cl | Cl | OCH₂C≡CCF₃ | Cl |
| Me | Cl | Cl | OCH₂C≡CCF₃ | Cl |
| Et | Cl | Cl | OCH₂C≡CCF₃ | Cl |
| i-Pr | Cl | Cl | OCH₂C≡CCF₃ | Cl |
| t-Bu | Cl | Cl | OCH₂C≡CCF₃ | Cl |
| c-Pr | Cl | Cl | OCH₂C≡CCF₃ | Cl |
| H | Cl | Cl | OCH₂C≡CMe | Cl |
| Me | Cl | Cl | OCH₂C≡CMe | Cl |
| Et | Cl | Cl | OCH₂C≡CMe | Cl |
| i-Pr | Cl | Cl | OCH₂C≡CMe | Cl |
| t-Bu | Cl | Cl | OCH₂C≡CMe | Cl |
| c-Pr | Cl | Cl | OCH₂C≡CMe | Cl |
| H | Cl | Cl | OCH₂CH=CH₂ | Cl |
| Me | Cl | Cl | OCH₂CH=CH₂ | Cl |
| Et | Cl | Cl | OCH₂CH=CH₂ | Cl |
| i-Pr | Cl | Cl | OCH₂CH=CH₂ | Cl |
| t-Bu | Cl | Cl | OCH₂CH=CH₂ | Cl |
| c-Pr | Cl | Cl | OCH₂CH=CH₂ | Cl |
| H | Me | Cl | NMe₂ | Cl |
| Me | Me | Cl | NMe₂ | Cl |
| Et | Me | Cl | NMe₂ | Cl |
| i-Pr | Me | Cl | NMe₂ | Cl |

TABLE 2-continued

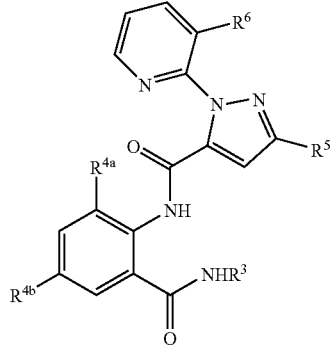

| R³ | R⁴ᵃ | R⁴ᵇ | R⁵ | R⁶ |
|---|---|---|---|---|
| t-Bu | Me | Cl | NMe₂ | Cl |
| c-Pr | Me | Cl | NMe₂ | Cl |
| H | Cl | Cl | NHCH₂CF₃ | Cl |
| Me | Cl | Cl | NHCH₂CF₃ | Cl |
| Et | Cl | Cl | NHCH₂CF₃ | Cl |
| i-Pr | Cl | Cl | NHCH₂CF₃ | Cl |
| t-Bu | Cl | Cl | NHCH₂CF₃ | Cl |
| c-Pr | Cl | Cl | NHCH₂CF₃ | Cl |
| H | Cl | Cl | OCH₂CCl=CH₂ | Cl |
| Me | Cl | Cl | OCH₂CCl=CH₂ | Cl |
| Et | Cl | Cl | OCH₂CCl=CH₂ | Cl |
| i-Pr | Cl | Cl | OCH₂CCl=CH₂ | Cl |
| t-Bu | Cl | Cl | OCH₂CCl=CH₂ | Cl |
| c-Pr | Cl | Cl | OCH₂CCl=CH₂ | Cl |
| H | Cl | Cl | OCH₂CH=CF₂ | Cl |
| Me | Cl | Cl | OCH₂CH=CF₂ | Cl |
| Et | Cl | Cl | OCH₂CH=CF₂ | Cl |
| i-Pr | Cl | Cl | OCH₂CH=CF₂ | Cl |
| t-Bu | Cl | Cl | OCH₂CH=CF₂ | Cl |
| c-Pr | Cl | Cl | OCH₂CH=CF₂ | Cl |
| H | Cl | Cl | OCH₂CCl=CHCl | Cl |
| Me | Cl | Cl | OCH₂CCl=CHCl | Cl |
| Et | Cl | Cl | OCH₂CCl=CHCl | Cl |
| i-Pr | Cl | Cl | OCH₂CCl=CHCl | Cl |
| t-Bu | Cl | Cl | OCH₂CCl=CHCl | Cl |
| c-Pr | Cl | Cl | OCH₂CCl=CHCl | Cl |
| H | Cl | Cl | NHS(O)₂CF₃ | Cl |
| Me | Cl | Cl | NHS(O)₂CF₃ | Cl |
| Et | Cl | Cl | NHS(O)₂CF₃ | Cl |
| i-Pr | Cl | Cl | NHS(O)₂CF₃ | Cl |
| t-Bu | Cl | Cl | NHS(O)₂CF₃ | Cl |
| c-Pr | Cl | Cl | NHS(O)₂CF₃ | Cl |
| H | Cl | Cl | NHCOCF₃ | Cl |
| Me | Cl | Cl | NHCOCF₃ | Cl |
| Et | Cl | Cl | NHCOCF₃ | Cl |
| i-Pr | Cl | Cl | NHCOCF₃ | Cl |
| t-Bu | Cl | Cl | NHCOCF₃ | Cl |
| c-Pr | Cl | Cl | NHCOCF₃ | Cl |
| H | Cl | Cl | SCH₂CCl=CH₂ | Cl |
| Me | Cl | Cl | SCH₂CCl=CH₂ | Cl |
| Et | Cl | Cl | SCH₂CCl=CH₂ | Cl |
| i-Pr | Cl | Cl | SCH₂CCl=CH₂ | Cl |
| t-Bu | Cl | Cl | SCH₂CCl=CH₂ | Cl |
| c-Pr | Cl | Cl | SCH₂CCl=CH₂ | Cl |
| H | Cl | Cl | OCH₂CN | Cl |
| Me | Cl | Cl | OCH₂CN | Cl |
| Et | Cl | Cl | OCH₂CN | Cl |
| i-Pr | Cl | Cl | OCH₂CN | Cl |
| t-Bu | Cl | Cl | OCH₂CN | Cl |
| c-Pr | Cl | Cl | OCH₂CN | Cl |
| H | Cl | Cl | OCH₂NO₂ | Cl |
| Me | Cl | Cl | OCH₂NO₂ | Cl |
| Et | Cl | Cl | OCH₂NO₂ | Cl |
| i-Pr | Cl | Cl | OCH₂NO₂ | Cl |
| t-Bu | Cl | Cl | OCH₂NO₂ | Cl |
| c-Pr | Cl | Cl | OCH₂NO₂ | Cl |
| H | Cl | Cl | OCH₂NMe₂ | Cl |
| Me | Cl | Cl | OCH₂NMe₂ | Cl |
| Et | Cl | Cl | OCH₂NMe₂ | Cl |

TABLE 2-continued

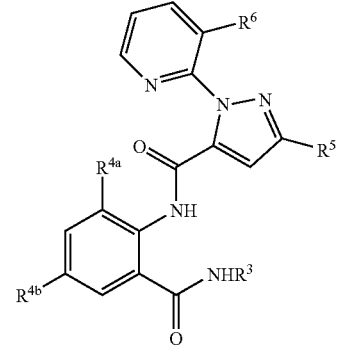

| R³ | R⁴ᵃ | R⁴ᵇ | R⁵ | R⁶ |
|---|---|---|---|---|
| i-Pr | Cl | Cl | OCH₂NMe₂ | Cl |
| t-Bu | Cl | Cl | OCH₂NMe₂ | Cl |
| c-Pr | Cl | Cl | OCH₂NMe₂ | Cl |
| H | Cl | Cl | OCH₂NHMe | Cl |
| Me | Cl | Cl | OCH₂NHMe | Cl |
| Et | Cl | Cl | OCH₂NHMe | Cl |
| i-Pr | Cl | Cl | OCH₂NHMe | Cl |
| t-Bu | Cl | Cl | OCH₂NHMe | Cl |
| c-Pr | Cl | Cl | OCH₂NHMe | Cl |
| H | Me | Cl | OCH₂-c-Pr | Cl |
| Me | Me | Cl | OCH₂-c-Pr | Cl |
| Et | Me | Cl | OCH₂-c-Pr | Cl |
| i-Pr | Me | Cl | OCH₂-c-Pr | Cl |
| i-Bu | Me | Cl | OCH₂-c-Pr | Cl |
| c-Pr | Me | Cl | OCH₂-c-Pr | Cl |
| H | Cl | Cl | O-c-Pr | Cl |
| Me | Cl | Cl | O-c-Pr | Cl |
| Et | Cl | Cl | O-c-Pr | Cl |
| i-Pr | Cl | Cl | O-c-Pr | Cl |
| t-Bu | Cl | Cl | O-c-Pr | Cl |
| c-Pr | Cl | Cl | O-c-Pr | Cl |
| H | Cl | Cl | CH₂OCHF₂ | Cl |
| Me | Cl | Cl | CH₂OCHF₂ | Cl |
| Et | Cl | Cl | CH₂OCHF₂ | Cl |
| i-Pr | Cl | Cl | CH₂OCHF₂ | Cl |
| t-Bu | Cl | Cl | CH₂OCHF₂ | Cl |
| c-Pr | Cl | Cl | CH₂OCHF₂ | Cl |
| H | Cl | Cl | CH₂SCHF₂ | Cl |
| Me | Cl | Cl | CH₂SCHF₂ | Cl |
| Et | Cl | Cl | CH₂SCHF₂ | Cl |
| i-Pr | Cl | Cl | CH₂SCHF₂ | Cl |
| t-Bu | Cl | Cl | CH₂SCHF₂ | Cl |
| c-Pr | Cl | Cl | CH₂SCHF₂ | Cl |
| H | Cl | Cl | CH₂S(O)₂CHF₂ | Cl |
| Me | Cl | Cl | CH₂S(O)₂CHF₂ | Cl |
| Et | Cl | Cl | CH₂S(O)₂CHF₂ | Cl |
| i-Pr | Cl | Cl | CH₂S(O)₂CHF₂ | Cl |
| t-Bu | Cl | Cl | CH₂S(O)₂CHF₂ | Cl |
| c-Pr | Cl | Cl | CH₂S(O)₂CHF₂ | Cl |
| H | Me | Cl | 2,2-di-F-c-PrO | Cl |
| Me | Me | Cl | 2,2-di-F-c-PrO | Cl |
| Et | Me | Cl | 2,2-di-F-c-PrO | Cl |
| i-Pr | Me | Cl | 2,2-di-F-c-PrO | Cl |
| t-Bu | Me | Cl | 2,2-di-F-c-PrO | Cl |
| c-Pr | Me | Cl | 2,2-di-F-c-PrO | Cl |
| H | Me | Cl | 2,2,3,3-tetra-F-c-PrO | Cl |
| Me | Me | Cl | 2,2,3,3-tetra-F-c-PrO | Cl |
| Et | Me | Cl | 2,2,3,3-tetra-F-c-PrO | Cl |
| i-Pr | Me | Cl | 2,2,3,3-tetra-F-c-PrO | Cl |
| t-Bu | Me | Cl | 2,2,3,3-tetra-F-c-PrO | Cl |
| c-Pr | Me | Cl | 2,2,3,3-tetra-F-c-PrO | Cl |
| H | Me | Cl | 2,2-di-F-c-PrCH₂O | Cl |
| Me | Me | Cl | 2,2-di-F-c-PrCH₂O | Cl |
| Et | Me | Cl | 2,2-di-F-c-PrCH₂O | Cl |
| i-Pr | Me | Cl | 2,2-di-F-c-PrCH₂O | Cl |
| t-Bu | Me | Cl | 2,2-di-F-c-PrCH₂O | Cl |
| c-Pr | Me | Cl | 2,2-di-F-c-PrCH₂O | Cl |

TABLE 3

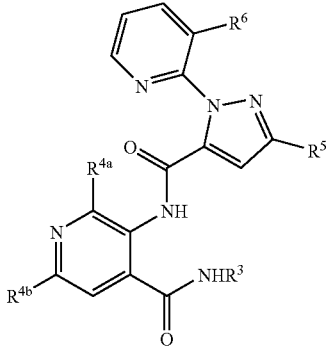

| R³ | R⁴ᵃ | R⁴ᵇ | R⁵ | R⁶ |
|---|---|---|---|---|
| H | Me | H | CF₂OMe | Cl |
| Me | Me | H | CF₂OMe | Cl |
| Et | Me | H | CF₂OMe | Cl |
| i-Pr | Me | H | CF₂OMe | Cl |
| t-Bu | Me | H | CF₂OMe | Cl |
| c-Pr | Me | H | CF₂OMe | Cl |
| H | Me | H | CF₂OMe | F |
| Me | Me | H | CF₂OMe | F |
| Et | Me | H | CF₂OMe | F |
| i-Pr | Me | H | CF₂OMe | F |
| t-Bu | Me | H | CF₂OMe | F |
| c-Pr | Me | H | CF₂OMe | F |
| H | Cl | H | CF₂OMe | Cl |
| Me | Cl | H | CF₂OMe | Cl |
| Et | Cl | H | CF₂OMe | Cl |
| i-Pr | Cl | H | CF₂OMe | Cl |
| t-Bu | Cl | H | CF₂OMe | Cl |
| c-Pr | Cl | H | CF₂OMe | Cl |
| H | Cl | H | CF₂OMe | F |
| Me | Cl | H | CF₂OMe | F |
| Et | Cl | H | CF₂OMe | F |
| i-Pr | Cl | H | CF₂OMe | F |
| t-Bu | Cl | H | CF₂OMe | F |
| c-Pr | Cl | H | CF₂OMe | F |
| H | Me | Cl | CF₂OMe | Cl |
| Me | Me | Cl | CF₂OMe | Cl |
| Et | Me | Cl | CF₂OMe | Cl |
| i-Pr | Me | Cl | CF₂OMe | Cl |
| t-Bu | Me | Cl | CF₂OMe | Cl |
| c-Pr | Me | Cl | CF₂OMe | Cl |
| H | Me | Cl | CF₂OMe | F |
| Me | Me | Cl | CF₂OMe | F |
| Et | Me | Cl | CF₂OMe | F |
| i-Pr | Me | Cl | CF₂OMe | F |
| t-Bu | Me | Cl | CF₂OMe | F |
| c-Pr | Me | Cl | CF₂OMe | F |
| Me | Me | Br | CF₂OMe | Cl |
| Et | Me | Br | CF₂OMe | Cl |
| i-Pr | Me | Br | CF₂OMe | Cl |
| t-Bu | Me | Br | CF₂OMe | Cl |
| c-Pr | Me | Br | CF₂OMe | Cl |
| H | Me | Br | CF₂OMe | F |
| Me | Me | Br | CF₂OMe | F |
| Et | Me | Br | CF₂OMe | F |
| i-Pr | Me | Br | CF₂OMe | F |
| t-Bu | Me | Br | CF₂OMe | F |
| c-Pr | Me | Br | CF₂OMe | F |
| H | Cl | Cl | CF₂OMe | Cl |
| Me | Cl | Cl | CF₂OMe | Cl |
| Et | Cl | Cl | CF₂OMe | Cl |
| i-Pr | Cl | Cl | CF₂OMe | Cl |
| t-Bu | Cl | Cl | CF₂OMe | Cl |
| c-Pr | Cl | Cl | CF₂OMe | Cl |
| H | Cl | Cl | CF₂OMe | F |
| Me | Cl | Cl | CF₂OMe | F |
| Et | Cl | Cl | CF₂OMe | F |
| i-Pr | Cl | Cl | CF₂OMe | F |
| t-Bu | Cl | Cl | CF₂OMe | F |
| c-Pr | Cl | Cl | CF₂OMe | F |

TABLE 3-continued

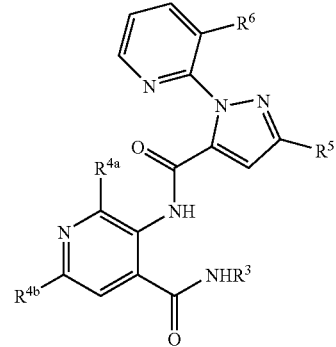

| R³ | R⁴ᵃ | R⁴ᵇ | R⁵ | R⁶ |
|---|---|---|---|---|
| H | Me | CN | CF₂OMe | Cl |
| Me | Me | CN | CF₂OMe | Cl |
| Et | Me | CN | CF₂OMe | Cl |
| i-Pr | Me | CN | CF₂OMe | Cl |
| t-Bu | Me | CN | CF₂OMe | Cl |
| c-Pr | Me | CN | CF₂OMe | Cl |
| H | Me | CN | CF₂OMe | F |
| Me | Me | CN | CF₂OMe | F |
| Et | Me | CN | CF₂OMe | F |
| i-Pr | Me | CN | CF₂OMe | F |
| t-Bu | Me | CN | CF₂OMe | F |
| c-Pr | Me | CN | CF₂OMe | F |
| H | Me | Cl | CF₂OMe | CF₃ |
| Me | Me | Cl | CF₂OMe | CF₃ |
| Et | Me | Cl | CF₂OMe | CF₃ |
| i-Pr | Me | Cl | CF₂OMe | CF₃ |
| t-Bu | Me | Cl | CF₂OMe | CF₃ |
| c-Pr | Me | Cl | CF₂OMe | CF₃ |
| H | Me | Cl | CF₂OMe | CN |
| Me | Me | Cl | CF₂OMe | CN |
| Et | Me | Cl | CF₂OMe | CN |
| i-Pr | Me | Cl | CF₂OMe | CN |
| t-Bu | Me | Cl | CF₂OMe | CN |
| c-Pr | Me | Cl | CF₂OMe | CN |
| H | Me | I | CF₂OMe | Cl |
| Me | Me | I | CF₂OMe | Cl |
| Et | Me | I | CF₂OMe | Cl |
| i-Pr | Me | I | CF₂OMe | Cl |
| t-Bu | Me | I | CF₂OMe | Cl |
| c-Pr | Me | I | CF₂OMe | Cl |
| H | Me | F | CF₂OMe | Cl |
| Me | Me | F | CF₂OMe | Cl |
| Et | Me | F | CF₂OMe | Cl |
| i-Pr | Me | F | CF₂OMe | Cl |
| t-Bu | Me | F | CF₂OMe | Cl |
| c-Pr | Me | F | CF₂OMe | Cl |
| H | Br | Cl | CF₂OMe | Cl |
| Me | Br | Cl | CF₂OMe | Cl |
| Et | Br | Cl | CF₂OMe | Cl |
| i-Pr | Br | Cl | CF₂OMe | Cl |
| t-Bu | Br | Cl | CF₂OMe | Cl |
| c-Pr | Br | Cl | CF₂OMe | Cl |
| H | Cl | Br | CF₂OMe | Cl |
| Me | Cl | Br | CF₂OMe | Cl |
| Et | Cl | Br | CF₂OMe | Cl |
| i-Pr | Cl | Br | CF₂OMe | Cl |
| t-Bu | Cl | Br | CF₂OMe | Cl |
| c-Pr | Cl | Br | CF₂OMe | Cl |
| H | Me | Cl | CF₂SMe | Cl |
| Me | Me | Cl | CF₂SMe | Cl |
| Et | Me | Cl | CF₂SMe | Cl |
| i-Pr | Me | Cl | CF₂SMe | Cl |
| t-Bu | Me | Cl | CF₂SMe | Cl |
| c-Pr | Me | Cl | CF₂SMe | Cl |
| H | Me | Cl | CF₂S(O)Me | Cl |
| Me | Me | Cl | CF₂S(O)Me | Cl |
| Et | Me | Cl | CF₂S(O)Me | Cl |
| i-Pr | Me | Cl | CF₂S(O)Me | Cl |
| t-Bu | Me | Cl | CF₂S(O)Me | Cl |

TABLE 3-continued

| R³ | R⁴ᵃ | R⁴ᵇ | R⁵ | R⁶ |
|---|---|---|---|---|
| c-Pr | Me | Cl | CF₂S(O)Me | Cl |
| H | Me | Cl | CF₂S(O)₂Me | Cl |
| Me | Me | Cl | CF₂S(O)₂Me | Cl |
| Et | Me | Cl | CF₂S(O)₂Me | Cl |
| i-Pr | Me | Cl | CF₂S(O)₂Me | Cl |
| t-Bu | Me | Cl | CF₂S(O)₂Me | Cl |
| c-Pr | Me | Cl | CF₂S(O)₂Me | Cl |
| H | Me | H | CH₂OMe | Cl |
| Me | Me | H | CH₂OMe | Cl |
| Et | Me | H | CH₂OMe | Cl |
| i-Pr | Me | H | CH₂OMe | Cl |
| t-Bu | Me | H | CH₂OMe | Cl |
| c-Pr | Me | H | CH₂OMe | Cl |
| H | Cl | H | CH₂OMe | Cl |
| Me | Cl | H | CH₂OMe | Cl |
| Et | Cl | H | CH₂OMe | Cl |
| i-Pr | Cl | H | CH₂OMe | Cl |
| r-Bu | Cl | H | CH₂OMe | Cl |
| c-Pr | Cl | H | CH₂OMe | Cl |
| H | Me | Cl | CH₂OMe | Cl |
| Me | Me | Cl | CH₂OMe | Cl |
| Et | Me | Cl | CH₂OMe | Cl |
| i-Pr | Me | Cl | CH₂OMe | Cl |
| t-Bu | Me | Cl | CH₂OMe | Cl |
| c-Pr | Me | Cl | CH₂OMe | Cl |
| H | Me | H | CH₂SMe | Cl |
| Me | Me | H | CH₂SMe | Cl |
| Et | Me | H | CH₂SMe | Cl |
| i-Pr | Me | H | CH₂SMe | Cl |
| t-Bu | Me | H | CH₂SMe | Cl |
| c-Pr | Me | H | CH₂SMe | Cl |
| H | Cl | H | CH₂SMe | Cl |
| Me | Cl | H | CH₂SMe | Cl |
| Et | Cl | H | CH₂SMe | Cl |
| i-Pr | Cl | H | CH₂SMe | Cl |
| t-Bu | Cl | H | CH₂SMe | Cl |
| c-Pr | Cl | H | CH₂SMe | Cl |
| H | Me | Cl | CH₂SMe | Cl |
| Me | Me | Cl | CH₂SMe | Cl |
| Et | Me | Cl | CH₂SMe | Cl |
| i-Pr | Me | Cl | CH₂SMe | Cl |
| t-Bu | Me | Cl | CH₂SMe | Cl |
| c-Pr | Me | Cl | CH₂SMe | Cl |
| H | Me | Cl | CH₂S(O)Me | Cl |
| Me | Me | Cl | CH₂S(O)Me | Cl |
| Et | Me | Cl | CH₂S(O)Me | Cl |
| i-Pr | Me | Cl | CH₂S(O)Me | Cl |
| t-Bu | Me | Cl | CH₂S(O)Me | Cl |
| c-Pr | Me | Cl | CH₂S(O)Me | Cl |
| H | Me | Cl | CH₂S(O)₂Me | Cl |
| Me | Me | Cl | CH₂S(O)₂Me | Cl |
| Et | Me | Cl | CH₂S(O)₂Me | Cl |
| i-Pr | Me | Cl | CH₂S(O)₂Me | Cl |
| t-Bu | Me | Cl | CH₂S(O)₂Me | Cl |
| c-Pr | Me | Cl | CH₂S(O)₂Me | Cl |
| H | Me | H | OS(O)₂Me | Cl |
| Me | Me | H | OS(O)₂Me | Cl |
| Et | Me | H | OS(O)₂Me | Cl |
| i-Pr | Me | H | OS(O)₂Me | Cl |
| t-Bu | Me | H | OS(O)₂Me | Cl |
| c-Pr | Me | H | OS(O)₂Me | Cl |
| H | Cl | H | OS(O)₂Me | Cl |
| Me | Cl | H | OS(O)₂Me | Cl |
| Et | Cl | H | OS(O)₂Me | Cl |
| i-Pr | Cl | H | OS(O)₂Me | Cl |
| t-Bu | Cl | H | OS(O)₂Me | Cl |
| c-Pr | Cl | H | OS(O)₂Me | Cl |
| H | Me | Cl | OS(O)₂Me | Cl |
| Me | Me | Cl | OS(O)₂Me | Cl |
| Et | Me | Cl | OS(O)₂Me | Cl |
| i-Pr | Me | Cl | OS(O)₂Me | Cl |
| t-Bu | Me | Cl | OS(O)₂Me | Cl |
| c-Pr | Me | Cl | OS(O)₂Me | Cl |
| H | Me | H | OS(O)₂CF₃ | Cl |
| Me | Me | H | OS(O)₂CF₃ | Cl |
| Et | Me | H | OS(O)₂CF₃ | Cl |
| i-Pr | Me | H | OS(O)₂CF₃ | Cl |
| t-Bu | Me | H | OS(O)₂CF₃ | Cl |
| c-Pr | Me | H | OS(O)₂CF₃ | Cl |
| H | Cl | H | OS(O)₂CF₃ | Cl |
| Me | Cl | H | OS(O)₂CF₃ | Cl |
| Et | Cl | H | OS(O)₂CF₃ | Cl |
| i-Pr | Cl | H | OS(O)₂CF₃ | Cl |
| t-Bu | Cl | H | OS(O)₂CF₃ | Cl |
| c-Pr | Cl | H | OS(O)₂CF₃ | Cl |
| H | Me | Cl | OS(O)₂CClF₂ | Cl |
| Me | Me | Cl | OS(O)₂CClF₂ | Cl |
| Et | Me | Cl | OS(O)₂CClF₂ | Cl |
| i-Pr | Me | Cl | OS(O)₂CClF₂ | Cl |
| i-Bu | Me | Cl | OS(O)₂CClF₂ | Cl |
| c-Pr | Me | Cl | OS(O)₂CClF₂ | Cl |
| H | Me | Cl | OCH₂C≡CH | Cl |
| Me | Me | Cl | OCH₂C≡CH | Cl |
| Et | Me | Cl | OCH₂C≡CH | Cl |
| i-Pr | Me | Cl | OCH₂C≡CH | Cl |
| t-Bu | Me | Cl | OCH₂C≡CH | Cl |
| c-Pr | Me | Cl | OCH₂C≡CH | Cl |
| H | Me | Cl | OCH₂CH=CH₂ | Cl |
| Me | Me | Cl | OCH₂CH=CH₂ | Cl |
| Et | Me | Cl | OCH₂CH=CH₂ | Cl |
| i-Pr | Me | Cl | OCH₂CH=CH₂ | Cl |
| t-Bu | Me | Cl | OCH₂CH=CH₂ | Cl |
| c-Pr | Me | Cl | OCH₂CH=CH₂ | Cl |
| H | Me | Cl | NHCH₂CF₃ | Cl |
| Me | Me | Cl | NHCH₂CF₃ | Cl |
| Et | Me | Cl | NHCH₂CF₃ | Cl |
| i-Pr | Me | Cl | NHCH₂CF₃ | Cl |
| t-Bu | Me | Cl | NHCH₂CF₃ | Cl |
| c-Pr | Me | Cl | NHCH₂CF₃ | Cl |
| H | Me | Cl | OCH₂CCl=CH₂ | Cl |
| Me | Me | Cl | OCH₂CCl=CH₂ | Cl |
| Et | Me | Cl | OCH₂CCl=CH₂ | Cl |
| i-Pr | Me | Cl | OCH₂CCl=CH₂ | Cl |
| i-Et | Me | Cl | OCH₂CCl=CH₂ | Cl |
| c-Pr | Me | Cl | OCH₂CCl=CH₂ | Cl |
| H | Me | Cl | OCH₂CH=CF₂ | Cl |
| Me | Me | Cl | OCH₂CH=CF₂ | Cl |
| Et | Me | Cl | OCH₂CH=CF₂ | Cl |

TABLE 3-continued

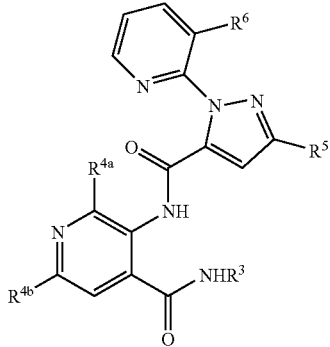

| R³ | R⁴ᵃ | R⁴ᵇ | R⁵ | R⁶ |
|---|---|---|---|---|
| i-Pr | Me | Cl | OCH₂CH=CF₂ | Cl |
| i-Et | Me | Cl | OCH₂CH=CF₂ | Cl |
| c-Pr | Me | Cl | OCH₂CH=CF₂ | Cl |
| H | Me | Cl | NHS(O)₂CF₃ | Cl |
| Me | Me | Cl | NHS(O)₂CF₃ | Cl |
| Et | Me | Cl | NHS(O)₂CF₃ | Cl |
| i-Pr | Me | Cl | NHS(O)₂CF₃ | Cl |
| t-Bu | Me | Cl | NHS(O)₂CF₃ | Cl |
| c-Pr | Me | Cl | NHS(O)₂CF₃ | Cl |
| H | Me | Cl | NHCOCF₃ | Cl |
| Me | Me | Cl | NHCOCF₃ | Cl |
| Et | Me | Cl | NHCOCF₃ | Cl |
| i-Pr | Me | Cl | NHCOCF₃ | Cl |
| t-Bu | Me | Cl | NHCOCF₃ | Cl |
| c-Pr | Me | Cl | NHCOCF₃ | Cl |
| H | Me | Cl | OCH₂CN | Cl |
| Me | Me | Cl | OCH₂CN | Cl |
| Et | Me | Cl | OCH₂CN | Cl |
| i-Pr | Me | Cl | OCH₂CN | Cl |
| t-Bu | Me | Cl | OCH₂CN | Cl |
| c-Pr | Me | Cl | OCH₂CN | Cl |
| H | Me | Cl | OCH₂NO₂ | Cl |
| Me | Me | Cl | OCH₂NO₂ | Cl |
| Et | Me | Cl | OCH₂NO₂ | Cl |
| i-Pr | Me | Cl | OCH₂NO₂ | Cl |
| t-Bu | Me | Cl | OCH₂NO₂ | Cl |
| c-Pr | Me | Cl | OCH₂NO₂ | Cl |
| H | Me | Cl | O-c-Pr | Cl |
| Me | Me | Cl | O-c-Pr | Cl |
| Et | Me | Cl | O-c-Pr | Cl |
| i-Pr | Me | Cl | O-c-Pr | Cl |
| t-Bu | Me | Cl | O-c-Pr | Cl |
| c-Pr | Me | Cl | O-c-Pr | Cl |
| H | Me | Cl | CH₂OCHF₂ | Cl |
| Me | Me | Cl | CH₂OCHF₂ | Cl |
| Et | Me | Cl | CH₂OCHF₂ | Cl |
| i-Pr | Me | Cl | CH₂OCHF₂ | Cl |
| t-Bu | Me | Cl | CH₂OCHF₂ | Cl |
| c-Pr | Me | Cl | CH₂OCHF₂ | Cl |
| H | Me | Cl | CH₂SCHF₂ | Cl |
| Me | Me | Cl | CH₂SCHF₂ | Cl |
| Et | Me | Cl | CH₂SCHF₂ | Cl |
| i-Pr | Me | Cl | CH₂SCHF₂ | Cl |
| t-Bu | Me | Cl | CH₂SCHF₂ | Cl |
| c-Pr | Me | Cl | CH₂SCHF₂ | Cl |
| H | Me | Cl | CH₂S(O)₂CHF₂ | Cl |
| Me | Me | Cl | CH₂S(O)₂CHF₂ | Cl |
| Et | Me | Cl | CH₂S(O)₂CHF₂ | Cl |
| i-Pr | Me | Cl | CH₂S(O)₂CHF₂ | Cl |
| t-Bu | Me | Cl | CH₂S(O)₂CHF₂ | Cl |
| c-Pr | Me | Cl | CH₂S(O)₂CHF₂ | Cl |
| H | Me | H | CF₂OEt | Cl |
| Me | Me | H | CF₂OEt | Cl |
| Et | Me | H | CF₂OEt | Cl |
| i-Pr | Me | H | CF₂OEt | Cl |
| t-Bu | Me | H | CF₂OEt | Cl |
| c-Pr | Me | H | CF₂OEt | Cl |
| H | Me | H | CF₂OEt | F |
| Me | Me | H | CF₂OEt | F |

TABLE 3-continued

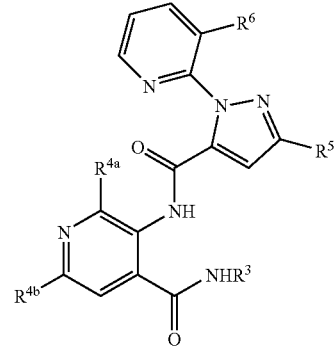

| R³ | R⁴ᵃ | R⁴ᵇ | R⁵ | R⁶ |
|---|---|---|---|---|
| Et | Me | H | CF₂OEt | F |
| i-Pr | Me | H | CF₂OEt | F |
| t-Bu | Me | H | CF₂OEt | F |
| c-Pr | Me | H | CF₂OEt | F |
| H | Cl | H | CF₂OEt | Cl |
| Me | Cl | H | CF₂OEt | Cl |
| Et | Cl | H | CF₂OEt | Cl |
| i-Pr | Cl | H | CF₂OEt | Cl |
| t-Bu | Cl | H | CF₂OEt | Cl |
| c-Pr | Cl | H | CF₂OEt | Cl |
| H | Cl | H | CF₂OEt | F |
| Me | Cl | H | CF₂OEt | F |
| Et | Cl | H | CF₂OEt | F |
| i-Pr | Cl | H | CF₂OEt | F |
| t-Bu | Cl | H | CF₂OEt | F |
| c-Pr | Cl | H | CF₂OEt | F |
| H | Me | Cl | CF₂OEt | Cl |
| Me | Me | Cl | CF₂OEt | Cl |
| Et | Me | Cl | CF₂OEt | Cl |
| i-Pr | Me | Cl | CF₂OEt | Cl |
| t-Bu | Me | Cl | CF₂OEt | Cl |
| c-Pr | Me | Cl | CF₂OEt | Cl |
| H | Me | Cl | CF₂OEt | F |
| Me | Me | Cl | CF₂OEt | F |
| Et | Me | Cl | CF₂OEt | F |
| i-Pr | Me | Cl | CF₂OEt | F |
| t-Bu | Me | Cl | CF₂OEt | F |
| c-Pr | Me | Cl | CF₂OEt | F |
| Me | Me | Br | CF₂OEt | Cl |
| Et | Me | Br | CF₂OEt | Cl |
| i-Pr | Me | Br | CF₂OEt | Cl |
| t-Bu | Me | Br | CF₂OEt | Cl |
| c-Pr | Me | Br | CF₂OEt | Cl |
| H | Me | Br | CF₂OEt | F |
| Me | Me | Br | CF₂OEt | F |
| Et | Me | Br | CF₂OEt | F |
| i-Pr | Me | Br | CF₂OEt | F |
| t-Bu | Me | Br | CF₂OEt | F |
| c-Pr | Me | Br | CF₂OEt | F |
| H | Cl | Cl | CF₂OEt | Cl |
| Me | Cl | Cl | CF₂OEt | Cl |
| Et | Cl | Cl | CF₂OEt | Cl |
| i-Pr | Cl | Cl | CF₂OEt | Cl |
| t-Bu | Cl | Cl | CF₂OEt | Cl |
| c-Pr | Cl | Cl | CF₂OEt | Cl |
| H | Cl | Cl | CF₂OEt | F |
| Me | Cl | Cl | CF₂OEt | F |
| Et | Cl | Cl | CF₂OEt | F |
| i-Pr | Cl | Cl | CF₂OEt | F |
| t-Bu | Cl | Cl | CF₂OEt | F |
| c-Pr | Cl | Cl | CF₂OEt | F |
| H | Me | CN | CF₂OEt | Cl |
| Me | Me | CN | CF₂OEt | Cl |
| Et | Me | CN | CF₂OEt | Cl |
| i-Pr | Me | CN | CF₂OEt | Cl |
| t-Bu | Me | CN | CF₂OEt | Cl |
| c-Pr | Me | CN | CF₂OEt | Cl |
| H | Me | CN | CF₂OEt | F |
| Me | Me | CN | CF₂OEt | F |

TABLE 3-continued

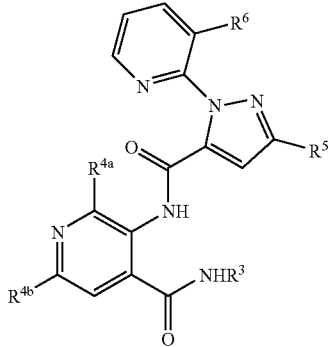

| R³ | R⁴ᵃ | R⁴ᵇ | R⁵ | R⁶ |
|---|---|---|---|---|
| Et | Me | CN | CF₂OEt | F |
| i-Pr | Me | CN | CF₂OEt | F |
| t-Bu | Me | CN | CF₂OEt | F |
| c-Pr | Me | CN | CF₂OEt | F |
| H | Me | Cl | CF₂OEt | CF₃ |
| Me | Me | Cl | CF₂OEt | CF₃ |
| Et | Me | Cl | CF₂OEt | CF₃ |
| i-Pr | Me | Cl | CF₂OEt | CF₃ |
| t-Bu | Me | Cl | CF₂OEt | CF₃ |
| c-Pr | Me | Cl | CF₂OEt | CF₃ |
| H | Me | Cl | CF₂OEt | CN |
| Me | Me | Cl | CF₂OEt | CN |
| Et | Me | Cl | CF₂OEt | CN |
| i-Pr | Me | Cl | CF₂OEt | CN |
| t-Bu | Me | Cl | CF₂OEt | CN |
| c-Pr | Me | Cl | CF₂OEt | CN |
| H | Me | I | CF₂OEt | Cl |
| Me | Me | I | CF₂OEt | Cl |
| Et | Me | I | CF₂OEt | Cl |
| i-Pr | Me | I | CF₂OEt | Cl |
| t-Bu | Me | I | CF₂OEt | Cl |
| c-Pr | Me | I | CF₂OEt | Cl |
| H | Me | F | CF₂OEt | Cl |
| Me | Me | F | CF₂OEt | Cl |
| Et | Me | F | CF₂OEt | Cl |
| i-Pr | Me | F | CF₂OEt | Cl |
| t-Bu | Me | F | CF₂OEt | Cl |
| c-Pr | Me | F | CF₂OEt | Cl |
| H | Br | Cl | CF₂OEt | Cl |
| Me | Br | Cl | CF₂OEt | Cl |
| Et | Br | Cl | CF₂OEt | Cl |
| i-Pr | Br | Cl | CF₂OEt | Cl |
| t-Bu | Br | Cl | CF₂OEt | Cl |
| c-Pr | Br | Cl | CF₂OEt | Cl |
| H | Cl | Br | CF₂OEt | Cl |
| Me | Cl | Br | CF₂OEt | Cl |
| Et | Cl | Br | CF₂OEt | Cl |
| i-Pr | Cl | Br | CF₂OEt | Cl |
| t-Bu | Cl | Br | CF₂OEt | Cl |
| c-Pr | Cl | Br | CF₂OEt | Cl |
| H | Me | Cl | CF₂SEt | Cl |
| Me | Me | Cl | CF₂SEt | Cl |
| Et | Me | Cl | CF₂SEt | Cl |
| i-Pr | Me | Cl | CF₂SEt | Cl |
| t-Bu | Me | Cl | CF₂SEt | Cl |
| c-Pr | Me | Cl | CF₂SEt | Cl |
| H | Me | Cl | CF₂S(O)Et | Cl |
| Me | Me | Cl | CF₂S(O)Et | Cl |
| Et | Me | Cl | CF₂S(O)Et | Cl |
| i-Pr | Me | Cl | CF₂S(O)Et | Cl |
| t-Bu | Me | Cl | CF₂S(O)Et | Cl |
| c-Pr | Me | Cl | CF₂S(O)Et | Cl |
| H | Me | Cl | CF₂S(O)₂Et | Cl |
| Me | Me | Cl | CF₂S(O)₂Et | Cl |
| Et | Me | Cl | CF₂S(O)₂Et | Cl |
| i-Pr | Me | Cl | CF₂S(O)₂Et | Cl |
| t-Bu | Me | Cl | CF₂S(O)₂Et | Cl |
| c-Pr | Me | Cl | CF₂S(O)₂Et | Cl |
| H | Me | H | CH₂OEt | Cl |

TABLE 3-continued

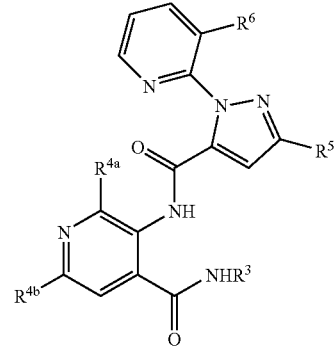

| R³ | R⁴ᵃ | R⁴ᵇ | R⁵ | R⁶ |
|---|---|---|---|---|
| Me | Me | H | CH₂OEt | Cl |
| Et | Me | H | CH₂OEt | Cl |
| i-Pr | Me | H | CH₂OEt | Cl |
| t-Bu | Me | H | CH₂OEt | Cl |
| c-Pr | Me | H | CH₂OEt | Cl |
| H | Cl | H | CH₂OEt | Cl |
| Me | Cl | H | CH₂OEt | Cl |
| Et | Cl | H | CH₂OEt | Cl |
| i-Pr | Cl | H | CH₂OEt | Cl |
| t-Bu | Cl | H | CH₂OEt | Cl |
| c-Pr | Cl | H | CH₂OEt | Cl |
| H | Me | Cl | CH₂OEt | Cl |
| Me | Me | Cl | CH₂OEt | Cl |
| Et | Me | Cl | CH₂OEt | Cl |
| i-Pr | Me | Cl | CH₂OEt | Cl |
| t-Bu | Me | Cl | CH₂OEt | Cl |
| c-Pr | Me | Cl | CH₂OEt | Cl |
| H | Me | H | CH₂SEt | Cl |
| Me | Me | H | CH₂SEt | Cl |
| Et | Me | H | CH₂SEt | Cl |
| i-Pr | Me | H | CH₂SEt | Cl |
| t-Bu | Me | H | CH₂SEt | Cl |
| c-Pr | Me | H | CH₂SEt | Cl |
| H | Cl | H | CH₂SEt | Cl |
| Me | Cl | H | CH₂SEt | Cl |
| Et | Cl | H | CH₂SEt | Cl |
| i-Pr | Cl | H | CH₂SEt | Cl |
| t-Bu | Cl | H | CH₂SEt | Cl |
| c-Pr | Cl | H | CH₂SEt | Cl |
| H | Me | Cl | CH₂SEt | Cl |
| Me | Me | Cl | CH₂SEt | Cl |
| Et | Me | Cl | CH₂SEt | Cl |
| i-Pr | Me | Cl | CH₂SEt | Cl |
| t-Bu | Me | Cl | CH₂SEt | Cl |
| c-Pr | Me | Cl | CH₂SEt | Cl |
| H | Me | Cl | CH₂S(O)Et | Cl |
| Me | Me | Cl | CH₂S(O)Et | Cl |
| Et | Me | Cl | CH₂S(O)Et | Cl |
| i-Pr | Me | Cl | CH₂S(O)Et | Cl |
| t-Bu | Me | Cl | CH₂S(O)Et | Cl |
| c-Pr | Me | Cl | CH₂S(O)Et | Cl |
| H | Me | Cl | CH₂S(O)₂Et | Cl |
| Me | Me | Cl | CH₂S(O)₂Et | Cl |
| Et | Me | Cl | CH₂S(O)₂Et | Cl |
| i-Pr | Me | Cl | CH₂S(O)₂Et | Cl |
| t-Bu | Me | Cl | CH₂S(O)₂Et | Cl |
| c-Pr | Me | Cl | CH₂S(O)₂Et | Cl |
| H | Me | H | OS(O)₂Et | Cl |
| Me | Me | H | OS(O)₂Et | Cl |
| Et | Me | H | OS(O)₂Et | Cl |
| i-Pr | Me | H | OS(O)₂Et | Cl |
| t-Bu | Me | H | OS(O)₂Et | Cl |
| c-Pr | Me | H | OS(O)₂Et | Cl |
| H | Cl | H | OS(O)₂Et | Cl |
| Me | Cl | H | OS(O)₂Et | Cl |
| Et | Cl | H | OS(O)₂Et | Cl |
| i-Pr | Cl | H | OS(O)₂Et | Cl |
| t-Bu | Cl | H | OS(O)₂Et | Cl |
| c-Pr | Cl | H | OS(O)₂Et | Cl |

TABLE 3-continued

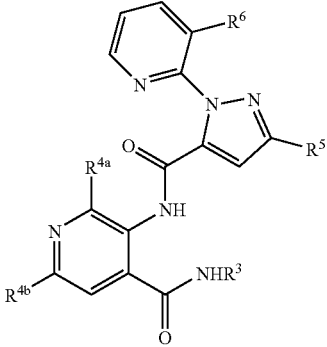

| R³ | R⁴ᵃ | R⁴ᵇ | R⁵ | R⁶ |
|---|---|---|---|---|
| H | Me | Cl | OS(O)₂Et | Cl |
| Me | Me | Cl | OS(O)₂Et | Cl |
| Et | Me | Cl | OS(O)₂Et | Cl |
| i-Pr | Me | Cl | OS(O)₂Et | Cl |
| t-Bu | Me | Cl | OS(O)₂Et | Cl |
| c-Pr | Me | Cl | OS(O)₂Et | Cl |
| H | Me | Cl | OS(O)₂CF₃ | Cl |
| Me | Me | Cl | OS(O)₂CF₃ | Cl |
| Et | Me | Cl | OS(O)₂CF₃ | Cl |
| i-Pr | Me | Cl | OS(O)₂CF₃ | Cl |
| t-Bu | Me | Cl | OS(O)₂CF₃ | Cl |
| c-Pr | Me | Cl | OS(O)₂CF₃ | Cl |
| H | Cl | Cl | OS(O)₂CF₃ | Cl |
| Me | Cl | Cl | OS(O)₂CF₃ | Cl |
| Et | Cl | Cl | OS(O)₂CF₃ | Cl |
| i-Pr | Cl | Cl | OS(O)₂CF₃ | Cl |
| i-Et | Cl | Cl | OS(O)₂CF₃ | Cl |
| c-Pr | Cl | Cl | OS(O)₂CF₃ | Cl |
| H | Me | Cl | OCOCF₃ | Cl |
| Me | Me | Cl | OCOCF₃ | Cl |
| Et | Me | Cl | OCOCF₃ | Cl |
| i-Pr | Me | Cl | OCOCF₃ | Cl |
| t-Bu | Me | Cl | OCOCF₃ | Cl |
| c-Pr | Me | Cl | OCOCF₃ | Cl |
| H | Cl | Cl | OCH₂C≡CH | Cl |
| Me | Cl | Cl | OCH₂C≡CH | Cl |
| Et | Cl | Cl | OCH₂C≡CH | Cl |
| i-Pr | Cl | Cl | OCH₂C≡CH | Cl |
| i-Et | Cl | Cl | OCH₂C≡CH | Cl |
| c-Pr | Cl | Cl | OCH₂C≡CH | Cl |
| H | Cl | Cl | OCH₂CH=CH₂ | Cl |
| Me | Cl | Cl | OCH₂CH=CH₂ | Cl |
| Et | Cl | Cl | OCH₂CH=CH₂ | Cl |
| i-Pr | Cl | Cl | OCH₂CH=CH₂ | Cl |
| t-Bu | Cl | Cl | OCH₂CH=CH₂ | Cl |
| c-Pr | Cl | Cl | OCH₂CH=CH₂ | Cl |
| H | Me | Cl | OCH₂-c-Pr | Cl |
| Me | Me | Cl | OCH₂-c-Pr | Cl |
| Et | Me | Cl | OCH₂-c-Pr | Cl |
| i-Pr | Me | Cl | OCH₂-c-Pr | Cl |
| t-Bu | Me | Cl | OCH₂-c-Pr | Cl |
| c-Pr | Me | Cl | OCH₂-c-Pr | Cl |
| H | Cl | Cl | OCH₂CCl=CH₂ | Cl |
| Me | Cl | Cl | OCH₂CCl=CH₂ | Cl |
| Et | Cl | Cl | OCH₂CCl=CH₂ | Cl |
| i-Pr | Cl | Cl | OCH₂CCl=CH₂ | Cl |
| i-Et | Cl | Cl | OCH₂CCl=CH₂ | Cl |
| c-Pr | Cl | Cl | OCH₂CCl=CH₂ | Cl |
| H | Cl | Cl | OCH₂CH=CF₂ | Cl |
| Me | Cl | Cl | OCH₂CH=CF₂ | Cl |
| Et | Cl | Cl | OCH₂CH=CF₂ | Cl |
| i-Pr | Cl | Cl | OCH₂CH=CF₂ | Cl |
| i-Et | Cl | Cl | OCH₂CH=CF₂ | Cl |
| c-Pr | Cl | Cl | OCH₂CH=CF₂ | Cl |
| H | Cl | Cl | NHS(O)₂CF₃ | Cl |

TABLE 3-continued

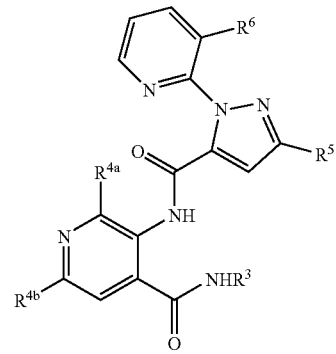

| R³ | R⁴ᵃ | R⁴ᵇ | R⁵ | R⁶ |
|---|---|---|---|---|
| Me | Cl | Cl | NHS(O)₂CF₃ | Cl |
| Et | Cl | Cl | NHS(O)₂CF₃ | Cl |
| i-Pr | Cl | Cl | NHS(O)₂CF₃ | Cl |
| t-Bu | Cl | Cl | NHS(O)₂CF₃ | Cl |
| c-Pr | Cl | Cl | NHS(O)₂CF₃ | Cl |
| H | Cl | Cl | NHCOCF₃ | Cl |
| Me | Cl | Cl | NHCOCF₃ | Cl |
| Et | Cl | Cl | NHCOCF₃ | Cl |
| i-Pr | Cl | Cl | NHCOCF₃ | Cl |
| t-Bu | Cl | Cl | NHCOCF₃ | Cl |
| c-Pr | Cl | Cl | NHCOCF₃ | Cl |
| H | Cl | Cl | OCH₂CN | Cl |
| Me | Cl | Cl | OCH₂CN | Cl |
| Et | Cl | Cl | OCH₂CN | Cl |
| i-Pr | Cl | Cl | OCH₂CN | Cl |
| t-Bu | Cl | Cl | OCH₂CN | Cl |
| c-Pr | Cl | Cl | OCH₂CN | Cl |
| H | Cl | Cl | OCH₂NO₂ | Cl |
| Me | Cl | Cl | OCH₂NO₂ | Cl |
| Et | Cl | Cl | OCH₂NO₂ | Cl |
| i-Pr | Cl | Cl | OCH₂NO₂ | Cl |
| t-Bu | Cl | Cl | OCH₂NO₂ | Cl |
| c-Pr | Cl | Cl | OCH₂NO₂ | Cl |
| H | Cl | Cl | O-c-Pr | Cl |
| Me | Cl | Cl | O-c-Pr | Cl |
| Et | Cl | Cl | O-c-Pr | Cl |
| i-Pr | Cl | Cl | O-c-Pr | Cl |
| t-Bu | Cl | Cl | O-c-Pr | Cl |
| c-Pr | Cl | Cl | O-c-Pr | Cl |
| H | Cl | Cl | CH₂OCHF₂ | Cl |
| Me | Cl | Cl | CH₂OCHF₂ | Cl |
| Et | Cl | Cl | CH₂OCHF₂ | Cl |
| i-Pr | Cl | Cl | CH₂OCHF₂ | Cl |
| t-Bu | Cl | Cl | CH₂OCHF₂ | Cl |
| c-Pr | Cl | Cl | CH₂OCHF₂ | Cl |
| H | Cl | Cl | CH₂SCHF₂ | Cl |
| Me | Cl | Cl | CH₂SCHF₂ | Cl |
| Et | Cl | Cl | CH₂SCHF₂ | Cl |
| i-Pr | Cl | Cl | CH₂SCHF₂ | Cl |
| t-Bu | Cl | Cl | CH₂SCHF₂ | Cl |
| c-Pr | Cl | Cl | CH₂SCHF₂ | Cl |
| H | Cl | Cl | CH₂S(O)₂CHF₂ | Cl |
| Me | Cl | Cl | CH₂S(O)₂CHF₂ | Cl |
| Et | Cl | Cl | CH₂S(O)₂CHF₂ | Cl |
| i-Pr | Cl | Cl | CH₂S(O)₂CHF₂ | Cl |
| t-Bu | Cl | Cl | CH₂S(O)₂CHF₂ | Cl |
| c-Pr | Cl | Cl | CH₂S(O)₂CHF₂ | Cl |

TABLE 4

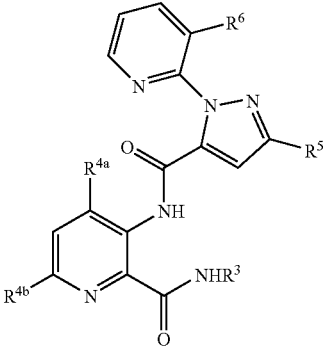

| R³ | R⁴ᵃ | R⁴ᵇ | R⁵ | R⁶ |
|---|---|---|---|---|
| H | Me | H | $CF_2OMe$ | Cl |
| Me | Me | H | $CF_2OMe$ | Cl |
| Et | Me | H | $CF_2OMe$ | Cl |
| i-Pr | Me | H | $CF_2OMe$ | Cl |
| t-Bu | Me | H | $CF_2OMe$ | Cl |
| c-Pr | Me | H | $CF_2OMe$ | Cl |
| H | Me | H | $CF_2OMe$ | F |
| Me | Me | H | $CF_2OMe$ | F |
| Et | Me | H | $CF_2OMe$ | F |
| i-Pr | Me | H | $CF_2OMe$ | F |
| t-Bu | Me | H | $CF_2OMe$ | F |
| c-Pr | Me | H | $CF_2OMe$ | F |
| H | Cl | H | $CF_2OMe$ | Cl |
| Me | Cl | H | $CF_2OMe$ | Cl |
| Et | Cl | H | $CF_2OMe$ | Cl |
| i-Pr | Cl | H | $CF_2OMe$ | Cl |
| t-Bu | Cl | H | $CF_2OMe$ | Cl |
| c-Pr | Cl | H | $CF_2OMe$ | Cl |
| H | Cl | H | $CF_2OMe$ | F |
| Me | Cl | H | $CF_2OMe$ | F |
| Et | Cl | H | $CF_2OMe$ | F |
| i-Pr | Cl | H | $CF_2OMe$ | F |
| t-Bu | Cl | H | $CF_2OMe$ | F |
| c-Pr | Cl | H | $CF_2OMe$ | F |
| H | Me | Cl | $CF_2OMe$ | Cl |
| Me | Me | Cl | $CF_2OMe$ | Cl |
| Et | Me | Cl | $CF_2OMe$ | Cl |
| i-Pr | Me | Cl | $CF_2OMe$ | Cl |
| t-Bu | Me | Cl | $CF_2OMe$ | Cl |
| c-Pr | Me | Cl | $CF_2OMe$ | Cl |
| H | Me | Cl | $CF_2OMe$ | F |
| Me | Me | Cl | $CF_2OMe$ | F |
| Et | Me | Cl | $CF_2OMe$ | F |
| i-Pr | Me | Cl | $CF_2OMe$ | F |
| t-Bu | Me | Cl | $CF_2OMe$ | F |
| c-Pr | Me | Cl | $CF_2OMe$ | F |
| Me | Me | Br | $CF_2OMe$ | Cl |
| Et | Me | Br | $CF_2OMe$ | Cl |
| i-Pr | Me | Br | $CF_2OMe$ | Cl |
| t-Bu | Me | Br | $CF_2OMe$ | Cl |
| c-Pr | Me | Br | $CF_2OMe$ | Cl |
| H | Me | Br | $CF_2OMe$ | F |
| Me | Me | Br | $CF_2OMe$ | F |
| Et | Me | Br | $CF_2OMe$ | F |
| i-Pr | Me | Br | $CF_2OMe$ | F |
| t-Bu | Me | Br | $CF_2OMe$ | F |
| c-Pr | Me | Br | $CF_2OMe$ | F |
| H | Cl | Cl | $CF_2OMe$ | Cl |
| Me | Cl | Cl | $CF_2OMe$ | Cl |
| Et | Cl | Cl | $CF_2OMe$ | Cl |
| i-Pr | Cl | Cl | $CF_2OMe$ | Cl |
| t-Bu | Cl | Cl | $CF_2OMe$ | Cl |
| c-Pr | Cl | Cl | $CF_2OMe$ | Cl |
| H | Cl | Cl | $CF_2OMe$ | F |
| Me | Cl | Cl | $CF_2OMe$ | F |
| Et | Cl | Cl | $CF_2OMe$ | F |
| i-Pr | Cl | Cl | $CF_2OMe$ | F |
| t-Bu | Cl | Cl | $CF_2OMe$ | F |
| c-Pr | Cl | Cl | $CF_2OMe$ | F |

TABLE 4-continued

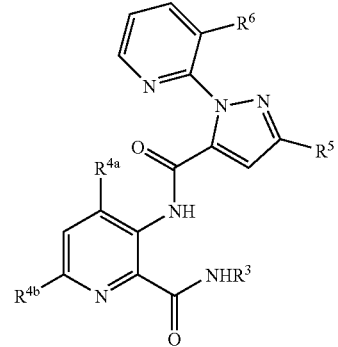

| R³ | R⁴ᵃ | R⁴ᵇ | R⁵ | R⁶ |
|---|---|---|---|---|
| H | Me | CN | $CF_2OMe$ | Cl |
| Me | Me | CN | $CF_2OMe$ | Cl |
| Et | Me | CN | $CF_2OMe$ | Cl |
| i-Pr | Me | CN | $CF_2OMe$ | Cl |
| t-Bu | Me | CN | $CF_2OMe$ | Cl |
| c-Pr | Me | CN | $CF_2OMe$ | Cl |
| H | Me | CN | $CF_2OMe$ | F |
| Me | Me | CN | $CF_2OMe$ | F |
| Et | Me | CN | $CF_2OMe$ | F |
| i-Pr | Me | CN | $CF_2OMe$ | F |
| t-Bu | Me | CN | $CF_2OMe$ | F |
| c-Pr | Me | CN | $CF_2OMe$ | F |
| H | Me | Cl | $CF_2OMe$ | $CF_3$ |
| Me | Me | Cl | $CF_2OMe$ | $CF_3$ |
| Et | Me | Cl | $CF_2OMe$ | $CF_3$ |
| i-Pr | Me | Cl | $CF_2OMe$ | $CF_3$ |
| t-Bu | Me | Cl | $CF_2OMe$ | $CF_3$ |
| c-Pr | Me | Cl | $CF_2OMe$ | $CF_3$ |
| H | Me | Cl | $CF_2OMe$ | CN |
| Me | Me | Cl | $CF_2OMe$ | CN |
| Et | Me | Cl | $CF_2OMe$ | CN |
| i-Pr | Me | Cl | $CF_2OMe$ | CN |
| t-Bu | Me | Cl | $CF_2OMe$ | CN |
| c-Pr | Me | Cl | $CF_2OMe$ | CN |
| H | Me | I | $CF_2OMe$ | Cl |
| Me | Me | I | $CF_2OMe$ | Cl |
| Et | Me | I | $CF_2OMe$ | Cl |
| i-Pr | Me | I | $CF_2OMe$ | Cl |
| t-Bu | Me | I | $CF_2OMe$ | Cl |
| c-Pr | Me | I | $CF_2OMe$ | Cl |
| H | Me | F | $CF_2OMe$ | Cl |
| Me | Me | F | $CF_2OMe$ | Cl |
| Et | Me | F | $CF_2OMe$ | Cl |
| i-Pr | Me | F | $CF_2OMe$ | Cl |
| t-Bu | Me | F | $CF_2OMe$ | Cl |
| c-Pr | Me | F | $CF_2OMe$ | Cl |
| H | Br | Cl | $CF_2OMe$ | Cl |
| Me | Br | Cl | $CF_2OMe$ | Cl |
| Et | Br | Cl | $CF_2OMe$ | Cl |
| i-Pr | Br | Cl | $CF_2OMe$ | Cl |
| t-Bu | Br | Cl | $CF_2OMe$ | Cl |
| c-Pr | Br | Cl | $CF_2OMe$ | Cl |
| H | Cl | Br | $CF_2OMe$ | Cl |
| Me | Cl | Br | $CF_2OMe$ | Cl |
| Et | Cl | Br | $CF_2OMe$ | Cl |
| i-Pr | Cl | Br | $CF_2OMe$ | Cl |
| t-Bu | Cl | Br | $CF_2OMe$ | Cl |
| c-Pr | Cl | Br | $CF_2OMe$ | Cl |
| H | Me | Cl | $CF_2SMe$ | Cl |
| Me | Me | Cl | $CF_2SMe$ | Cl |
| Et | Me | Cl | $CF_2SMe$ | Cl |
| i-Pr | Me | Cl | $CF_2SMe$ | Cl |
| t-Bu | Me | Cl | $CF_2SMe$ | Cl |
| c-Pr | Me | Cl | $CF_2SMe$ | Cl |
| H | Me | Cl | $CF_2S(O)Me$ | Cl |
| Me | Me | Cl | $CF_2S(O)Me$ | Cl |
| Et | Me | Cl | $CF_2S(O)Me$ | Cl |
| i-Pr | Me | Cl | $CF_2S(O)Me$ | Cl |
| t-Bu | Me | Cl | $CF_2S(O)Me$ | Cl |

TABLE 4-continued

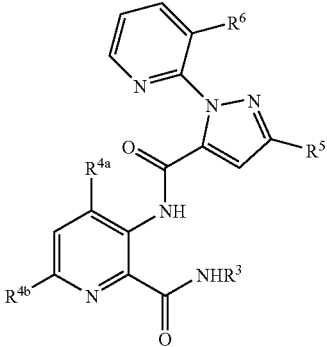

| $R^3$ | $R^{4a}$ | $R^{4b}$ | $R^5$ | $R^6$ |
|---|---|---|---|---|
| c-Pr | Me | Cl | CF$_2$S(O)Me | Cl |
| H | Me | Cl | CF$_2$S(O)$_2$Me | Cl |
| Me | Me | Cl | CF$_2$S(O)$_2$Me | Cl |
| Et | Me | Cl | CF$_2$S(O)$_2$Me | Cl |
| i-Pr | Me | Cl | CF$_2$S(O)$_2$Me | Cl |
| t-Bu | Me | Cl | CP2S(O)$_2$Me | Cl |
| c-Pr | Me | Cl | CF$_2$S(O)$_2$Me | Cl |
| H | Me | H | CH$_2$OMe | Cl |
| Me | Me | H | CH$_2$OMe | Cl |
| Et | Me | H | CH$_2$OMe | Cl |
| i-Pr | Me | H | CH$_2$OMe | Cl |
| t-Bu | Me | H | CH$_2$OMe | Cl |
| c-Pr | Me | H | CH$_2$OMe | Cl |
| H | Cl | H | CH$_2$OMe | Cl |
| Me | Cl | H | CH$_2$OMe | Cl |
| Et | Cl | H | CH$_2$OMe | Cl |
| i-Pr | Cl | H | CH$_2$OMe | Cl |
| t-Bu | Cl | H | CH$_2$OMe | Cl |
| c-Pr | Cl | H | CH$_2$OMe | Cl |
| H | Me | Cl | CH$_2$OMe | Cl |
| Me | Me | Cl | CH$_2$OMe | Cl |
| Et | Me | Cl | CH$_2$OMe | Cl |
| i-Pr | Me | Cl | CH$_2$OMe | Cl |
| t-Bu | Me | Cl | CH$_2$OMe | Cl |
| c-Pr | Me | Cl | CH$_2$OMe | Cl |
| H | Me | H | CH$_2$SMe | Cl |
| Me | Me | H | CH$_2$SMe | Cl |
| Et | Me | H | CH$_2$SMe | Cl |
| i-Pr | Me | H | CH$_2$SMe | Cl |
| t-Bu | Me | H | CH$_2$SMe | Cl |
| c-Pr | Me | H | CH$_2$SMe | Cl |
| H | Cl | H | CH$_2$SMe | Cl |
| Me | Cl | H | CH$_2$SMe | Cl |
| Et | Cl | H | CH$_2$SMe | Cl |
| i-Pr | Cl | H | CH$_2$SMe | Cl |
| t-Bu | Cl | H | CH$_2$SMe | Cl |
| c-Pr | Cl | H | CH$_2$SMe | Cl |
| H | Me | Cl | CH$_2$SMe | Cl |
| Me | Me | Cl | CH$_2$SMe | Cl |
| Et | Me | Cl | CH$_2$SMe | Cl |
| i-Pr | Me | Cl | CH$_2$SMe | Cl |
| t-Bu | Me | Cl | CH$_2$SMe | Cl |
| c-Pr | Me | Cl | CH$_2$SMe | Cl |
| H | Me | Cl | CH$_2$S(O)Me | Cl |
| Me | Me | Cl | CH$_2$S(O)Me | Cl |
| Et | Me | Cl | CH$_2$S(O)Me | Cl |
| i-Pr | Me | Cl | CH$_2$S(O)Me | Cl |
| t-Bu | Me | Cl | CH$_2$S(O)Me | Cl |
| c-Pr | Me | Cl | CH$_2$S(O)Me | Cl |
| H | Me | Cl | CH$_2$S(O)$_2$Me | Cl |
| Me | Me | Cl | CH$_2$S(O)$_2$Me | Cl |
| Et | Me | Cl | CH$_2$S(O)$_2$Me | Cl |
| i-Pr | Me | Cl | CH$_2$S(O)$_2$Me | Cl |
| t-Bu | Me | Cl | CH$_2$S(O)$_2$Me | Cl |
| c-Pr | Me | Cl | CH$_2$S(O)$_2$Me | Cl |
| H | Me | H | OS(O)$_2$Me | Cl |
| Me | Me | H | OS(O)$_2$Me | Cl |
| Et | Me | H | OS(O)$_2$Me | Cl |
| i-Pr | Me | H | OS(O)$_2$Me | Cl |

TABLE 4-continued

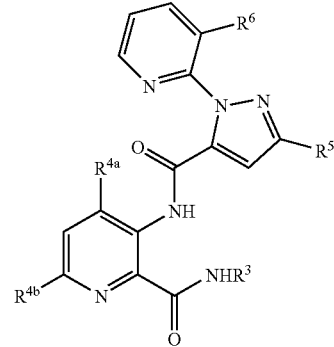

| $R^3$ | $R^{4a}$ | $R^{4b}$ | $R^5$ | $R^6$ |
|---|---|---|---|---|
| t-Bu | Me | H | OS(O)$_2$Me | Cl |
| c-Pr | Me | H | OS(O)$_2$Me | Cl |
| H | Cl | H | OS(O)$_2$Me | Cl |
| Me | Cl | H | OS(O)$_2$Me | Cl |
| Et | Cl | H | OS(O)$_2$Me | Cl |
| i-Pr | Cl | H | OS(O)$_2$Me | Cl |
| t-Bu | Cl | H | OS(O)$_2$Me | Cl |
| c-Pr | Cl | H | OS(O)$_2$Me | Cl |
| H | Me | Cl | OS(O)$_2$Me | Cl |
| Me | Me | Cl | OS(O)$_2$Me | Cl |
| Et | Me | Cl | OS(O)$_2$Me | Cl |
| i-Pr | Me | Cl | OS(O)$_2$Me | Cl |
| t-Bu | Me | Cl | OS(O)$_2$Me | Cl |
| c-Pr | Me | Cl | OS(O)$_2$Me | Cl |
| H | Me | H | OS(O)$_2$CF$_3$ | Cl |
| Me | Me | H | OS(O)$_2$CF$_3$ | Cl |
| Et | Me | H | OS(O)$_2$CF$_3$ | Cl |
| i-Pr | Me | H | OS(O)$_2$CF$_3$ | Cl |
| t-Bu | Me | H | OS(O)$_2$CF$_3$ | Cl |
| c-Pr | Me | H | OS(O)$_2$CF$_3$ | Cl |
| H | Cl | H | OS(O)$_2$CF$_3$ | Cl |
| Me | Cl | H | OS(O)$_2$CF$_3$ | Cl |
| Et | Cl | H | OS(O)$_2$CF$_3$ | Cl |
| i-Pr | Cl | H | OS(O)$_2$CF$_3$ | Cl |
| t-Bu | Cl | H | OS(O)$_2$CF$_3$ | Cl |
| c-Pr | Cl | H | OS(O)$_2$CF$_3$ | Cl |
| H | Me | Cl | OS(O)$_2$CClF$_2$ | Cl |
| Me | Me | Cl | OS(O)$_2$CClF$_2$ | Cl |
| Et | Me | Cl | OS(O)$_2$CClF$_2$ | Cl |
| i-Pr | Me | Cl | OS(O)$_2$CClF$_2$ | Cl |
| t-Bu | Me | Cl | OS(O)$_2$CClF$_2$ | Cl |
| c-Pr | Me | Cl | OS(O)$_2$CClF$_2$ | Cl |
| H | Me | Cl | OCH$_2$C≡CH | Cl |
| Me | Me | Cl | OCH$_2$C≡CH | Cl |
| Et | Me | Cl | OCH$_2$C≡CH | Cl |
| i-Pr | Me | Cl | OCH$_2$C≡CH | Cl |
| t-Bu | Me | Cl | OCH$_2$C≡CH | Cl |
| c-Pr | Me | Cl | OCH$_2$C≡CH | Cl |
| H | Me | Cl | OCH$_2$CH=CH$_2$ | Cl |
| Me | Me | Cl | OCH$_2$CH=CH$_2$ | Cl |
| Et | Me | Cl | OCH$_2$CH=CH$_2$ | Cl |
| i-Pr | Me | Cl | OCH$_2$CH=CH$_2$ | Cl |
| t-Bu | Me | Cl | OCH$_2$CH=CH$_2$ | Cl |
| c-Pr | Me | Cl | OCH$_2$CH=CH$_2$ | Cl |
| H | Me | Cl | NHCH$_2$CF$_3$ | Cl |
| Me | Me | Cl | NHCH$_2$CF$_3$ | Cl |
| Et | Me | Cl | NHCH$_2$CF$_3$ | Cl |
| i-Pr | Me | Cl | NHCH$_2$CF$_3$ | Cl |
| t-Bu | Me | Cl | NHCH$_2$CF$_3$ | Cl |
| c-Pr | Me | Cl | NHCH$_2$CF$_3$ | Cl |
| H | Me | Cl | OCH$_2$CCl=CH$_2$ | Cl |
| Me | Me | Cl | OCH$_2$CCl=CH$_2$ | Cl |
| Et | Me | Cl | OCH$_2$CCl=CH$_2$ | Cl |
| i-Pr | Me | Cl | OCH$_2$CCl=CH$_2$ | Cl |
| t-Bu | Me | Cl | OCH$_2$CCl=CH$_2$ | Cl |
| c-Pr | Me | Cl | OCH$_2$CCl=CH$_2$ | Cl |
| H | Me | Cl | OCH$_2$CH=CF$_2$ | Cl |
| Me | Me | Cl | OCH$_2$CH=CF$_2$ | Cl |
| Et | Me | Cl | OCH$_2$CH=CF$_2$ | Cl |

TABLE 4-continued

| R³ | R⁴ᵃ | R⁴ᵇ | R⁵ | R⁶ |
|---|---|---|---|---|
| i-Pr | Me | Cl | OCH₂CH=CF₂ | Cl |
| t-Bu | Me | Cl | OCH₂CH=CF₂ | Cl |
| c-Pr | Me | Cl | OCH₂CH=CF₂ | Cl |
| H | Me | Cl | NHS(O)₂CF₃ | Cl |
| Me | Me | Cl | NHS(O)₂CF₃ | Cl |
| Et | Me | Cl | NHS(O)₂CF₃ | Cl |
| i-Pr | Me | Cl | NHS(O)₂CF₃ | Cl |
| t-Bu | Me | Cl | NHS(O)₂CF₃ | Cl |
| c-Pr | Me | Cl | NHS(O)₂CF₃ | Cl |
| H | Me | Cl | NHCOCF₃ | Cl |
| Me | Me | Cl | NHCOCF₃ | Cl |
| Et | Me | Cl | NHCOCF₃ | Cl |
| i-Pr | Me | Cl | NHCOCF₃ | Cl |
| t-Bu | Me | Cl | NHCOCF₃ | Cl |
| c-Pr | Me | Cl | NHCOCF₃ | Cl |
| H | Me | Cl | OCH₂CN | Cl |
| Me | Me | Cl | OCH₂CN | Cl |
| Et | Me | Cl | OCH₂CN | Cl |
| i-Pr | Me | Cl | OCH₂CN | Cl |
| t-Bu | Me | Cl | OCH₂CN | Cl |
| c-Pr | Me | Cl | OCH₂CN | Cl |
| H | Me | Cl | OCH₂NO₂ | Cl |
| Me | Me | Cl | OCH₂NO₂ | Cl |
| Et | Me | Cl | OCH₂NO₂ | Cl |
| i-Pr | Me | Cl | OCH₂NO₂ | Cl |
| t-Bu | Me | Cl | OCH₂NO₂ | Cl |
| c-Pr | Me | Cl | OCH₂NO₂ | Cl |
| H | Me | Cl | O-c-Pr | Cl |
| Me | Me | Cl | O-c-Pr | Cl |
| Et | Me | Cl | O-c-Pr | Cl |
| i-Pr | Me | Cl | O-c-Pr | Cl |
| t-Bu | Me | Cl | O-c-Pr | Cl |
| c-Pr | Me | Cl | O-c-Pr | Cl |
| H | Me | Cl | CH₂OCHF₂ | Cl |
| Me | Me | Cl | CH₂OCHF₂ | Cl |
| Et | Me | Cl | CH₂OCHF₂ | Cl |
| E-Pr | Me | Cl | CH₂OCHF₂ | Cl |
| t-Bu | Me | Cl | CH₂OCHF₂ | Cl |
| c-Pr | Me | Cl | CH₂OCHF₂ | Cl |
| H | Me | Cl | CH₂SCHF₂ | Cl |
| Me | Me | Cl | CH₂SCHF₂ | Cl |
| Et | Me | Cl | CH₂SCHF₂ | Cl |
| i-Pr | Me | Cl | CH₂SCHF₂ | Cl |
| t-Bu | Me | Cl | CH₂SCHF₂ | Cl |
| c-Pr | Me | Cl | CH₂SCHF₂ | Cl |
| H | Me | Cl | CH₂S(O)₂CHF₂ | Cl |
| Me | Me | Cl | CH₂S(O)₂CHF₂ | Cl |
| Et | Me | Cl | CH₂S(O)₂CHF₂ | Cl |
| i-Pr | Me | Cl | CH₂S(O)₂CHF₂ | Cl |
| t-Bu | Me | Cl | CH₂S(O)₂CHF₂ | Cl |
| c-Pr | Me | Cl | CH₂S(O)₂CHF₂ | Cl |
| H | Me | H | CF₂OEt | Cl |
| Me | Me | H | CF₂OEt | Cl |
| Et | Me | H | CF₂OEt | Cl |
| i-Pr | Me | H | CF₂OEt | Cl |
| t-Bu | Me | H | CF₂OEt | Cl |
| c-Pr | Me | H | CF₂OEt | Cl |
| H | Me | H | CF₂OEt | F |
| Me | Me | H | CF₂OEt | F |

TABLE 4-continued

| R³ | R⁴ᵃ | R⁴ᵇ | R⁵ | R⁶ |
|---|---|---|---|---|
| Et | Me | H | CF₂OEt | F |
| i-Pr | Me | H | CF₂OEt | F |
| t-Bu | Me | H | CF₂OEt | F |
| c-Pr | Me | H | CF₂OEt | F |
| H | Cl | H | CF₂OEt | Cl |
| Me | Cl | H | CF₂OEt | Cl |
| Et | Cl | H | CF₂OEt | Cl |
| i-Pr | Cl | H | CF₂OEt | Cl |
| t-Bu | Cl | H | CF₂OEt | Cl |
| c-Pr | Cl | H | CF₂OEt | Cl |
| H | Cl | H | CF₂OEt | F |
| Me | Cl | H | CF₂OEt | F |
| Et | Cl | H | CF₂OEt | F |
| i-Pr | Cl | H | CF₂OEt | F |
| t-Bu | Cl | H | CF₂OEt | F |
| c-Pr | Cl | H | CF₂OEt | F |
| H | Me | Cl | CF₂OEt | Cl |
| Me | Me | Cl | CF₂OEt | Cl |
| Et | Me | Cl | CF₂OEt | Cl |
| i-Pr | Me | Cl | CF₂OEt | Cl |
| t-Bu | Me | Cl | CF₂OEt | Cl |
| c-Pr | Me | Cl | CF₂OEt | Cl |
| H | Me | Cl | CF₂OEt | F |
| Me | Me | Cl | CF₂OEt | F |
| Et | Me | Cl | CF₂OEt | F |
| i-Pr | Me | Cl | CF₂OEt | F |
| t-Bu | Me | Cl | CF₂OEt | F |
| c-Pr | Me | Cl | CF₂OEt | F |
| Me | Me | Br | CF₂OEt | Cl |
| Et | Me | Br | CF₂OEt | Cl |
| i-Pr | Me | Br | CF₂OEt | Cl |
| t-Bu | Me | Br | CF₂OEt | Cl |
| c-Pr | Me | Br | CF₂OEt | Cl |
| H | Me | Br | CF₂OEt | F |
| Me | Me | Br | CF₂OEt | F |
| Et | Me | Br | CF₂OEt | F |
| i-Pr | Me | Br | CF₂OEt | F |
| t-Bu | Me | Br | CF₂OEt | F |
| c-Pr | Me | Br | CF₂OEt | F |
| H | Cl | Cl | CF₂OEt | Cl |
| Me | Cl | Cl | CF₂OEt | Cl |
| Et | Cl | Cl | CF₂OEt | Cl |
| i-Pr | Cl | Cl | CF₂OEt | Cl |
| t-Bu | Cl | Cl | CF₂OEt | Cl |
| c-Pr | Cl | Cl | CF₂OEt | Cl |
| H | Cl | Cl | CF₂OEt | F |
| Me | Cl | Cl | CF₂OEt | F |
| Et | Cl | Cl | CF₂OEt | F |
| i-Pr | Cl | Cl | CF₂OEt | F |
| t-Bu | Cl | Cl | CF₂OEt | F |
| c-Pr | Cl | Cl | CF₂OEt | F |
| H | Me | CN | CF₂OEt | Cl |
| Me | Me | CN | CF₂OEt | Cl |
| Et | Me | CN | CF₂OEt | Cl |
| i-Pr | Me | CN | CF₂OEt | Cl |
| t-Bu | Me | CN | CF₂OEt | Cl |
| c-Pr | Me | CN | CF₂OEt | Cl |
| H | Me | CN | CF₂OEt | F |
| Me | Me | CN | CF₂OEt | F |

TABLE 4-continued

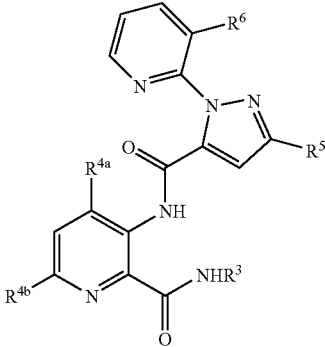

| $R^3$ | $R^{4a}$ | $R^{4b}$ | $R^5$ | $R^6$ |
|---|---|---|---|---|
| Et | Me | CN | $CF_2OEt$ | F |
| i-Pr | Me | CN | $CF_2OEt$ | F |
| t-Bu | Me | CN | $CF_2OEt$ | F |
| c-Pr | Me | CN | $CF_2OEt$ | F |
| H | Me | Cl | $CF_2OEt$ | $CF_3$ |
| Me | Me | Cl | $CF_2OEt$ | $CF_3$ |
| Et | Me | Cl | $CF_2OEt$ | $CF_3$ |
| i-Pr | Me | Cl | $CF_2OEt$ | $CF_3$ |
| t-Bu | Me | Cl | $CF_2OEt$ | $CF_3$ |
| c-Pr | Me | Cl | $CF_2OEt$ | $CF_3$ |
| H | Me | Cl | $CF_2OEt$ | CN |
| Me | Me | Cl | $CF_2OEt$ | CN |
| Et | Me | Cl | $CF_2OEt$ | CN |
| i-Pr | Me | Cl | $CF_2OEt$ | CN |
| t-Bu | Me | Cl | $CF_2OEt$ | CN |
| c-Pr | Me | Cl | $CF_2OEt$ | CN |
| H | Me | I | $CF_2OEt$ | Cl |
| Me | Me | I | $CF_2OEt$ | Cl |
| Et | Me | I | $CF_2OEt$ | Cl |
| i-Pr | Me | I | $CF_2OEt$ | Cl |
| t-Bu | Me | I | $CF_2OEt$ | Cl |
| c-Pr | Me | I | $CF_2OEt$ | Cl |
| H | Me | F | $CF_2OEt$ | Cl |
| Me | Me | F | $CF_2OEt$ | Cl |
| Et | Me | F | $CF_2OEt$ | Cl |
| i-Pr | Me | F | $CF_2OEt$ | Cl |
| t-Bu | Me | F | $CF_2OEt$ | Cl |
| c-Pr | Me | F | $CF_2OEt$ | Cl |
| H | Br | Cl | $CF_2OEt$ | Cl |
| Me | Br | Cl | $CF_2OEt$ | Cl |
| Et | Br | Cl | $CF_2OEt$ | Cl |
| i-Pr | Br | Cl | $CF_2OEt$ | Cl |
| t-Bu | Br | Cl | $CF_2OEt$ | Cl |
| c-Pr | Br | Cl | $CF_2OEt$ | Cl |
| H | Cl | Br | $CF_2OEt$ | Cl |
| Me | Cl | Br | $CF_2OEt$ | Cl |
| Et | Cl | Br | $CF_2OEt$ | Cl |
| i-Pr | Cl | Br | $CF_2OEt$ | Cl |
| t-Bu | Cl | Br | $CF_2OEt$ | Cl |
| c-Pr | Cl | Br | $CF_2OEt$ | Cl |
| H | Me | Cl | $CF_2SEt$ | Cl |
| Me | Me | Cl | $CF_2SEt$ | Cl |
| Et | Me | Cl | $CF_2SEt$ | Cl |
| i-Pr | Me | Cl | $CF_2SEt$ | Cl |
| t-Bu | Me | Cl | $CF_2SEt$ | Cl |
| c-Pr | Me | Cl | $CF_2SEt$ | Cl |
| H | Me | Cl | $CF_2S(O)Et$ | Cl |
| Me | Me | Cl | $CF_2S(O)Et$ | Cl |
| Et | Me | Cl | $CF_2S(O)Et$ | Cl |
| i-Pr | Me | Cl | $CF_2S(O)Et$ | Cl |
| t-Bu | Me | Cl | $CF_2S(O)Et$ | Cl |
| c-Pr | Me | Cl | $CF_2S(O)Et$ | Cl |
| H | Me | Cl | $CF_2S(O)_2Et$ | Cl |
| Me | Me | Cl | $CF_2S(O)_2Et$ | Cl |
| Et | Me | Cl | $CF_2S(O)_2Et$ | Cl |
| i-Pr | Me | Cl | $CF_2S(O)_2Et$ | Cl |
| t-Bu | Me | Cl | $CF_2S(O)_2Et$ | Cl |
| c-Pr | Me | Cl | $CF_2S(O)_2Et$ | Cl |
| H | Me | H | $CH_2OEt$ | Cl |

TABLE 4-continued

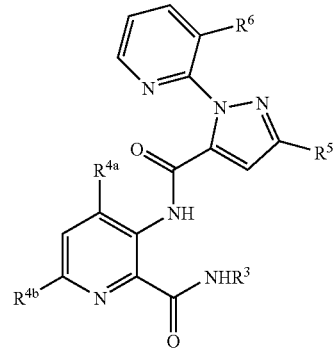

| $R^3$ | $R^{4a}$ | $R^{4b}$ | $R^5$ | $R^6$ |
|---|---|---|---|---|
| Me | Me | H | $CH_2OEt$ | Cl |
| Et | Me | H | $CH_2OEt$ | Cl |
| i-Pr | Me | H | $CH_2OEt$ | Cl |
| t-Bu | Me | H | $CH_2OEt$ | Cl |
| c-Pr | Me | H | $CH_2OEt$ | Cl |
| H | Cl | H | $CH_2OEt$ | Cl |
| Me | Cl | H | $CH_2OEt$ | Cl |
| Et | Cl | H | $CH_2OEt$ | Cl |
| i-Pr | Cl | H | $CH_2OEt$ | Cl |
| t-Bu | Cl | H | $CH_2OEt$ | Cl |
| c-Pr | Cl | H | $CH_2OEt$ | Cl |
| H | Me | Cl | $CH_2OEt$ | Cl |
| Me | Me | Cl | $CH_2OEt$ | Cl |
| Et | Me | Cl | $CH_2OEt$ | Cl |
| i-Pr | Me | Cl | $CH_2OEt$ | Cl |
| t-Bu | Me | Cl | $CH_2OEt$ | Cl |
| c-Pr | Me | Cl | $CH_2OEt$ | Cl |
| H | Me | H | $CH_2SEt$ | Cl |
| Me | Me | H | $CH_2SEt$ | Cl |
| Et | Me | H | $CH_2SEt$ | Cl |
| i-Pr | Me | H | $CH_2SEt$ | Cl |
| t-Bu | Me | H | $CH_2SEt$ | Cl |
| c-Pr | Me | H | $CH_2SEt$ | Cl |
| H | Cl | H | $CH_2SEt$ | Cl |
| Me | Cl | H | $CH_2SEt$ | Cl |
| Et | Cl | H | $CH_2SEt$ | Cl |
| i-Pr | Cl | H | $CH_2SEt$ | Cl |
| t-Bu | Cl | H | $CH_2SEt$ | Cl |
| c-Pr | Cl | H | $CH_2SEt$ | Cl |
| H | Me | Cl | $CH_2SEt$ | Cl |
| Me | Me | Cl | $CH_2SEt$ | Cl |
| Et | Me | Cl | $CH_2SEt$ | Cl |
| i-Pr | Me | Cl | $CH_2SEt$ | Cl |
| t-Bu | Me | Cl | $CH_2SEt$ | Cl |
| c-Pr | Me | Cl | $CH_2SEt$ | Cl |
| H | Me | Cl | $CH_2S(O)Et$ | Cl |
| Me | Me | Cl | $CH_2S(O)Et$ | Cl |
| Et | Me | Cl | $CH_2S(O)Et$ | Cl |
| i-Pr | Me | Cl | $CH_2S(O)Et$ | Cl |
| t-Bu | Me | Cl | $CH_2S(O)Et$ | Cl |
| c-Pr | Me | Cl | $CH_2S(O)Et$ | Cl |
| H | Me | Cl | $CH_2S(O)_2Et$ | Cl |
| Me | Me | Cl | $CH_2S(O)_2Et$ | Cl |
| Et | Me | Cl | $CH_2S(O)_2Et$ | Cl |
| i-Pr | Me | Cl | $CH_2S(O)_2Et$ | Cl |
| t-Bu | Me | Cl | $CH_2S(O)_2Et$ | Cl |
| c-Pr | Me | Cl | $CH_2S(O)_2Et$ | Cl |
| H | Me | H | $OS(O)_2Et$ | Cl |
| Me | Me | H | $OS(O)_2Et$ | Cl |
| Et | Me | H | $OS(O)_2Et$ | Cl |
| i-Pr | Me | H | $OS(O)_2Et$ | Cl |
| t-Bu | Me | H | $OS(O)_2Et$ | Cl |
| c-Pr | Me | H | $OS(O)_2Et$ | Cl |
| H | Cl | H | $OS(O)_2Et$ | Cl |
| Me | Cl | H | $OS(O)_2Et$ | Cl |
| Et | Cl | H | $OS(O)_2Et$ | Cl |
| i-Pr | Cl | H | $OS(O)_2Et$ | Cl |
| t-Bu | Cl | H | $OS(O)_2Et$ | Cl |
| c-Pr | Cl | H | $OS(O)_2Et$ | Cl |

TABLE 4-continued

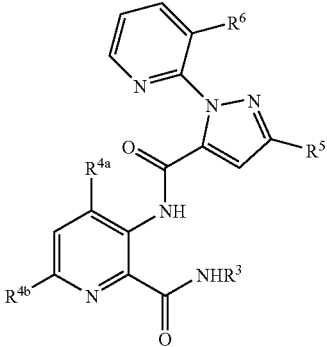

| R³ | R⁴ᵃ | R⁴ᵇ | R⁵ | R⁶ |
|---|---|---|---|---|
| H | Me | Cl | OS(O)₂Et | Cl |
| Me | Me | Cl | OS(O)₂Et | Cl |
| Et | Me | Cl | OS(O)₂Et | Cl |
| i-Pr | Me | Cl | OS(O)₂Et | Cl |
| t-Bu | Me | Cl | OS(O)₂Et | Cl |
| c-Pr | Me | Cl | OS(O)₂Et | Cl |
| H | Me | Cl | OS(O)₂CF₃ | Cl |
| Me | Me | Cl | OS(O)₂CF₃ | Cl |
| Et | Me | Cl | OS(O)₂CF₃ | Cl |
| i-Pr | Me | Cl | OS(O)₂CF₃ | Cl |
| t-Bu | Me | Cl | OS(O)₂CF₃ | Cl |
| c-Pr | Me | Cl | OS(O)₂CF₃ | Cl |
| H | Cl | Cl | OS(O)₂CF₃ | Cl |
| Me | Cl | Cl | OS(O)₂CF₃ | Cl |
| Et | Cl | Cl | OS(O)₂CF₃ | Cl |
| i-Pr | Cl | Cl | OS(O)₂CF₃ | Cl |
| t-Bu | Cl | Cl | OS(O)₂CF₃ | Cl |
| c-Pr | Cl | Cl | OS(O)₂CF₃ | Cl |
| H | Me | Cl | OCOCF₃ | Cl |
| Me | Me | Cl | OCOCF₃ | Cl |
| Et | Me | Cl | OCOCF₃ | Cl |
| i-Pr | Me | Cl | OCOCF₃ | Cl |
| t-Bu | Me | Cl | OCOCF₃ | Cl |
| c-Pr | Me | Cl | OCOCF₃ | Cl |
| H | Cl | Cl | OCH₂C≡CH | Cl |
| Me | Cl | Cl | OCH₂C≡CH | Cl |
| Et | Cl | Cl | OCH₂C≡CH | Cl |
| i-Pr | Cl | Cl | OCH₂C≡CH | Cl |
| t-Bu | Cl | Cl | OCH₂C≡CH | Cl |
| c-Pr | Cl | Cl | OCH₂C≡CH | Cl |
| H | Cl | Cl | OCH₂CH=CH₂ | Cl |
| Me | Cl | Cl | OCH₂CH=CH₂ | Cl |
| Et | Cl | Cl | OCH₂CH=CH₂ | Cl |
| i-Pr | Cl | Cl | OCH₂CH=CH₂ | Cl |
| t-Bu | Cl | Cl | OCH₂CH=CH₂ | Cl |
| c-Pr | Cl | Cl | OCH₂CH=CH₂ | Cl |
| H | Me | Cl | OCH₂-c-Pr | Cl |
| Me | Me | Cl | OCH₂-c-Pr | Cl |
| Et | Me | Cl | OCH₂-c-Pr | Cl |
| i-Pr | Me | Cl | OCH₂-c-Pr | Cl |
| t-Bu | Me | Cl | OCH₂-c-Pr | Cl |
| c-Pr | Me | Cl | OCH₂-c-Pr | Cl |
| H | Cl | Cl | OCH₂CCl=CH₂ | Cl |
| Me | Cl | Cl | OCH₂CCl=CH₂ | Cl |
| Et | Cl | Cl | OCH₂CCl=CH₂ | Cl |
| i-Pr | Cl | Cl | OCH₂CCl=CH₂ | Cl |
| t-Bu | Cl | Cl | OCH₂CCl=CH₂ | Cl |
| c-Pr | Cl | Cl | OCH₂CCl=CH₂ | Cl |
| H | Cl | Cl | OCH₂CH=CF₂ | Cl |
| Me | Cl | Cl | OCH₂CH=CF₂ | Cl |
| Et | Cl | Cl | OCH₂CH=CF₂ | Cl |
| i-Pr | Cl | Cl | OCH₂CH=CF₂ | Cl |
| t-Bu | Cl | Cl | OCH₂CH=CF₂ | Cl |
| c-Pr | Cl | Cl | OCH₂CH=CF₂ | Cl |
| H | Cl | Cl | NHS(O)₂CF₃ | Cl |
| Me | Cl | Cl | NHS(O)₂CF₃ | Cl |

TABLE 4-continued

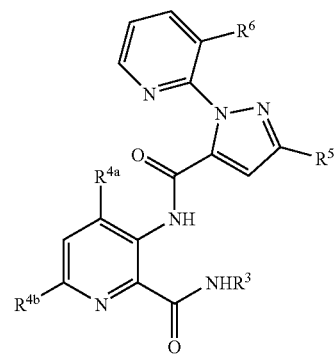

| R³ | R⁴ᵃ | R⁴ᵇ | R⁵ | R⁶ |
|---|---|---|---|---|
| Et | Cl | Cl | NHS(O)₂CF₃ | Cl |
| i-Pr | Cl | Cl | NHS(O)₂CF₃ | Cl |
| t-Bu | Cl | Cl | NHS(O)₂CF₃ | Cl |
| c-Pr | Cl | Cl | NHS(O)₂CF₃ | Cl |
| H | Cl | Cl | NHCOCF₃ | Cl |
| Me | Cl | Cl | NHCOCF₃ | Cl |
| Et | Cl | Cl | NHCOCF₃ | Cl |
| i-Pr | Cl | Cl | NHCOCF₃ | Cl |
| t-Bu | Cl | Cl | NHCOCF₃ | Cl |
| c-Pr | Cl | Cl | NHCOCF₃ | Cl |
| H | Cl | Cl | OCH₂CN | Cl |
| Me | Cl | Cl | OCH₂CN | Cl |
| Et | Cl | Cl | OCH₂CN | Cl |
| i-Pr | Cl | Cl | OCH₂CN | Cl |
| t-Bu | Cl | Cl | OCH₂CN | Cl |
| c-Pr | Cl | Cl | OCH₂CN | Cl |
| H | Cl | Cl | OCH₂NO₂ | Cl |
| Me | Cl | Cl | OCH₂NO₂ | Cl |
| Et | Cl | Cl | OCH₂NO₂ | Cl |
| i-Pr | Cl | Cl | OCH₂NO₂ | Cl |
| t-Bu | Cl | Cl | OCH₂NO₂ | Cl |
| c-Pr | Cl | Cl | OCH₂NO₂ | Cl |
| H | Cl | Cl | O-c-Pr | Cl |
| Me | Cl | Cl | O-c-Pr | Cl |
| Et | Cl | Cl | O-c-Pr | Cl |
| i-Pr | Cl | Cl | O-c-Pr | Cl |
| t-Bu | Cl | Cl | O-c-Pr | Cl |
| c-Pr | Cl | Cl | O-c-Pr | Cl |
| H | Cl | Cl | CH₂OCHF₂ | Cl |
| Me | Cl | Cl | CH₂OCHF₂ | Cl |
| Et | Cl | Cl | CH₂OCHF₂ | Cl |
| i-Pr | Cl | Cl | CH₂OCHF₂ | Cl |
| t-Bu | Cl | Cl | CH₂OCHF₂ | Cl |
| c-Pr | Cl | Cl | CH₂OCHF₂ | Cl |
| H | Cl | Cl | CH₂SCHF₂ | Cl |
| Me | Cl | Cl | CH₂SCHF₂ | Cl |
| Et | Cl | Cl | CH₂SCHF₂ | Cl |
| i-Pr | Cl | Cl | CH₂SCHF₂ | Cl |
| t-Bu | Cl | Cl | CH₂SCHF₂ | Cl |
| c-Pr | Cl | Cl | CH₂SCHF₂ | Cl |
| H | Cl | Cl | CH₂S(O)₂CHF₂ | Cl |
| Me | Cl | Cl | CH₂S(O)₂CHF₂ | Cl |
| Et | Cl | Cl | CH₂S(O)₂CHF₂ | Cl |
| i-Pr | Cl | Cl | CH₂S(O)₂CHF₂ | Cl |
| t-Bu | Cl | Cl | CH₂S(O)₂CHF₂ | Cl |
| c-Pr | Cl | Cl | CH₂S(O)₂CHF₂ | Cl |

TABLE 5

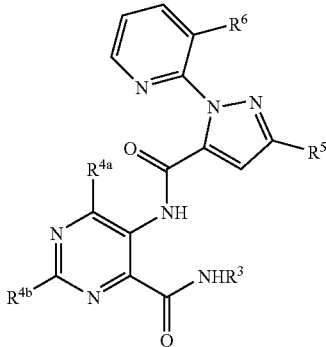

| R³ | R⁴ᵃ | R⁴ᵇ | R⁵ | R⁶ |
|---|---|---|---|---|
| H | Me | H | CF₂OMe | Cl |
| Me | Me | H | CF₂OMe | Cl |
| Et | Me | H | CF₂OMe | Cl |
| i-Pr | Me | H | CF₂OMe | Cl |
| t-Bu | Me | H | CF₂OMe | Cl |
| c-Pr | Me | H | CF₂OMe | Cl |
| H | Me | H | CF₂OMe | F |
| Me | Me | H | CF₂OMe | F |
| Et | Me | H | CF₂OMe | F |
| i-Pr | Me | H | CF₂OMe | F |
| t-Bu | Me | H | CF₂OMe | F |
| c-Pr | Me | H | CF₂OMe | F |
| H | Cl | H | CF₂OMe | Cl |
| Me | Cl | H | CF₂OMe | Cl |
| Et | Cl | H | CF₂OMe | Cl |
| i-Pr | Cl | H | CF₂OMe | Cl |
| t-Bu | Cl | H | CF₂OMe | Cl |
| c-Pr | Cl | H | CF₂OMe | Cl |
| H | Cl | H | CF₂OMe | F |
| Me | Cl | H | CF₂OMe | F |
| Et | Cl | H | CF₂OMe | F |
| i-Pr | Cl | H | CF₂OMe | F |
| t-Bu | Cl | H | CF₂OMe | F |
| c-Pr | Cl | H | CF₂OMe | F |
| H | Me | Cl | CF₂OMe | Cl |
| Me | Me | Cl | CF₂OMe | Cl |
| Et | Me | Cl | CF₂OMe | Cl |
| i-Pr | Me | Cl | CF₂OMe | Cl |
| t-Bu | Me | Cl | CF₂OMe | Cl |
| c-Pr | Me | Cl | CF₂OMe | Cl |
| H | Me | Cl | CF₂OMe | F |
| Me | Me | Cl | CF₂OMe | F |
| Et | Me | Cl | CF₂OMe | F |
| i-Pr | Me | Cl | CF₂OMe | F |
| t-Bu | Me | Cl | CF₂OMe | F |
| c-Pr | Me | Cl | CF₂OMe | F |
| Me | Me | Br | CF₂OMe | Cl |
| Et | Me | Br | CF₂OMe | Cl |
| i-Pr | Me | Br | CF₂OMe | Cl |
| t-Bu | Me | Br | CF₂OMe | Cl |
| c-Pr | Me | Br | CF₂OMe | Cl |
| H | Me | Br | CF₂OMe | F |
| Me | Me | Br | CF₂OMe | F |
| Et | Me | Br | CF₂OMe | F |
| i-Pr | Me | Br | CF₂OMe | F |
| t-Bu | Me | Br | CF₂OMe | F |
| c-Pr | Me | Br | CF₂OMe | F |
| H | Cl | Cl | CF₂OMe | Cl |
| Me | Cl | Cl | CF₂OMe | Cl |
| Et | Cl | Cl | CF₂OMe | Cl |
| i-Pr | Cl | Cl | CF₂OMe | Cl |
| t-Bu | Cl | Cl | CF₂OMe | Cl |
| c-Pr | Cl | Cl | CF₂OMe | Cl |
| H | Cl | Cl | CF₂OMe | F |
| Me | Cl | Cl | CF₂OMe | F |
| Et | Cl | Cl | CF₂OMe | F |
| i-Pr | Cl | Cl | CF₂OMe | F |
| t-Bu | Cl | Cl | CF₂OMe | F |
| c-Pr | Cl | Cl | CF₂OMe | F |

TABLE 5-continued

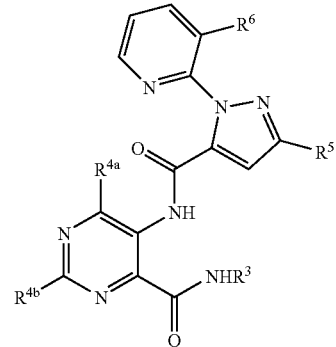

| R³ | R⁴ᵃ | R⁴ᵇ | R⁵ | R⁶ |
|---|---|---|---|---|
| H | Me | CN | CF₂OMe | Cl |
| Me | Me | CN | CF₂OMe | Cl |
| Et | Me | CN | CF₂OMe | Cl |
| i-Pr | Me | CN | CF₂OMe | Cl |
| t-Bu | Me | CN | CF₂OMe | Cl |
| c-Pr | Me | CN | CF₂OMe | Cl |
| H | Me | CN | CF₂OMe | F |
| Me | Me | CN | CF₂OMe | F |
| Et | Me | CN | CF₂OMe | F |
| i-Pr | Me | CN | CF₂OMe | F |
| t-Bu | Me | CN | CF₂OMe | F |
| c-Pr | Me | CN | CF₂OMe | F |
| H | Me | Cl | CF₂OMe | CF₃ |
| Me | Me | Cl | CF₂OMe | CF₃ |
| Et | Me | Cl | CF₂OMe | CF₃ |
| i-Pr | Me | Cl | CF₂OMe | CF₃ |
| t-Bu | Me | Cl | CF₂OMe | CF₃ |
| c-Pr | Me | Cl | CF₂OMe | CF₃ |
| H | Me | Cl | CF₂OMe | CN |
| Me | Me | Cl | CF₂OMe | CN |
| Et | Me | Cl | CF₂OMe | CN |
| i-Pr | Me | Cl | CF₂OMe | CN |
| t-Bu | Me | Cl | CF₂OMe | CN |
| c-Pr | Me | Cl | CF₂OMe | CN |
| H | Me | I | CF₂OMe | Cl |
| Me | Me | I | CF₂OMe | Cl |
| Et | Me | I | CF₂OMe | Cl |
| i-Pr | Me | I | CF₂OMe | Cl |
| t-Bu | Me | I | CF₂OMe | Cl |
| c-Pr | Me | I | CF₂OMe | Cl |
| H | Me | F | CF₂OMe | Cl |
| Me | Me | F | CF₂OMe | Cl |
| Et | Me | F | CF₂OMe | Cl |
| i-Pr | Me | F | CF₂OMe | Cl |
| t-Bu | Me | F | CF₂OMe | Cl |
| c-Pr | Me | F | CF₂OMe | Cl |
| H | Br | Cl | CF₂OMe | Cl |
| Me | Br | Cl | CF₂OMe | Cl |
| Et | Br | Cl | CF₂OMe | Cl |
| i-Pr | Br | Cl | CF₂OMe | Cl |
| t-Bu | Br | Cl | CF₂OMe | Cl |
| c-Pr | Br | Cl | CF₂OMe | Cl |
| H | Cl | Br | CF₂OMe | Cl |
| Me | Cl | Br | CF₂OMe | Cl |
| Et | Cl | Br | CF₂OMe | Cl |
| i-Pr | Cl | Br | CF₂OMe | Cl |
| t-Bu | Cl | Br | CF₂OMe | Cl |
| c-Pr | Cl | Br | CF₂OMe | Cl |
| H | Me | Cl | CF₂SMe | Cl |
| Me | Me | Cl | CF₂SMe | Cl |
| Et | Me | Cl | CF₂SMe | Cl |
| i-Pr | Me | Cl | CF₂SMe | Cl |
| t-Bu | Me | Cl | CF₂SMe | Cl |
| c-Pr | Me | Cl | CF₂SMe | Cl |
| H | Me | Cl | CF₂S(O)Me | Cl |
| Me | Me | Cl | CF₂S(O)Me | Cl |
| Et | Me | Cl | CF₂S(O)Me | Cl |
| i-Pr | Me | Cl | CF₂S(O)Me | Cl |
| t-Bu | Me | Cl | CF₂S(O)Me | Cl |

TABLE 5-continued

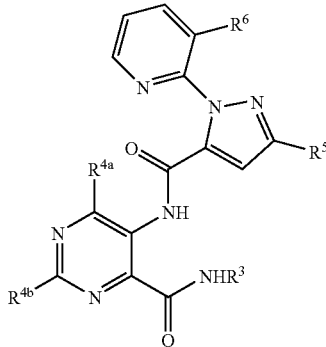

| R³ | R⁴ᵃ | R⁴ᵇ | R⁵ | R⁶ |
|---|---|---|---|---|
| c-Pr | Me | Cl | CF₂S(O)Me | Cl |
| H | Me | Cl | CF₂S(O)₂Me | Cl |
| Me | Me | Cl | CF₂S(O)₂Me | Cl |
| Et | Me | Cl | CF₂S(O)₂Me | Cl |
| i-Pr | Me | Cl | CF₂S(O)₂Me | Cl |
| t-Bu | Me | Cl | CF₂S(O)₂Me | Cl |
| c-Pr | Me | Cl | CF₂S(O)₂Me | Cl |
| H | Me | H | CH₂OMe | Cl |
| Me | Me | H | CH₂OMe | Cl |
| Et | Me | H | CH₂OMe | Cl |
| i-Pr | Me | H | CH₂OMe | Cl |
| t-Bu | Me | H | CH₂OMe | Cl |
| c-Pr | Me | H | CH₂OMe | Cl |
| H | Cl | H | CH₂OMe | Cl |
| Me | Cl | H | CH₂OMe | Cl |
| Et | Cl | H | CH₂OMe | Cl |
| i-Pr | Cl | H | CH₂OMe | Cl |
| t-Bu | Cl | H | CH₂OMe | Cl |
| c-Pr | Cl | H | CH₂OMe | Cl |
| H | Me | Cl | CH₂OMe | Cl |
| Me | Me | Cl | CH₂OMe | Cl |
| Et | Me | Cl | CH₂OMe | Cl |
| i-Pr | Me | Cl | CH₂OMe | Cl |
| t-Bu | Me | Cl | CH₂OMe | Cl |
| c-Pr | Me | Cl | CH₂OMe | Cl |
| H | Me | H | CH₂SMe | Cl |
| Me | Me | H | CH₂SMe | Cl |
| Et | Me | H | CH₂SMe | Cl |
| i-Pr | Me | H | CH₂SMe | Cl |
| t-Bu | Me | H | CH₂SMe | Cl |
| c-Pr | Me | H | CH₂SMe | Cl |
| H | Cl | H | CH₂SMe | Cl |
| Me | Cl | H | CH₂SMe | Cl |
| Et | Cl | H | CH₂SMe | Cl |
| i-Pr | Cl | H | CH₂SMe | Cl |
| t-Bu | Cl | H | CH₂SMe | Cl |
| c-Pr | Cl | H | CH₂SMe | Cl |
| H | Me | Cl | CH₂SMe | Cl |
| Me | Me | Cl | CH₂SMe | Cl |
| Et | Me | Cl | CH₂SMe | Cl |
| i-Pr | Me | Cl | CH₂SMe | Cl |
| t-Bu | Me | Cl | CH₂SMe | Cl |
| c-Pr | Me | Cl | CH₂SMe | Cl |
| H | Me | Cl | CH₂S(O)Me | Cl |
| Me | Me | Cl | CH₂S(O)Me | Cl |
| Et | Me | Cl | CH₂S(O)Me | Cl |
| i-Pr | Me | Cl | CH₂S(O)Me | Cl |
| t-Bu | Me | Cl | CH₂S(O)Me | Cl |
| c-Pr | Me | Cl | CH₂S(O)Me | Cl |
| H | Me | Cl | CH₂S(O)₂Me | Cl |
| Me | Me | Cl | CH₂S(O)₂Me | Cl |
| Et | Me | Cl | CH₂S(O)₂Me | Cl |
| i-Pr | Me | Cl | CH₂S(O)₂Me | Cl |
| t-Bu | Me | Cl | CH₂S(O)₂Me | Cl |
| c-Pr | Me | Cl | CH₂S(O)₂Me | Cl |
| H | Me | H | OS(O)₂Me | Cl |
| Me | Me | H | OS(O)₂Me | Cl |
| Et | Me | H | OS(O)₂Me | Cl |
| i-Pr | Me | H | OS(O)₂Me | Cl |

TABLE 5-continued

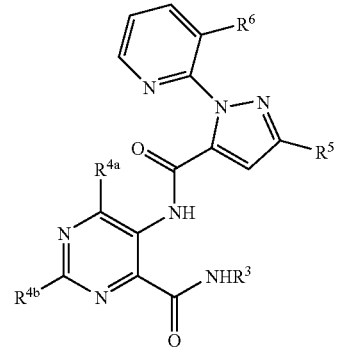

| R³ | R⁴ᵃ | R⁴ᵇ | R⁵ | R⁶ |
|---|---|---|---|---|
| t-Bu | Me | H | OS(O)₂Me | Cl |
| c-Pr | Me | H | OS(O)₂Me | Cl |
| H | Cl | H | OS(O)₂Me | Cl |
| Me | Cl | H | OS(O)₂Me | Cl |
| Et | Cl | H | OS(O)₂Me | Cl |
| i-Pr | Cl | H | OS(O)₂Me | Cl |
| t-Bu | Cl | H | OS(O)₂Me | Cl |
| c-Pr | Cl | H | OS(O)₂Me | Cl |
| H | Me | Cl | OS(O)₂Me | Cl |
| Me | Me | Cl | OS(O)₂Me | Cl |
| Et | Me | Cl | OS(O)₂Me | Cl |
| i-Pr | Me | Cl | OS(O)₂Me | Cl |
| t-Bu | Me | Cl | OS(O)₂Me | Cl |
| c-Pr | Me | Cl | OS(O)₂Me | Cl |
| H | Me | H | OS(O)₂CF₃ | Cl |
| Me | Me | H | OS(O)₂CF₃ | Cl |
| Et | Me | H | OS(O)₂CF₃ | Cl |
| i-Pr | Me | H | OS(O)₂CF₃ | Cl |
| t-iBu | Me | H | OS(O)₂CF₃ | Cl |
| c-Pr | Me | H | OS(O)₂CF₃ | Cl |
| H | Cl | H | OS(O)₂CF₃ | Cl |
| Me | Cl | H | OS(O)₂CF₃ | Cl |
| Et | Cl | H | OS(O)₂CF₃ | Cl |
| i-Pr | Cl | H | OS(O)₂CF₃ | Cl |
| t-Bu | Cl | H | OS(O)₂CF₃ | Cl |
| c-Pr | Cl | H | OS(O)₂CF₃ | Cl |
| H | Me | Cl | OS(O)₂CClF₂ | Cl |
| Me | Me | Cl | OS(O)₂CClF₂ | Cl |
| Et | Me | Cl | OS(O)₂CClF₂ | Cl |
| i-Pr | Me | Cl | OS(O)₂CClF₂ | Cl |
| t-Bu | Me | Cl | OS(O)₂CClF₂ | Cl |
| c-Pr | Me | Cl | OS(O)₂CClF₂ | Cl |
| H | Me | Cl | OCH₂C≡CH | Cl |
| Me | Me | Cl | OCH₂C≡CH | Cl |
| Et | Me | Cl | OCH₂C≡CH | Cl |
| i-Pr | Me | Cl | OCH₂C≡CH | Cl |
| t-Bu | Me | Cl | OCH₂C≡CH | Cl |
| c-Pr | Me | Cl | OCH₂C≡CH | Cl |
| H | Me | Cl | OCH₂CH=CH₂ | Cl |
| Me | Me | Cl | OCH₂CH=CH₂ | Cl |
| Et | Me | Cl | OCH₂CH=CH₂ | Cl |
| i-Pr | Me | Cl | OCH₂CH=CH₂ | Cl |
| t-Bu | Me | Cl | OCH₂CH=CH₂ | Cl |
| c-Pr | Me | Cl | OCH₂CH=CH₂ | Cl |
| H | Me | Cl | NHCH₂CF₃ | Cl |
| Me | Me | Cl | NHCH₂CF₃ | Cl |
| Et | Me | Cl | NHCH₂CF₃ | Cl |
| i-Pr | Me | Cl | NHCH₂CF₃ | Cl |
| t-Bu | Me | Cl | NHCH₂CF₃ | Cl |
| c-Pr | Me | Cl | NHCH₂CF₃ | Cl |
| H | Me | Cl | OCH₂CCl=CH₂ | Cl |
| Me | Me | Cl | OCH₂CCl=CH₂ | Cl |
| Et | Me | Cl | OCH₂CCl=CH₂ | Cl |
| i-Pr | Me | Cl | OCH₂CCl=CH₂ | Cl |
| t-Bu | Me | Cl | OCH₂CCl=CH₂ | Cl |
| c-Pr | Me | Cl | OCH₂CCl=CH₂ | Cl |
| H | Me | Cl | OCH₂CH=CF₂ | Cl |
| Me | Me | Cl | OCH₂CH=CF₂ | Cl |
| Et | Me | Cl | OCH₂CH=CF₂ | Cl |

TABLE 5-continued

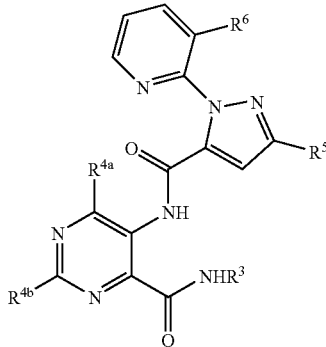

| R³ | R⁴ᵃ | R⁴ᵇ | R⁵ | R⁶ |
|---|---|---|---|---|
| i-Pr | Me | Cl | OCH₂CH=CH₂ | Cl |
| t-Bu | Me | Cl | OCH₂CH=CF₂ | Cl |
| c-Pr | Me | Cl | OCH₂CH=CF₂ | Cl |
| H | Me | Cl | NHS(O)₂CF₃ | Cl |
| Me | Me | Cl | NHS(O)₂CF₃ | Cl |
| Et | Me | Cl | NHS(O)₂CF₃ | Cl |
| i-Pr | Me | Cl | NHS(O)₂CF₃ | Cl |
| t-Bu | Me | Cl | NHS(O)₂CF₃ | Cl |
| c-Pr | Me | Cl | NHS(O)₂CF₃ | Cl |
| H | Me | Cl | NHCOCF₃ | Cl |
| Me | Me | Cl | NHCOCF₃ | Cl |
| Et | Me | Cl | NHCOCF₃ | Cl |
| i-Pr | Me | Cl | NHCOCF₃ | Cl |
| t-Bu | Me | Cl | NHCOCF₃ | Cl |
| c-Pr | Me | Cl | NHCOCF₃ | Cl |
| H | Me | Cl | OCH₂CN | Cl |
| Me | Me | Cl | OCH₂CN | Cl |
| Et | Me | Cl | OCH₂CN | Cl |
| i-Pr | Me | Cl | OCH₂CN | Cl |
| t-Bu | Me | Cl | OCH₂CN | Cl |
| c-Pr | Me | Cl | OCH₂CN | Cl |
| H | Me | Cl | OCH₂NO₂ | Cl |
| Me | Me | Cl | OCH₂NO₂ | Cl |
| Et | Me | Cl | OCH₂NO₂ | Cl |
| i-Pr | Me | Cl | OCH₂NO₂ | Cl |
| t-Bu | Me | Cl | OCH₂NO₂ | Cl |
| c-Pr | Me | Cl | OCH₂NO₂ | Cl |
| H | Me | Cl | O-c-Pr | Cl |
| Me | Me | Cl | O-c-Pr | Cl |
| Et | Me | Cl | O-c-Pr | Cl |
| i-Pr | Me | Cl | O-c-Pr | Cl |
| t-Bu | Me | Cl | O-c-Pr | Cl |
| c-Pr | Me | Cl | O-c-Pr | Cl |
| H | Me | Cl | CH₂OCHF₂ | Cl |
| Me | Me | Cl | CH₂OCHF₂ | Cl |
| Et | Me | Cl | CH₂OCHF₂ | Cl |
| i-Pr | Me | Cl | CH₂OCHF₂ | Cl |
| t-Bu | Me | Cl | CH₂OCHF₂ | Cl |
| c-Pr | Me | Cl | CH₂OCHF₂ | Cl |
| H | Me | Cl | CH₂SCHF₂ | Cl |
| Me | Me | Cl | CH₂SCHF₂ | Cl |
| Et | Me | Cl | CH₂SCHF₂ | Cl |
| i-Pr | Me | Cl | CH₂SCHF₂ | Cl |
| t-Bu | Me | Cl | CH₂SCHF₂ | Cl |
| c-Pr | Me | Cl | CH₂SCHF₂ | Cl |
| H | Me | Cl | CH₂S(O)₂CHF₂ | Cl |
| Me | Me | Cl | CH₂S(O)₂CHF₂ | Cl |
| Et | Me | Cl | CH₂S(O)₂CHF₂ | Cl |
| i-Pr | Me | Cl | CH₂S(O)₂CHF₂ | Cl |
| t-Bu | Me | Cl | CH₂S(O)₂CHF₂ | Cl |
| c-Pr | Me | Cl | CH₂S(O)₂CHF₂ | Cl |
| H | Me | H | CF₂OEt | Cl |
| Me | Me | H | CF₂OEt | Cl |
| Et | Me | H | CF₂OEt | Cl |
| i-Pr | Me | H | CF₂OEt | Cl |
| t-Bu | Me | H | CF₂OEt | Cl |
| c-Pr | Me | H | CF₂OEt | Cl |
| H | Me | H | CF₂OEt | F |
| Me | Me | H | CF₂OEt | F |

TABLE 5-continued

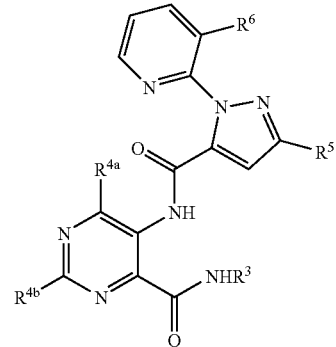

| R³ | R⁴ᵃ | R⁴ᵇ | R⁵ | R⁶ |
|---|---|---|---|---|
| Et | Me | H | CF₂OEt | F |
| i-Pr | Me | H | CF₂OEt | F |
| t-Bu | Me | H | CF₂OEt | F |
| c-Pr | Me | H | CF₂OEt | F |
| H | Cl | H | CF₂OEt | Cl |
| Me | Cl | H | CF₂OEt | Cl |
| Et | Cl | H | CF₂OEt | Cl |
| i-Pr | Cl | H | CF₂OEt | Cl |
| t-Bu | Cl | H | CF₂OEt | Cl |
| c-Pr | Cl | H | CF₂OEt | Cl |
| H | Cl | H | CF₂OEt | F |
| Me | Cl | H | CF₂OEt | F |
| Et | Cl | H | CF₂OEt | F |
| i-Pr | Cl | H | CF₂OEt | F |
| t-Bu | Cl | H | CF₂OEt | F |
| c-Pr | Cl | H | CF₂OEt | F |
| H | Me | Cl | CF₂OEt | Cl |
| Me | Me | Cl | CF₂OEt | Cl |
| Et | Me | Cl | CF₂OEt | Cl |
| i-Pr | Me | Cl | CF₂OEt | Cl |
| t-Bu | Me | Cl | CF₂OEt | Cl |
| c-Pr | Me | Cl | CF₂OEt | Cl |
| H | Me | Cl | CF₂OEt | F |
| Me | Me | Cl | CF₂OEt | F |
| Et | Me | Cl | CF₂OEt | F |
| i-Pr | Me | Cl | CF₂OEt | F |
| t-Bu | Me | Cl | CF₂OEt | F |
| c-Pr | Me | Cl | CF₂OEt | F |
| Me | Me | Br | CF₂OEt | Cl |
| Et | Me | Br | CF₂OEt | Cl |
| i-Pr | Me | Br | CF₂OEt | Cl |
| t-Bu | Me | Br | CF₂OEt | Cl |
| c-Pr | Me | Br | CF₂OEt | Cl |
| H | Me | Br | CF₂OEt | F |
| Me | Me | Br | CF₂OEt | F |
| Et | Me | Br | CF₂OEt | F |
| i-Pr | Me | Br | CF₂OEt | F |
| t-Bu | Me | Br | CF₂OEt | F |
| c-Pr | Me | Br | CF₂OEt | F |
| H | Cl | Cl | CF₂OEt | Cl |
| Me | Cl | Cl | CF₂OEt | Cl |
| Et | Cl | Cl | CF₂OEt | Cl |
| i-Pr | Cl | Cl | CF₂OEt | Cl |
| t-Bu | Cl | Cl | CF₂OEt | Cl |
| c-Pr | Cl | Cl | CF₂OEt | Cl |
| H | Cl | Cl | CF₂OEt | F |
| Me | Cl | Cl | CF₂OEt | F |
| Et | Cl | Cl | CF₂OEt | F |
| i-Pr | Cl | Cl | CF₂OEt | F |
| t-Bu | Cl | Cl | CF₂OEt | F |
| c-Pr | Cl | Cl | CF₂OEt | F |
| H | Me | CN | CF₂OEt | Cl |
| Me | Me | CN | CF₂OEt | Cl |
| Et | Me | CN | CF₂OEt | Cl |
| i-Pr | Me | CN | CF₂OEt | Cl |
| t-Bu | Me | CN | CF₂OEt | Cl |
| c-Pr | Me | CN | CF₂OEt | Cl |
| H | Me | CN | CF₂OEt | F |
| Me | Me | CN | CF₂OEt | F |

TABLE 5-continued

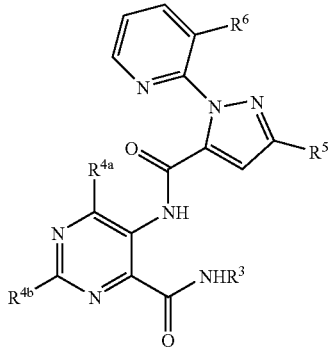

| R³ | R⁴ᵃ | R⁴ᵇ | R⁵ | R⁶ |
|---|---|---|---|---|
| Et | Me | CN | CF₂OEt | F |
| i-Pr | Me | CN | CF₂OEt | F |
| t-Bu | Me | CN | CF₂OEt | F |
| c-Pr | Me | CN | CF₂OEt | F |
| H | Me | Cl | CF₂OEt | CF₃ |
| Me | Me | Cl | CF₂OEt | CF₃ |
| Et | Me | Cl | CF₂OEt | CF₃ |
| i-Pr | Me | Cl | CF₂OEt | CF₃ |
| t-Bu | Me | Cl | CF₂OEt | CF₃ |
| c-Pr | Me | Cl | CF₂OEt | CF₃ |
| H | Me | Cl | CF₂OEt | CN |
| Me | Me | Cl | CF₂OEt | CN |
| Et | Me | Cl | CF₂OEt | CN |
| i-Pr | Me | Cl | CF₂OEt | CN |
| t-Bu | Me | Cl | CF₂OEt | CN |
| c-Pr | Me | Cl | CF₂OEt | CN |
| H | Me | I | CF₂OEt | Cl |
| Me | Me | I | CF₂OBt | Cl |
| Et | Me | I | CF₂OEt | Cl |
| i-Pr | Me | I | CF₂OEt | Cl |
| t-Bu | Me | I | CF₂OEt | Cl |
| c-Pr | Me | I | CF₂OEt | Cl |
| H | Me | F | CF₂OEt | Cl |
| Me | Me | F | CF₂OEt | Cl |
| Et | Me | F | CF₂OEt | Cl |
| i-Pr | Me | F | CF₂OEt | Cl |
| t-Bu | Me | F | CF₂OEt | Cl |
| c-Pr | Me | F | CF₂OEt | Cl |
| H | Br | Cl | CF₂OEt | Cl |
| Me | Br | Cl | CF₂OEt | Cl |
| Et | Br | Cl | CF₂OEt | Cl |
| i-Pr | Br | Cl | CF₂OEt | Cl |
| t-Bu | Br | Cl | CF₂OEt | Cl |
| c-Pr | Br | Cl | CF₂OEt | Cl |
| H | Cl | Br | CF₂OEt | Cl |
| Me | Cl | Br | CF₂OEt | Cl |
| Et | Cl | Br | CF₂OEt | Cl |
| i-Pr | Cl | Br | CF₂OEt | Cl |
| t-Bu | Cl | Br | CF₂OEt | Cl |
| c-Pr | Cl | Br | CF₂OEt | Cl |
| H | Me | Cl | CF₂SEt | Cl |
| Me | Me | Cl | CF₂SEt | Cl |
| Et | Me | Cl | CF₂SEt | Cl |
| i-Pr | Me | Cl | CF₂SEt | Cl |
| t-Bu | Me | Cl | CF₂SEt | Cl |
| c-Pr | Me | Cl | CF₂SEt | Cl |
| H | Me | Cl | CF₂S(O)Et | Cl |
| Me | Me | Cl | CF₂S(O)Et | Cl |
| Et | Me | Cl | CF₂S(O)Et | Cl |
| i-Pr | Me | Cl | CF₂S(O)Et | Cl |
| t-Bu | Me | Cl | CF₂S(O)Et | Cl |
| c-Pr | Me | Cl | CF₂S(O)Et | Cl |
| H | Me | Cl | CF₂S(O)₂Et | Cl |
| Me | Me | Cl | CF₂S(O)₂Et | Cl |
| Et | Me | Cl | CF₂S(O)₂Et | Cl |
| i-Pr | Me | Cl | CF₂S(O)₂Et | Cl |
| t-Bu | Me | Cl | CF₂S(O)₂Et | Cl |
| c-Pr | Me | Cl | CF₂S(O)₂Et | Cl |
| H | Me | H | CH₂OEt | Cl |

TABLE 5-continued

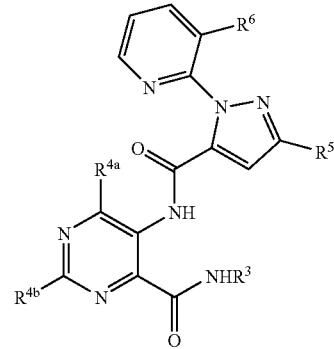

| R³ | R⁴ᵃ | R⁴ᵇ | R⁵ | R⁶ |
|---|---|---|---|---|
| Me | Me | H | CH₂OEt | Cl |
| Et | Me | H | CH₂OEt | Cl |
| i-Pr | Me | H | CH₂OEt | Cl |
| t-Bu | Me | H | CH₂OEt | Cl |
| c-Pr | Me | H | CH₂OEt | Cl |
| H | Cl | H | CH₂OEt | Cl |
| Me | Cl | H | CH₂OEt | Cl |
| Et | Cl | H | CH₂OEt | Cl |
| i-Pr | Cl | H | CH₂OEt | Cl |
| t-Bu | Cl | H | CH₂OEt | Cl |
| c-Pr | Cl | H | CH₂OEt | Cl |
| H | Me | Cl | CH₂OEt | Cl |
| Me | Me | Cl | CH₂OEt | Cl |
| Et | Me | Cl | CH₂OEt | Cl |
| i-Pr | Me | Cl | CH₂OEt | Cl |
| t-Bu | Me | Cl | CH₂OEt | Cl |
| c-Pr | Me | Cl | CH₂OEt | Cl |
| H | Me | H | CH₂SEt | Cl |
| Me | Me | H | CH₂SEt | Cl |
| Et | Me | H | CH₂SEt | Cl |
| i-Pr | Me | H | CH₂SEt | Cl |
| t-Bu | Me | H | CH₂SEt | Cl |
| c-Pr | Me | H | CH₂SEt | Cl |
| H | Cl | H | CH₂SEt | Cl |
| Me | Cl | H | CH₂SEt | Cl |
| Et | Cl | H | CH₂SEt | Cl |
| i-Pr | Cl | H | CH₂SEt | Cl |
| t-Bu | Cl | H | CH₂SEt | Cl |
| c-Pr | Cl | H | CH₂SEt | Cl |
| H | Me | Cl | CH₂SEt | Cl |
| Me | Me | Cl | CH₂SEt | Cl |
| Et | Me | Cl | CH₂SEt | Cl |
| i-Pr | Me | Cl | CH₂SEt | Cl |
| t-Bu | Me | Cl | CH₂SEt | Cl |
| c-Pr | Me | Cl | CH₂SEt | Cl |
| H | Me | Cl | CH₂S(O)Et | Cl |
| Me | Me | Cl | CH₂S(O)Et | Cl |
| Et | Me | Cl | CH₂S(O)Et | Cl |
| i-Pr | Me | Cl | CH₂S(O)Et | Cl |
| t-Bu | Me | Cl | CH₂S(O)Et | Cl |
| c-Pr | Me | Cl | CH₂S(O)Et | Cl |
| H | Me | Cl | CH₂S(O)₂Et | Cl |
| Me | Me | Cl | CH₂S(O)₂Bt | Cl |
| Et | Me | Cl | CH₂S(O)₂Et | Cl |
| i-Pr | Me | Cl | CH₂S(O)₂Et | Cl |
| t-Bu | Me | Cl | CH₂S(O)₂Et | Cl |
| c-Pr | Me | Cl | CH₂S(O)₂Et | Cl |
| H | Me | H | OS(O)₂Et | Cl |
| Me | Me | H | OS(O)₂Et | Cl |
| Et | Me | H | OS(O)₂Et | Cl |
| i-Pr | Me | H | OS(O)₂Et | Cl |
| t-Bu | Me | H | OS(O)₂Et | Cl |
| c-Pr | Me | H | OS(O)₂Et | Cl |
| H | Cl | H | OS(O)₂Et | Cl |
| Me | Cl | H | OS(O)₂Et | Cl |
| Et | Cl | H | OS(O)₂Et | Cl |
| i-Pr | Cl | H | OS(O)₂Et | Cl |
| t-Bu | Cl | H | OS(O)₂Et | Cl |
| c-Pr | Cl | H | OS(O)₂Et | Cl |

TABLE 5-continued

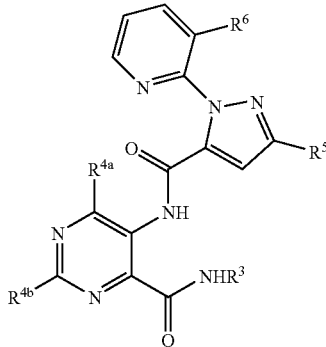

| R³ | R⁴ᵃ | R⁴ᵇ | R⁵ | R⁶ |
|---|---|---|---|---|
| H | Me | Cl | OS(O)₂Et | Cl |
| Me | Me | Cl | OS(O)₂Et | Cl |
| Et | Me | Cl | OS(O)₂Et | Cl |
| i-Pr | Me | Cl | OS(O)₂Et | Cl |
| t-Bu | Me | Cl | OS(O)₂Et | Cl |
| c-Pr | Me | Cl | OS(O)₂Et | Cl |
| H | Me | Cl | OS(O)₂CF₃ | Cl |
| Me | Me | Cl | OS(O)₂CF₃ | Cl |
| Et | Me | Cl | OS(O)₂CF₃ | Cl |
| i-Pr | Me | Cl | OS(O)₂CF₃ | Cl |
| t-Bu | Me | Cl | OS(O)₂CF₃ | Cl |
| c-Pr | Me | Cl | OS(O)₂CF₃ | Cl |
| H | Cl | Cl | OS(O)₂CF₃ | Cl |
| Me | Cl | Cl | OS(O)₂CF₃ | Cl |
| Et | Cl | Cl | OS(O)₂CF₃ | Cl |
| i-Pr | Cl | Cl | OS(O)₂CF₃ | Cl |
| t-Bu | Cl | Cl | OS(O)₂CF₃ | Cl |
| c-Pr | Cl | Cl | OS(O)₂CF₃ | Cl |
| H | Me | Cl | OCOCF₃ | Cl |
| Me | Me | Cl | OCOCF₃ | Cl |
| Et | Me | Cl | OCOCF₃ | Cl |
| i-Pr | Me | Cl | OCOCF₃ | Cl |
| t-Bu | Me | Cl | OCOCF₃ | Cl |
| c-Pr | Me | Cl | OCOCF₃ | Cl |
| H | Cl | Cl | OCH₂C≡CH | Cl |
| Me | Cl | Cl | OCH₂C≡CH | Cl |
| Et | Cl | Cl | OCH₂C≡CH | Cl |
| i-Pr | Cl | Cl | OCH₂C≡CH | Cl |
| t-Bu | Cl | Cl | OCH₂C≡CH | Cl |
| c-Pr | Cl | Cl | OCH₂C≡CH | Cl |
| H | Cl | Cl | OCH₂CH=CH₂ | Cl |
| Me | Cl | Cl | OCH₂CH=CH₂ | Cl |
| Et | Cl | Cl | OCH₂CH=CH₂ | Cl |
| i-Pr | Cl | Cl | OCH₂CH=CH₂ | Cl |
| t-Bu | Cl | Cl | OCH₂CH=CH₂ | Cl |
| c-Pr | Cl | Cl | OCH₂CH=CH₂ | Cl |
| H | Me | Cl | OCH₂-c-Pr | Cl |
| Me | Me | Cl | OCH₂-c-Pr | Cl |
| Et | Me | Cl | OCH₂-c-Pr | Cl |
| i-Pr | Me | Cl | OCH₂-c-Pr | Cl |
| t-Bu | Me | Cl | OCH₂-c-Pr | Cl |
| c-Pr | Me | Cl | OCH₂-c-Pr | Cl |
| H | Cl | Cl | OCH₂CCl=CH₂ | Cl |
| Me | Cl | Cl | OCH₂CCl=CH₂ | Cl |
| Et | Cl | Cl | OCH₂CCl=CH₂ | Cl |
| i-Pr | Cl | Cl | OCH₂CCl=CH₂ | Cl |
| t-Bu | Cl | Cl | OCH₂CCl=CH₂ | Cl |
| c-Pr | Cl | Cl | OCH₂CCl=CH₂ | Cl |
| H | Cl | Cl | OCH₂CH=CF₂ | Cl |
| Me | Cl | Cl | OCH₂CH=CF₂ | Cl |
| Et | Cl | Cl | OCH₂CH=CF₂ | Cl |
| i-Pr | Cl | Cl | OCH₂CH=CF₂ | Cl |
| t-Bu | Cl | Cl | OCH₂CH=CF₂ | Cl |
| c-Pr | Cl | Cl | OCH₂CH=CF₂ | Cl |
| H | Cl | Cl | NHS(O)₂CF₃ | Cl |
| Me | Cl | Cl | NHS(O)₂CF₃ | Cl |
| Et | Cl | Cl | NHS(O)₂CF₃ | Cl |
| i-Pr | Cl | Cl | NHS(O)₂CF₃ | Cl |
| t-Bu | Cl | Cl | NHS(O)₂CF₃ | Cl |

TABLE 5-continued

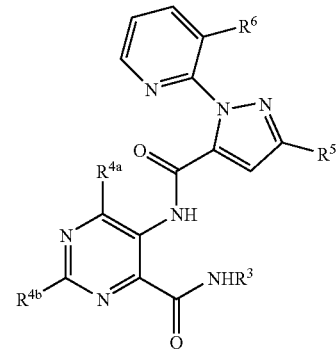

| R³ | R⁴ᵃ | R⁴ᵇ | R⁵ | R⁶ |
|---|---|---|---|---|
| c-Pr | Cl | Cl | NHS(O)₂CF₃ | Cl |
| H | Cl | Cl | NHCOCF₃ | Cl |
| Me | Cl | Cl | NHCOCF₃ | Cl |
| Et | Cl | Cl | NHCOCF₃ | Cl |
| i-Pr | Cl | Cl | NHCOCF₃ | Cl |
| t-Bu | Cl | Cl | NHCOCF₃ | Cl |
| c-Pr | Cl | Cl | NHCOCF₃ | Cl |
| H | Cl | Cl | OCH₂CN | Cl |
| Me | Cl | Cl | OCH₂CN | Cl |
| Et | Cl | Cl | OCH₂CN | Cl |
| i-Pr | Cl | Cl | OCH₂CN | Cl |
| t-Bu | Cl | Cl | OCH₂CN | Cl |
| c-Pr | Cl | Cl | OCH₂CN | Cl |
| H | Cl | Cl | OCH₂NO₂ | Cl |
| Me | Cl | Cl | OCH₂NO₂ | Cl |
| Et | Cl | Cl | OCH₂NO₂ | Cl |
| i-Pr | Cl | Cl | OCH₂NO₂ | Cl |
| t-Bu | Cl | Cl | OCH₂NO₂ | Cl |
| c-Pr | Cl | Cl | OCH₂NO₂ | Cl |
| H | Cl | Cl | O-c-Pr | Cl |
| Me | Cl | Cl | O-c-Pr | Cl |
| Et | Cl | Cl | O-c-Pr | Cl |
| i-Pr | Cl | Cl | O-c-Pr | Cl |
| t-Bu | Cl | Cl | O-c-Pr | Cl |
| c-Pr | Cl | Cl | O-c-Pr | Cl |
| H | Cl | Cl | CH₂OCHF₂ | Cl |
| Me | Cl | Cl | CH₂OCHF₂ | Cl |
| Et | Cl | Cl | CH₂OCHF₂ | Cl |
| i-Pr | Cl | Cl | CH₂OCHF₂ | Cl |
| t-Bu | Cl | Cl | CH₂OCHF₂ | Cl |
| c-Pr | Cl | Cl | CH₂OCHF₂ | Cl |
| H | Cl | Cl | CH₂SCHF₂ | Cl |
| Me | Cl | Cl | CH₂SCHF₂ | Cl |
| Et | Cl | Cl | CH₂SCHF₂ | Cl |
| i-Pr | Cl | Cl | CH₂SCHF₂ | Cl |
| t-Bu | Cl | Cl | CH₂SCHF₂ | Cl |
| c-Pr | Cl | Cl | CH₂SCHF₂ | Cl |
| H | Cl | Cl | CH₂S(O)₂CHF₂ | Cl |
| Me | Cl | Cl | CH₂S(O)₂CHF₂ | Cl |
| Et | Cl | Cl | CH₂S(O)₂CHF₂ | Cl |
| i-Pr | Cl | Cl | CH₂S(O)₂CHF₂ | Cl |
| t-Bu | Cl | Cl | CH₂S(O)₂CHF₂ | Cl |
| c-Pr | Cl | Cl | CH₂S(O)₂CHF₂ | Cl |

Formulation/Utility

Compounds of this invention will generally be used as a formulation or composition with an agronomic or nonagronomic suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, propylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 14; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
| --- | --- |
| Compound 1 | 10.0% |
| attapulgite granules (low volatile matter, 0.71/0.30 mm; U.S.S. No. 25-50 sieves) | 90.0%. |

EXAMPLE C

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

| Emulsifiable Concentrate | |
| --- | --- |
| Compound 1 | 20.0% |
| blend of oil soluble sulfonates and polyoxyethylene ethers | 10.0% |
| isophorone | 70.0%. |

EXAMPLE E

| Granule | |
| --- | --- |
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural crops (e.g., forest, greenhouse, nursery or ornamental plants not grown in a field), turf (commercial, golf, residential, recreational, etc.), wood products, public health (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Cleméns), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brown-banded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Apbididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migrato-* ria Linnaeus), bush locust (*Zonocerus* spp.) house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman), flower thrips (*Frankliniella* spp.) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps, sawflies (*Neodiprion* spp.; *Cephus* spp.); insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogrammma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirtothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus the present invention also pertains to a composition comprising a biologically effective amount of a compound of Formula 1, an N-oxide thereof, or an agronomic or nonagronomic suitable salt thereof, and an effective amount of at least one additional biologically active compound or agent and can further comprise at least one of a surfactant, a solid diluent or a liquid diluent. Examples of such biologically active compounds or agents with which compounds of this invention can be formulated are: insecticides such as abamectin, acephate, acetamiprid, acetoprole, amidoflumet (S-1955), avermectin, azadirachtin, azinphos-methyl, bifenthrin, bifenazate, bistrifluron, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltametirin, diafenthiuron, diazinon, diflubenzuron, dimethoate, dinotefuran, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, gamua-chalothrin, halofenozide, hexaflumuron, imidacloprid, indoxacarb, isofenphos, lufenuron, malathion, metaldehyde, methamidophos, methidathion, methomyl, methoprene, methoxymclor, methoxyfenozide, metofluthrin, monocrotophos, methoxyfenozide, novaluron, noviflumuron (XDE-007), oxamyl, parathion, parathion-methyl, permethrin, phorate, phosalone, phosmet, phosphamidon, pirimicarb, profenofos, profluthrin, protrifenbute, pymetrozine, pyridalyl, pyriproxyfen, rotenone, S1812 (Valent) spinosad, spiromesifen (BSN 2060), sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, trichlorfon and triflumuron; fungicides such as acibenzolar, S-methyl, azoxystrobin, benalazy-M, benthiavalicarb, benomyl, blasticidin-S, Bordeaux mixture (tribasic copper sulfate), boscalid, bromuconazole, buthiobate, carpropamid, captafol, captan, carbendazim, chloroneb, chlorothalonil, clotrimazole, copper oxychloride, copper salts, cymoxanil, cyazofamid, cyflufenamid, cyproconazole, cyprodinil, diclocymet, diclomezine, dicloran, difenoconazole, dimethomorph, dimoxystrobin, diniconazole, diniconazole-M, dodine, edifenphos, epoxiconazole, ethaboxam, famoxadone, fenarimol, fenbuconazole, fenhexamid, fenoxanil, fenpiclonil, fenpropidin, fenpropimorph, fentin acetate, fentin hydroxide, fluazinam, fludioxonil, flumorph, fluoxastrobin, fluquinconazole, flusilazole, flutolanil, flutriafol, folpet, fosetyl-aluminum, furalaxyl, furametapyr, guazatine, hexaconazole, hymexazol, imazalil, imibenconazole, iminoctadine, ipconazole, iprobenfos, iprodione, iprovalicarb, isoconazole, isoprothiolane, kasugamycin, kresoxim-methyl, mancozeb, maneb, mefenoxam, mepanapyrim, mepronil, metalaxyl, metconazole, metominostrobin/fenominostrobin, metrafenone, miconazole, myclobutanil, neo-asozin (ferric methanearsonate), nuarimol, oryzastrobin, oxadixyl, oxpoconazole, penconazole, pencycuron, picobenzamid, picoxystrobin, probenazole, prochloraz, propamocarb, propiconazole, proquinazid, prothioconazole, pyraclostrobin, pyrimethanil, pyrifenox, pyroquilon, quinoxyfen, silthiofam, simeconazole, sipconazole, spiroxamine, sulfur, tebuconazole, tetraconazole, tiadinil, thiabendazole, thifluzamide, thiophanate-methyl, thiram, tolylfluanid, triadimefon, triadimenol, triarimol, tricyclazole, trifloxystrobin, triflumizole, triforine, triticonazole, uniconazole, validamycin, vinclozolin and zoxamide; and biological agents such as *Bacillus thuringiensis* including ssp. *aizawai* and *kurstaki, Bacillus thuringiensis* delta endotoxin, baculovirus, and entomopathogenic bacteria, virus and fingi. Compounds of this invention and compositions thereof can be applied to plants genetically transformed to express proteins toxic to invertebrate pests (such as *Bacillus thuringiensis* toxin). The effect of the exogenously applied invertebrate pest control compounds of this invention may be synergistic with the expressed toxin proteins.

A general reference for these agricultural protectants is *The Pesticide Manual,* 12th Edition, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of the present invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or with a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

A compound of this invention can be incorporated into a bait composition that is consumed by an invertebrate pest or used within a devices such as a traps, bait stations, and the like. Such a bait composition can be in the form of granules which comprise (a) an active ingredient, namely a compound of Formula I, an N-oxide, or agronomic or nonagronomic suitable salt thereof, (b) one or more food materials, optionally (c) an attractant, and optionally (d) one or more humectants. Of note granules or bait compositions which comprise between about 0.001-5% active ingredient; about 40-99% food material and/or attractant; and optionally about 0.05-10% humectants; are effective in controlling soil invertebrate pests at very low application rates, particularly at doses of active ingredient that are lethal by ingestion rather than by direct contact. Of note some food materials will function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control an invertebrate pest including individually or in combinations ants, termites, and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g. a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a compound or composition of the present invention and a propellant. Representative propellants include, but are not limited to, methane, ethane, propane, iospropane, butane, isobutane, butene, pentane, iospentane, neopentane, pentene, hydrofluorocarbons, chlorofluoroacarbons, dimethyl ether, and mixtures of the foregoing. Of note is a spray composition (and a method utilizing such a spray composition dispensed from a spray container) used to control an invertebrate pest including individually or in combinations mosquitoes, black flies, stable flies, deer flies, horse flies, wasps, yellow jackets, hornets, ticks, spiders, ants, gnats, and the like.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Table A for compound descriptions. The following abbreviations are used in the Index Tables which follow: i is iso, Me is methyl, Et is ethyl, Pr is propyl, i-Pr is isopropyl, Ph is phenyl, $S(O)_2Me$ is methylsulfonyl, and CN is cyano. The abbreviation "Ex." stands for "Example" and is followed by a number indicating in which example the compound is prepared.

INDEX TABLE B

| Cmpd No. | $^1$H NMR Data (CDCl$_3$ solution unless indicated otherwise)$^a$ |
|---|---|
| 1 | DMSO-d6 2.84 (d,3H), 3.34 (s,3H), 6.58 (d,NH), 7.10 (s,1H), 7.20 (s,1H), 7.25 (s,1H), 7.37 (q,1H), 7.85 (d,1H), 8.45 (d,1H), 10.08 (brs,NH). |
| 2 | DMSO-d6 1.02 (d,6H), 3.57 (s,3H), 3.88 (m,1H), 7.32 (s,1H), 7.44 (d,1H), 7.62 (q,1H), 7.83 (d,1H), 8.15 (d,1H), 8.25 (brs,NH), 8.45 (d,1H), 10.55 (brs,NH). |

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid

INDEX TABLE A

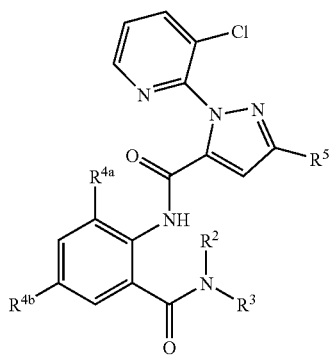

| Compound | $R^2$ | $R^3$ | $R^{4a}$ | $R^{4b}$ | $R^5$ | m.p. (° C.) |
|---|---|---|---|---|---|---|
| 1(Ex. 2) | H | i-Pr | Cl | Cl | $OS(O)_2Me$ | * |
| 2(Ex. 1) | H | Me | Cl | Cl | $OS(O)_2Me$ | * |
| 3 | H | Me | Cl | Cl | $O(CH_2)_2OEt$ | 133-134 |
| 4 | H | i-Pr | Cl | Cl | $O(CH_2)_2OEt$ | 205-206 |
| 5 | H | Me | Cl | Cl | $OCH_2Ph$ | 106-107 |
| 6 | Me | Me | Cl | Cl | $OCH_2C\equiv CH$ | 194-195 |
| 7 | H | Me | Cl | Cl | $OCH_2C\equiv CH$ | 204-205 |
| 8(Ex. 3) | H | i-Pr | Cl | Cl | $OCH_2C\equiv CH$ | 188-189 |
| 9 | Me | Me | Cl | Cl | $OCH_2CO_2Me$ | 189-190 |
| 10 | H | Me | Cl | Cl | $OCH_2CO_2Me$ | 212-213 |
| 11 | H | Me | Cl | Cl | $OCH_2CN$ | 129-130 |
| 12 | H | Me | Cl | Cl | $OCH_2$-5-(2-Cl-pyridinyl) | 127-128 |
| 13 | H | Me | Me | Cl | $OCH_2OMe$ | 205-206 |
| 14 | H | i-Pr | Cl | Cl | $OCH_2CN$ | 181-182 |
| 15 | H | Me | Cl | Cl | $OS(O)_2CF_3$ | 188-189 |
| 16 | H | Me | Cl | Cl | $OCH_2C(Cl)\!\!=\!\!CH_2$ | 123-125 |
| 17 | H | Me | Me | Cl | $OSO_2CF_3$ | 129-130 |
| 18 | H | Me | Me | CN | $OCH_2CN$ | 125-126 |

*See Index Table B for $^1$H NMR data.

through a SUJ2 atomizer nozzle with ⅛ JJ custom body (Spraying Systems Co. Wheaton, Ill., USA) positioned 1.27 cm (0.5 inches) above the top of each test unit. Test compounds 1 through 17 were sprayed at 50 ppm and test compound 18 was sprayed at 10 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed.

Of the compounds tested the following provided very good to excellent levels of plant protection (20% or less feeding damage): 1, 2, 3, 4, 5, 6, 7, 8, 11, 12, 13, 14, 15, 16, 17 and 18.

Test B

For evaluating control of fall armyworm (*Spodoptera frugiperda*) the test unit consisted of a small open container with a 45-day-old corn (maize) plant inside. This was pre-infested (using a core sampler) with 10-15 1-day-old larvae on a piece of insect diet.

Test compounds 1 through 17 were formulated and sprayed at 50 ppm and test compound 18 was formulated sprayed at 10 ppm as described for Test A. The applications were replicated three times. After spraying, the test units were maintained in a growth chamber and then visually rated as described for Test A.

Of the compounds tested, the following provided excellent levels of plant protection (20% or less feeding damage): 1, 3, 4, 5, 6, 7, 8, 11, 12, 13, 14, 15, 16, 17 and 18.

Test C

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.). The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm, replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality. Of the compounds tested, the following resulted in at least 80% mortality: 11 and 18.

Test D

For evaluating control of potato leafhopper (*Empoasca fabae* Harris) through contact and/or systemic means, the test unit consisted of a small open container with a 5-6 day old Longio bean plant (primary leaves emerged) inside. White sand was added to the top of the soil and one of the primary leaves was excised prior to application. Test compounds were formulated and sprayed at 250 ppm and replicated three times as described for Test C. After spraying, the test units were allowed to dry for 1 hour before they were post-infested with 5 potato leafhoppers (18 to 21 day old adults). A black, screened cap was placed on the top of the cylinder. The test units were held for 6 days in a growth chamber at 19-21° C. and 50-70% relative humidity. Each test unit was then visually assessed for insect mortality. Of the compounds tested, the following resulted in at least 80% mortality: 11.

What is claimed is:

1. A compound of Formula I, its N-oxide or an agronomic or nonagronomic suitable salt therof

I 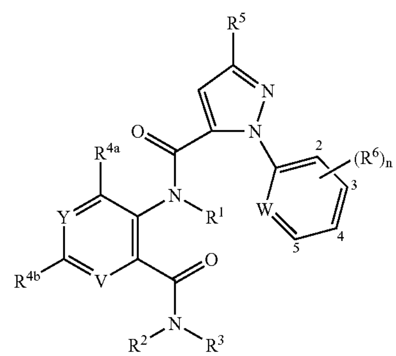 wherein:

Y and V are CH;

W is N;

$R^1$ is H;

$R^2$ is H or $CH_3$;

$R^3$ is $C_1$-$C_4$ alkyl;

$R^{4a}$ is H, $CH_3$, Cl, Br or I;

$R^{4b}$ is H, F, Cl, Br, I, CN or $CF_3$;

$R^5$ is $C_2$-$C_6$ alkenyloxy, $C_2$-$C_6$ alkynyloxy, $C_1$-$C_6$ alkoxy substituted with CN or substituted with $C_1$-$C_2$ alkoxy;

each $R^6$ is independently halogen, CN, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$;

n is 0 or 1; and p is 0, 1 or 2.

2. A composition for controlling an invertebrate pest comprising a biologically effective amount of a compound of claim 1 and at least one additional component selected from the group consisting of a surfactant, a solid diluent, and a liquid diluent, said composition optionally further comprising an effective amount of at least one additional biologically active compound or agent.

3. The composition of claim 2 wherein the additional biologically active compound or agent is present and is selected from the group consisting of cypermethrin, cyhalothrin, cyfluthrin, beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, γ-aminobutyric acid, endosulfan, ethiprole, fipronil, flufenoxuron, triflumuron, diofenolan, pyriproxyfen, pymetrozine, amitraz, *Bacillus thuringiensis, Bacillus thuringiensis* delta endotoxin, a member of the family Baculoviridae, and entomophagous fungi.

4. A method for controlling an invertebrate pest comprising contacting the invertebrate pest or its environment with a biologically effective amount of a compound of claim 1.

5. The method of claim 4 wherein the invertebrate pest is a cockroach, an ant or a termite which contacts the compound by consuming a bait composition comprising the compound or the composition.

6. The method of claim 4 wherein the invertebrate pest is a mosquito, a black fly, a stable fly, a deer fly, a horse fly, a wasp, a yellow jacket, a hornet, a tick, a spider, an ant, or a gnat which is contacted by a spray composition comprising the compound or the composition dispensed from a spray container.

* * * * *

UNITED STATES PATENT AND TRADEMARK OFFICE
CERTIFICATE OF CORRECTION

PATENT NO.        : 7,666,882 B2                                        Page 1 of 1
APPLICATION NO. : 10/529612
DATED             : February 23, 2010
INVENTOR(S)       : George Philip Lahm It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this

Seventh Day of December, 2010

David J. Kappos
*Director of the United States Patent and Trademark Office*